(12) United States Patent
MacPhee et al.

(10) Patent No.: US 6,682,695 B2
(45) Date of Patent: Jan. 27, 2004

(54) METHODS FOR STERILIZING BIOLOGICAL MATERIALS BY MULTIPLE RATES

(75) Inventors: Martin MacPhee, Montgomery Village, MD (US); William N. Drohan, Springfield, VA (US); Randall S. Kent, Thousand Oaks, CA (US); Tom Lynch, Rockville, MD (US); Glenn Calvert, Frederick, MD (US); Shirley Miekka, Gaithersburg, MD (US); David Mann, Gaithersburg, MD (US); Wilson Burgess, Clifton, VA (US)

(73) Assignee: Clearant, Inc., Los Angeles, CA (US)

( * ) Notice: Subject to any disclaimer, the term of this patent is extended or adjusted under 35 U.S.C. 154(b) by 0 days.

(21) Appl. No.: 10/197,248

(22) Filed: Jul. 18, 2002

(65) Prior Publication Data

US 2003/0161753 A1 Aug. 28, 2003

Related U.S. Application Data

(63) Continuation-in-part of application No. 09/973,958, filed on Oct. 11, 2001, which is a continuation-in-part of application No. PCT/US01/09361, filed on Mar. 23, 2001.

(51) Int. Cl.$^7$ ................................................. A61L 2/08
(52) U.S. Cl. ........................................ 422/22; 435/408
(58) Field of Search ............................ 422/22; 435/408

(56) References Cited

U.S. PATENT DOCUMENTS

| | | |
|---|---|---|
| 2,456,909 A | 12/1948 | Brasch |
| RE23,195 E | 2/1950 | Brasch |
| 2,832,689 A | 4/1958 | Proctor et al. |
| 2,920,969 A | 1/1960 | Stoddard |
| 2,962,380 A | 11/1960 | Wertheim |
| 3,620,944 A | 11/1971 | Tanito |
| 3,706,631 A * | 12/1972 | Falk |
| 3,743,480 A | 7/1973 | Falk |
| 3,779,706 A | 12/1973 | Nablo |
| 4,136,094 A | 1/1979 | Condie |
| 4,251,437 A | 2/1981 | Rasmussen et al. |
| 4,282,863 A | 8/1981 | Beigler et al. |
| 4,330,626 A | 5/1982 | Blair et al. |
| 4,336,247 A | 6/1982 | Eriksen |
| 4,370,264 A | 1/1983 | Kotitschke et al. |
| 4,409,105 A | 10/1983 | Hayashi et al. |
| 4,472,840 A | 9/1984 | Jefferies |
| 4,620,908 A | 11/1986 | Van Duzer |
| 4,727,027 A | 2/1988 | Wiesehahn et al. ......... 435/173 |
| 4,784,850 A | 11/1988 | Abraham |
| 4,798,611 A | 1/1989 | Freeman, Jr. |
| 4,865,602 A | 9/1989 | Smestad et al. |
| 4,931,361 A | 6/1990 | Baldeschwieler et al. |
| 4,933,145 A | 6/1990 | Uchida et al. |
| 4,946,648 A | 8/1990 | Dichtelmüller et al. |
| 4,963,356 A | 10/1990 | Calenoff et al. |
| 4,994,237 A | 2/1991 | Login et al. ................ 422/21 |
| 5,000,951 A | 3/1991 | Bass et al. |
| 5,012,503 A | 4/1991 | Nambu et al. |
| 5,044,091 A | 9/1991 | Ueda et al. |
| 5,106,619 A | 4/1992 | Wiesehahn et al. |
| 5,134,295 A | 7/1992 | Wälischmiller |
| 5,185,371 A | 2/1993 | Rubinstein |
| 5,226,065 A | 7/1993 | Held et al. |
| 5,283,034 A | 2/1994 | Okrongly et al. |
| 5,362,442 A | 11/1994 | Kent |
| 5,418,130 A | 5/1995 | Platz et al. |
| 5,460,962 A | 10/1995 | Kemp |
| 5,510,122 A | 4/1996 | Sreebny et al. |
| 5,548,066 A | 8/1996 | Leneau et al. |
| 5,603,894 A | 2/1997 | Aikus et al. |
| 5,609,864 A | 3/1997 | Shanbrom |
| 5,637,451 A | 6/1997 | Ben-Hur et al. |
| 5,643,464 A | 7/1997 | Rhee et al. |
| 5,712,086 A | 1/1998 | Horowitz et al. |
| 5,730,933 A | 3/1998 | Peterson |
| 5,817,528 A | 10/1998 | Böhm et al. |
| 5,837,313 A | 11/1998 | Ding et al. |
| 5,856,172 A | 1/1999 | Greenwood et al. |
| 5,880,477 A | 3/1999 | Perilleux et al. ......... 250/492.3 |
| 5,881,534 A | 3/1999 | Ahlqvist et al. |
| 5,981,163 A | 11/1999 | Horowitz et al. |
| 5,986,168 A | 11/1999 | Noishiki |
| 5,989,498 A | 11/1999 | Odland |
| 6,010,719 A | 1/2000 | Remon et al. |
| 6,046,024 A | 4/2000 | Burton et al. |

(List continued on next page.)

FOREIGN PATENT DOCUMENTS

| | | |
|---|---|---|
| CA | 2056619 | 10/1991 |
| DD | 228738 A1 * | 10/1985 |
| EP | 310 316 | 4/1989 |
| EP | 334 679 | 9/1989 |
| EP | 919 198 A2 | 6/1999 |
| EP | 919 198 A3 | 6/1999 |
| EP | 0808167 B1 | 6/2002 |
| EP | 0820301 B1 | 7/2002 |
| JP | 11-216147 | 8/1999 |
| SU | 1321420 A | 7/1987 |
| WO | WO 90/00907 | 2/1990 |

(List continued on next page.)

OTHER PUBLICATIONS

Davies et al. "Protein Damage and Degradation by Oxygen Radicals, II. Modification of Amino Acids," The Journal of Biological Chemistry, vol. 262 (20), pp. 9902–9907, 1987.*

(List continued on next page.)

Primary Examiner—Elizabeth McKane
(74) Attorney, Agent, or Firm—Fleshner & Kim, LLP

(57) ABSTRACT

Methods are disclosed for sterilizing biological materials to reduce the level of one or more biological contaminants or pathogens therein, such as viruses, bacteria (including inter- and intracellular bacteria, such as mycoplasmas, ureaplasmas, nanobacteria, chlamydia, rickettsias), yeasts, molds, fungi, single or multicellular parasites, and/or prions or similar agents responsible, alone or in combination, for TSEs.

224 Claims, No Drawings

U.S. PATENT DOCUMENTS

| | | | |
|---|---|---|---|
| 6,049,025 | A | 4/2000 | Stone et al. |
| 6,060,233 | A | 5/2000 | Wiggins |
| 6,066,626 | A | 5/2000 | Yew et al. |
| 6,087,141 | A | 7/2000 | Margolis-Nunno et al. |
| 6,120,592 | A | 9/2000 | Brault et al. |
| 6,159,490 | A | 12/2000 | Deghenghi |
| 6,171,549 | B1 | 1/2001 | Kent |
| 6,187,572 | B1 | 2/2001 | Platz et al. |
| 6,190,855 | B1 | 2/2001 | Herman et al. |
| 6,197,207 | B1 | 3/2001 | Chapman et al. |
| 6,203,544 | B1 | 3/2001 | Gotzen |
| 6,214,534 | B1 | 4/2001 | Horowitz et al. |
| 6,235,508 | B1 | 5/2001 | Sowemimo-Coker et al. |
| 6,258,821 | B1 | 7/2001 | Stogniew et al. |
| 6,312,931 | B1 | 11/2001 | O'Dwyer et al. ......... 435/173.1 |
| 6,346,216 | B1 | 2/2002 | Kent ........................... 422/22 |
| 6,358,284 | B1 | 3/2002 | Fearnot et al. ........... 623/23.72 |
| 6,375,989 | B1 | 4/2002 | Badylak et al. .............. 424/551 |
| 6,383,732 | B1 | 5/2002 | Stone ......................... 435/1.1 |
| 6,383,810 | B2 | 5/2002 | Fike et al. .................. 435/384 |
| 6,384,419 | B1 | 5/2002 | Purtle ......................... 250/526 |
| 6,461,630 | B1 | 10/2002 | Tucker et al. ............... 424/423 |
| 6,485,723 | B1 | 11/2002 | Badylak et al. ............ 424/93.7 |
| 6,548,242 | B2 | 4/2003 | Horowitz et al. .............. 435/2 |
| 2002/0064807 | A1 | 5/2002 | Badylak et al. ................ 435/34 |
| 2002/0068267 | A1 | 6/2002 | Horowitz et al. .............. 435/2 |
| 2002/0106394 | A1 | 8/2002 | Tucker et al. ............... 424/423 |
| 2002/0188319 | A1 | 12/2002 | Morris et al. ............... 606/213 |
| 2003/0068815 | A1 | 4/2003 | Stone et al. ................ 435/325 |

FOREIGN PATENT DOCUMENTS

| | | |
|---|---|---|
| WO | WO 91/16060 | 10/1991 |
| WO | WO 95/03071 | 2/1995 |
| WO | WO 00/25839 | 3/2000 |
| WO | WO 00/28552 | 5/2000 |
| WO | WO 01/08611 A1 | 2/2001 |
| WO | WO 01/12318 A1 | 2/2001 |
| WO | WO 01/32107 A2 | 5/2001 |
| WO | WO 01/32110 A2 | 5/2001 |
| WO | WO 01/45720 A1 | 6/2001 |
| WO | WO 01/49219 A1 | 7/2001 |
| WO | WO 01/72233 A1 | 10/2001 |
| WO | WO 01/72244 A1 | 10/2001 |
| WO | WO 01/91818 A1 | 12/2001 |

OTHER PUBLICATIONS

Plavsic et al. "Gamma Irradiation of Bovine Sera," Animal Sera, Animal Sera Derivatives and Substitutes Used in the Manufacture of Pharmaceuticals: Viral Safety and Regulatory Aspects. Dev Biol. Stand., vol. 99, pp. 95–109, 1999.*

Zabal et al. "Contamination of fetal bovine serum with bovine viral diarrhea virus" Revista Argentina de Microbiologia, vol. 32 (1), pp. 27–32, 2000, abstract only.*

Robert J. Woods, "Food Irradiation," Endeavor, New Series, vol. 18, No. 3, 1994, pp. 104–108.

A. Dziedzic-Goclawska et al., "Sterilisation of Tissue Allografts," Advances in Tissue Banking, vol. 1, pp. 261–321, prior art.

M.J. Goertzen et al., "Sterilisation of Canine Anterior Cruciate Allografts by Gamma Irradiation in Argon," Journal of Bone and Joint Surgery (Corrections), vol. 77–B, No. 2, Mar. 1995, pp. 205–212.

R.D.H. Chu et al., "Use of Ceric Sulphate and Perspex Dosimeters for the Calibration of Irradiation Facilities," IAEA–SM–192/14, pp. 83–99 and 224, prior art.

B. Whittaker et al., "The Influence of Dose Rate, Ambient Temperature and Time on the Radiation Response of Harwell PMMA Dosimeters," Radiation Physics and Chemistry, vol. 60, 2001, pp. 101–110.

P.H.G. Sharpe et al., "Real Time Dosimetry Measurements at an Industrial Irradiation Plant," Radiation Physics and Chemistry, vol. 57, 2000, pp. 687–690.

W.L. McLaughlin et al., "Preservation of Food by Ionizing Radiation," Chapter 8, vol. I, 1982, pp. 189–245.

A. Brynjolfsson, "Cobalt–60 Irradiator Designs," pp. 145–172, prior art.

J. P. Farrell et al., "Sterilization—Selecting a Radiation Sterilization Method," Medical Device & Diagnostic Industry, Aug. 1995, pp. 82–90.

AABB FDA Liaison Meeting, ABC Newsletter, p. 14 (Dec. 12, 1997).

Alladine, M.F. et al., γ–Radiation Damage to Starr–Edwards Valves, The Lancet, 1:594 (1968).

Alper, T. et al., Protection by Anoxia of the Scrapie Agent and some DNA and RNA Viruses Irradiated as Dry Preparations, J. Gen. Virol., 3:157–166 (1968).

Alper, T. et al., Does the Agent of Scrapie Replicate Without Nucleic Acid?, Nature, 214:764–766 (1967).

Alper, T. et al., The Exceptionally Small Size of the Scrapie Agent, Biochemical and Biophysical Research Communications, 22:278–284 (1996).

Alper, T. et al., The Scrapie Agent: Evidence Against its Dependence For Replication on Intrinsic Nucleic Acid, J. Gen. Virol., 41:503–516 (1978).

Akkus, O. et al., Fracture Resistance of Gamma Radiation Sterilized Cortical Bone Allografts, J. Orthapaedic Research, 19:927–934 (2001) (Elsevier Science Ltd.).

Aparicio, S.R. et al., Light and Electron Microscopy Studies on Homograft and Heterograft Heart Valves, J. Path., 115:147–162 (1975).

Baksa, J. et al., The Use of Pig's Skin (xenograft) for the Treatment of Burns, Magyar Traumatologia, 19:138–145 (1976).

Baldwin, M.L. et al., Irradiation of Blood Components, pp. 10–78 (1992) (American Association of Blood Banks).

Baquey, C. et al.., Radiosterilization of Albuminated Polyester Prostheses, Biomaterials, 8:185–189 (1987).

Bassin, R.H. et al., Abrogation of $Fv-1^b$ Restriction With Murine Leukemia Viruses Inactivated by Heat or by Gamma Irradiation, Journal of Virology, 26:306–315 (1978) (American Society for Microbiology).

Beauregard, G. et al., Temperature Dependence of the Radiation Inactivation of Proteins, Analytical Biochemistry, 150:117–120 (1985) (Academic Press Inc.).

Bedrossian Jr., E.H. et al., HIV and Banked Fascia Lata, Ophthalmic Plastic and Reconstructive Surgery, 7:284–288 (1991) (Raven Press Ltd.).

Belov, A.A. et al., The Influence of γ–Radiation on Enzyme Activity of Collalitin in the Process of Storage, Radiobiologiia, 30:519–521 (1990).

Bingci, L., Mouse Antibody Response Following Repetitive Injections of Gamma–Irradiated Human Placenta Collagen, Chinese Medical Sciences Journal, 9:100–103 (1994).

Blakeslee, S., Lack of Oversight in Tissue Donation Raising Concerns, The New York Times, Late Edition, pp. 1, 22 (Jan. 20, 2002) (http://query.nytimes.com).

Blanchy, B.B. et al., Immobilization of Factor VIII on Collagen Memb ranes, J. Biomedical Materials Research, 20:469–479 (1986) (John Wiley & Sons, Inc.).

Block, S.S., Disinfection, Sterilization, and Preservation,, Fourth Edition, pp. 31–33 (1991) (Lea & Febiger) (Philadelphia).

Bogers, A.J.J.C. et al., Long–Term Results of the Gamma–Irradiation–Preserved Homograft Monocusp for Transannular Reconstruction of the Right–Ventricular Outflow Tract in Tetralogy of Fallot, Thorac. Cardiovasc. Surgeon, 42:337–339 (1994) (Georg Thieme Verlag Stuttgart).

Borisova, E.A. et al., Protein Degradation During Interphase Death of Thymocytes induced by Radation and Dexamethasone, Radiobiologiia, 30:517–519 (1990).

Boyer, T.D. et al., Radiation Inactivation of Microsomal Glutathione S–Transferase, The Journal of Biological Chemistry, 261:16963–16968 (1986).

Brown, D.R. et al., Antioxidant Activity Related to Copper Binding of Native Prion Protein, J. Neurochem., 76:69–76 (2001) (Int'l Society for Neurochem.).

Brown, P. et al., The Distribution of Infectivity in Blood Components and Plasma Derivatives in Experimental Models of Transmissible Spongiform Encephalopathy, Transfusion, 38:810–816 (1998).

Brown, P. et al., Effect of Chemicals, Heat and Histopathologic Processing on High–Infectivity Hamster–Adapted Scrapie Virus, J. Infectious Diseases, 145:683–687 (1982) (University of Chicago).

Brown, P. et al., Further Studies of Blood Infectivity in an Experimental Model of Transmissible Spongiform Encephalopathy, With an Explanation of Why Blood Components Do Not Transmit Cruetzfeldt–Jakob Disease in Humans, Transfusion, 39:1169–1178 (1999).

Brown, P., The Risk of Blood–Borne Creutzfeldt–Jakob Disease, Advances in Transfusion Safety Dev. Biol., 102:53–59 (1999).

Burwell, R.G., The Fate of Freeze–Dried Bone Allografts, Transplantation Proceedings, 8(Suppl):95–111 (1976).

Callegaro, L. et al., Hollow Fiber Immobilized L–Asparaginase: In Vivo and In Vitro Immunological Studies, The International Journal of Artificial Organs, 6:91–96 (1983) (Wichtig Editore).

Campalani, G. et al., Aortic Valve Replacement With Frozen Irradiated Homografts, Eur. J. Cardio–thorac. Surg., 3:558–561 (1989) (Springer–Verlag).

Campbell, D.G. et al., Sterilization of HIV With Irradiation: Relevance to Infected Bone Allografts, Aust. N.Z. J. Surg., 69:517–521 (1999).

Chanderkar, L.P. et al.., The Involvement of Aromatic Amino Acids in Biological Activity of Bovine Fibrinogen as Assessed by Gamma–Irradiation, Radiation Research, 65:283–291 (1976) (Academic Press, Inc.).

Chanderkar, L.P. et al.., Radiation–Induced Changes In Purified Prothrombin and Thrombin, Biochimica et Biophysica Acta, 706:1–8 (1982) (Elsevier Biomedical Press).

Cheung, D. T. et al., The Effect of γ–Irradiation on Collagen Molecules, Isolated α–chains and Crosslinked Native Fibers, J. Biomedical Materials Research, 24:581–589 (1990) (John Wiley & Sons, Inc.).

Chin S. et al., Virucidal Treatment of Blood Protein Products With UVC Radiation, Photochemistry and Photobiology, 65:432–435 (1997) (American Society for Photobiology).

Chuchalin, A.G. et al., Clinical Immunosorbents Basing on Space–Network Polymers, Bioorg Khim, 14:1524–1529 (1988) (Russia).

Cohen, D. J. et al., The Fate of Aortic Valve Homografts 12 to 17 Years After Implantation, Chest, 93:482–484 (1988).

Conrad, E. U. et al., Transmission of the Hepatitis–C Virus by Tissue Transplantation, J. Bone and Joint Surgery, 77–A:214–224 (1995).

Cornu, O. et al., Effect of Freeze–drying and Gamma Irradiation on the Mechanical Properties of Human Cancellous Bone, J. Orthopaedic Research, 18:426–431 (2000).

Dagli, A. S., Correction of Saddle Nose Deformities by Coral Implantation, Eur. Arch. Otorhinolaryngol., 254:274–276 (1997) (Springer–Verlag).

Defeng et al., Sterilization of Silver–Acidum Pipemedicum Skin for the Treatment of Burns by Radioactive Cobalt–60–.Gamma.–Ray, Radiat. Phys. Chem., 46:4–6 (Caplus Abstract No. 1995:923966) (1995).

De Deyne, P. et al., Some Effects of Gamma Irradiation on Patellar Tendon Allografts, Connective Tissue Research, 27:51–62 (1991) (Gordon and Breach Science Publishers S. A.).

Di Simplicio, P. et al., The Reactivity of the SH Group of Bovine Serum Albumin With Free Radicals, Free Rad. Res. Commsl., 14:253–262 (1991) (Harwood Academic Publishers GmbH).

Donnelly, R.J. et al., Gamma–radiation of Heart Valves at 4° C.; A Comparative Study Using Techniques of Histochemistry and Electron and Light Microscopy, Thorax, 28:95–101 (1973).

Dyskin, E.A. et al., Hemomicrocirculatory Bed in the Wall of Hollow Organs of the Dog Gastrointestinal Tract at Portal Hypertension, Arkh Anat Gistol Embiol, 93:58–68 (1987).

Dziedzic–Goclawska, A. et al., Effect of Radiation Sterilization on the Osteoinductive Properties and the Rate of Remodeling of Bone Implants Preserved by Lyophilization and Deep–Freezing, Clinical Orthopaedics and Related Research, 272:30–37 (1991).

Eichler, D.C. et al., Radiation Inactivation Analysis of Enzymes, J. Biological Chemistry, 262:9433–9436 (1987).

Elliot, L.H. et al., Inactivation of Lassa, Marburg and Ebola Viruses by Gamma Irradiation, J. Clinical Microbiology, 16:704–708 (1982) (American Society for Microbiology).

Fideler, B. M. et al., Gamma Irradiation: Effects on Biomechanical Properties of Human Bone–Patellar Tendon–Bone Allografts, American Journal of Sports Medicine, 23:643–646 (1995).

Fideler, B.M. et al., Effects of Gamma Irradiation on the Human Immunodeficiency Virus, J. Bone and Joint Surgery, 76–A:1032–1035 (1994) (The Journal of Bone and Joint Surgery, Inc.).

Field, E.J. et al., Susceptibility of Scrapie Agent to Ionizing Radiation, Nature, 222:90–91 (1969).

Ghosh, M.M. et al., A Comparison of Methodologies for the Preparation of Human Epidermal–Dermal Composites, Annals of Plastic Surgery; 39:390–404 (1997) (Lippincott–Raven Publishers).

Gibbons, M.J. et al., Effects of Gamma Irradiation on the Initial Mechanical and Material Properties of Goat BonePatellar Tendon–Bone Allografts, J. Orthop Res., 9:209–218 (1991) (Orthopaedic Research Society).

Gibbons, J.R.P. et al., Gamma Ray Sterilisation of Homograft Valves, Bulletin De Le Societe Internationale de Chirugie, 3:353–358 (1969).

Goertzen, M.J. et al., Anterior Cruciate Ligament Reconstruction Using Cruopreserved Irradiated Bone–ACL–Bone–Allograft Transplants, Knee Surg. Sports Traumatol. Arthroscopy, 2:150–157 (1994) (Springer–Verlag).

Goertzen, M.J. et al., Sterilisation of Canine Anterior Cruciate Allografts by Gamma Irradiation in Argon, J. Bone and Joint Surgery, 77–B:205–212 (1995) (British Editorial Society of Bone and Joint Surgery) (Retracted).

Gregorczyn, S. et al., Strength of Lyophilized and Irradiated Cortical Bone of the Human Femur, Chir. Narz, Ruchu Ortop. Pol., 60:129–133 (1995).

Guidoin, R. et al., A Compound Arterial Prosthesis: The Importance of the Sterilization Procedure on the Healing and Stability of Albuminated Polyester Grafts, Biomaterials, 6:122–128 (1985) (Butterworth & Co. Ltd.).

Haig, D.A. et al., Further Studies on the Inactivation of the Scrapie Agent by Ultraviolet Light, J. Gen. Virol, 5:455–457 (1969).

Hehrlein, F. W. et al., Biochemical Changes in Heterologous Aortic Valve Transplants Following Application of Various Sterilization Methods, Langenbecks Arch Chair, 325:1183–1185 (1969).

Hehrlein, F.W. et al., Morphological Studies on Heterologous Heart Valve Transplants Under Various Sterilization Conditions, Thoraxchir vask Chir, 17: 244–251 (1969).

Hernigou, P. et al., Radiation Sterilization of Bone and the HIV Virus, Revue de Chirurgie Orthopédique, 79:445–451 (1993) (Masson, Paris).

Hiemstra, H. et al., Inactivation of Human Immunodeficiency Virus by Gamma Radiation and its Effect on Plasma and Coagulation Factors, Transfusion, 31:32–39 (1991).

Hinton, R. et al., A Biomechanical Analysis of Solvent–dehydrated and Freeze–Dried Human Fascia Lata Allografts, The American Journal of Sports Medicine, 20:607–612 (1992) (Am. Orthopaedic Soc. for Sports Medicine).

Horowitz, B. et al., Inactivation of Viruses in a Labile Blood Derivatives, II. Physical Methods, Transfusion, 25:523–527 (1985).

Horowitz, M., Sterilization of Homograft Ossicles by Gamma Radiation, J. Laryngology and Otology, 93:1087–1089 (1979).

House, C. et al., Inactivation of Viral Agents in Bovine Serum by Gamma Irradiation, Can. J. Microbiol., 36:737–740 (1990).

Hsiue, G. et al., Absorbable Sandwich–Like Membrane for Retinal–Sheet Transplantation, pp. 20–25 (2002) (Wiley Periodicals, Inc).

Ijiri, S. et al., Effect of Sterilization on Bone Morphogenetic Protein, J. Orthopaedic Research, 12:628–636 (1994) (Orthopaedic Research Society).

Imamaliev, A.S. et al., Biological Properties of Bone Tisue Conserved in Plastic Material and Sterilized With Gama Rays, ACTA Chirurgiae Plasticae, 16:129–135 (1974) (Avicenum, zdravotnické nakladatelství).

Ingegneri, A. et al., An 11–Year Assessment of 93 Flash-frozen Homograft Valves in the Aortic Position, Thorac., Carciovasc. Surgeon, 27:304–307 (1979) (Georg Thieme Verlag Stuttgart).

Jensen, J. et al., Membrane–bound Na, K–ATPase: Target Size and Radiation Inactivation Size of Some of Its Enzymatic Reactions, J. Biological Chemistry, 263:18063–18070 (1988) (Am. Soc. for Biochem. and Mol. Biol.).

Jensen, O. T. et al., Vertical Guided Bone–Graft Augmentation in a New Canin Mandibular Model, The Int'l Journal of Oral and Maxillofacial Implants, 10:335–343 (1995).

Jerosch, J. et al., A New Technique for Bone Sterilization, Biomed. Technik, 34:117–120 (1989).

Jerosch, J. et al., Influence of Different Rehydration Periods on the Stability and the Water Content of Bone Allografts After Lyophilization, Gamma–Irradiation, and Lipid Extraction. Z. Orthop., 132:335–341 (1994) (F. Enke Verlag Stuttgart).

Kamat, H.N. et al., Correlation of Structural Alterations in Bovine Fibrinogen with Loss of Clotting Properties After Gamma Irradiation, Radiation Research, 49:381–389 (1972) (Academic Press, Inc.).

Katz, R.W. et al., Radiation—Sterilized Insoluble Collagenous Bone Matrix is a Functional Carrier of Osteogenin for Bone Induction, Calcified Tissue Int., 47:183–185 (1990) (Springer–Verlag New York Inc.).

Keathly, J.D. et al., Is There Life After Irradiation? Part II: Gamma–Irradiated FBS in Cell Culture, BioPharm, (Jul.–Aug.) pp. 46, 50–52 (1993).

Kempner, E.S. et al., Effect of Environmental Conditions on Radiation Target Size Analyses, Analytical Biochemistry, 216:451–455 (1994).

Kempner, E.S. et al., Radiation–Damaged Tyrosinase Molecules are Inactive, Biophysical Journal, 55:159–162 (1989) (Biophysical Society).

Kempner, E.S. et al., Size Determination of Enzymes by Radiation Inactivation, Analytical Biochemistry, 92:2–10 (1979) (Academic Press, Inc.).

Kerboull, L. et al., In Vitro Study of the Influence of Various Conservation Methods on the Mechanical Properties of Patellar Tendon Allografts, Chirurgie, 117:751–762 (1991) (Masson, Paris).

Kitchen, A.D. et al., Effect of Gamma Irradiation on the Human Immunodeficiency Virus and Human Coagulation Proteins, Vox Sang, 56:223–229 (1989) (S. Karger AG, Basel).

Komender, A. et al., Some Biological Properties of Bovine Trypsinized Fascia Xenografts, Archivum Immunologiae et Therapiae Experimentalis, 29:485–489 (1981).

Komendar, A. et al., Some Biological Properties of Preserved Bovine Fascia Enriched With Pulverized Calf Cartilage, Archivum Immunologiae et Therapiae Experimentalis, 32:211–219 (1984).

Kouvalchouk, J.F. et al., The Use of Sterilized Bone Allografts in Reconstruction After Tumour Resection, Revue de Chirurgie Orthopédique 72:393–401 (1986) (Masson, Paris).

Kuijpers, A.J. et al., In vivo Compatibility and Degradation of Crosslinked Gelatin Gels Incorporated in Knitted Dacron, J. Biomed Mater Res., 51:136–145 (2000) (John Wiley & Sons, Inc.).

Latarjet, R. Inactivation of the Agents of Scrapie, Creutzfeldt–Jakob Disease, and Kuru by Radiations, Slow Transmissible Diseases of the Nervous System, 2:387–407 (1979) (Academic Press, Inc.) (New York).

Latarjet, R. et al., Inactivation of the Scrapie Agent by Near Monochromatic Ultraviolet Light, Nature, 227:1341–1343 (1970).

Lee, D.C. et al., A Direct Relationship Between the Partitioning of the Pathogenic Prion Protein and Transmissible Spongiform Encephalopathy Infectivity During the Purification of Plasma Proteins, Transfusion, 41:449–455 (2001).

Leitman, S. F. Use of Blood Cell Irradiation in the Prevention of Posttransfusion Graft–vs–Host Disease, Transfus. Sci., 10:219–232 (1989).

Le Maire, M. et al., Effects of Ionizing Radiations on Proteins, Journal of Biochem., 267:431–439 (1990).

License Amendment and Procedures for Gamma Irradiation of Blood Products, Dept. of Health & Human Services, Food and Drug Administration, pp. 1–18 (Jun. 22, 1993).

Linberg, J.V. et al., Preserved Irradiated Homologous Cartilage For Orbital Reconstruction, Ophthalmic Surgery, 11:457–462 (1980).

Lüssi–Schlatter, B. et al., Antimicrobial Treatment of Enzyme Preparations With Gamma Rays, Pharm Acta Helv, 49:66–75 (1974).

McDowell, S., Irradiated Cartilage, Plastic Surgical Nursing, pp. 14–15 (Spring 1988).

Ma, J.T. et al., Functional Size Analysis of F–ATPase from *Escherichia coli* by Radiation Inactivation, The Journal of Biological Chemistry, 268:10802–10807 (1993) (The Am. Soc. for Biochem. and Mol. Biol., Inc.).

Maedea, A. et al., Effects of Solvent Preservation With or Without Gamma Irradiation on the Material Properties of Canine Tendon Allografts, Journal of Orthopaedic Research, 11:181–189 (1993) (Orthopaedic Research Society).

Maeda, A. et al., Solvent–dried and Gamma–irradiated Tendon Allografts in Rats, The Journal of Bone and Joint Surgery, 80–B:731–736 (1998).

Malawski, S. et al., The Use of Dry–Freezed Bone Grafs Sterilized by Gamma Rays in Orthopaedic Surgery, Chir. Narz. Ruchu Ortop. Pol., 34:61–68 (1969).

Malm, J. R. et al., An Evaluation of Aortic Valve Homografts Sterilized by Electron Beam Energy, J. Thoracic and Cardiovascular Surgery, 54:471–477 (1967).

Malm, J.R. et al., Results of Aortic Valve Replacement Utilizing Irradiated Valve Homografts, Ann. N. Y. Acad. Sci., 147:740–747 (1969).

Martindale, The Extra Pharmacopoeia, Glucose, Twenty–ninth Edition, Glucose, p. 1265 (1989) (The Royal Pharmaceutical Society of Great Britain).

Marton, L.S. et al., Disinfection and Inactivation of the Human T. Lymphotropic Virus Type III/Lymphadenopathy–Associated Virus, The Journal of Infectious Diseases, 151:400–403 (1985).

Marx, G. Protecting Fibrinogen with Rutin During UVC Irradiation for Viral Inactivation, Photochemistry and Photobiology, 63:541–546 (1996) (American Society for Photobiology).

The Merck Index, Eleventh Edition, Glucose, pp. 699–700 (1989) (Merck & Co., Inc.).

Miekka, S.I. et al., New Methods for Inactivation of Lipid–enveloped and Non–enveloped Viruses, Haemophilia, 4:402–408 (1998) (Blackwell Science Ltd.).

Moore, G.L. et al., Effects of 4000 Rad. Irradiation on the In Vitro Storage Properties of Packed Red Cells, Final Rept., Pub. in Transfusion, 25:583–585 (1985) (Abstract).

Munting, E. et al., Effect of Sterilization on Osteoinduction, Acta Orthop. Scand., 59:34–38 (1988).

Nagrani, S. et al., The Radiation–Induced Inactivation of External Yeast Invertase in Dilute Aqueous Solution, Int. J. Radiat. Biol., 55:191–200 (1989) (Taylor & Francis Ltd.).

Nakata, K. et al, Reconstruction of the Lateral Ligaments of the Ankle Using Solvent–dried and Gamma–Irradiated Allogeneic Fascia Lata, The Journal of Bone & Joint Surgery, 82–B:579–582 (2000) (British Editorial Society of Bone and Joint Surgery).

Nielsen, M. et al., The Apparent Target Size of Rat Brain Benzodiazepine Receptor, Acetylcholinesyterase, and Pyruvate Kinase Is Highly Influenced by Experimental Conditions, The Journal of Biological Chemistry, 263:11900–11906 (1988) (The American Soceity for Biochemistry and Molecular Biology, Inc.).

Oh, W. et al., Mitral Valve Replacement With Preserved Cadaveric Aortic Homografts, J. Thoracic and Cardiovascular Surgery, 65:712–721 (1973).

Pardo, M.E.M. et al., Clinical Application of Amniotic Membranes on a Patient With Epidermolysis Bullosa, Annals of Transplantation, 4:68–73 (1999).

Parizek, J. et al., Duraplasty With Pretreated Freeze–dried Sterilized Human Dura Mater, Sbor. véd. Prací I.F UK Hrader. Králové., 33:135–143 (1990).

Parizek, J. et al., Ovine Pericardium: A New Material For Duraplasty, J. Neurosurg, 84:508–513 (1996).

Patel, K. M. et al., Effect of Gamma Radiation and Ethylene Oxide on Papain, Indian J. Pharm. Sci., 41:81–83 (1979) (The Indian Pharmaceutical Association).

Pietrucha, K. et al., New Collagen Implant As Dural Substitue, Biomaterials, 12:320–323 (1991) (Butterworth–Heinemann Ltd.).

Plavsic, Z. M. et al., Resistance of Porcine Circovirus to Gamma Irradation, BioPharm, pp. 32–34, 36 (Apr. 2001).

Polezhaev, L. V. et al., Repair of Cranial Defects With Regenerating Bone in Grafting Gamma–Irradiated Bone Filings, ZH Vopr Neifokhir Im N.N. Burdenko, (6):57–60 (1984).

Pollard, The Effect of Ionizing Radiation on Viruses, pp. 65–7, Chapter 4, prior art.

Potier, M. et al., Radiation Inactivation of Proteins: Temperature–dependent Inter–Protomeric Energy Transfer in Ox Liver Catalase, Biochem. J., 298:571–574 (1994).

Prolo, D.J. et al., Composite Autogeneic Human Cranioplasty: Frozen Skull Supplemented With Fresh Ilian Corticocancellous Boen, Neurosurgery, 15:846–851 (1984) (The Congress of Neurological Surgeons).

Prolo, D.J. et al., Superior Osteogenesis in Transplanted Allogeneic Canine Skull Following Chemical Sterilization, In Clinical Orthopaedics and Related Research; Section III: Basic Science and Pathology (168):230–242 (1982) (J.B. Lippincott Co.).

Puolakkainen, P.A. et al., The Effect of Sterilization on Transforming Growth Factor β Isolated From Demineralized Human Bone, Transfusion, 33:679–685 (1993).

Quaglio, E. et al., Copper Converts the Cellular Prion Protein into a Protease–resistant Species That Is Distinct from the Scrapie Isoform, J. Biological Chemistry, 276:11432–11438 (2001) (The American Society for Biochemistry and Molecular Biology, Inc.).

Raptopoulou–Gigi, M. et al., Antimicrobial Proteins in Sterilised Human Milk, British Medical Journal, 1:12–14 (1977).

Rasmussen T.J. et al., The Effects of 4 Mrad of γ Irradiation on the Initial Mechanical Properties of Bone–Patellar Tendon–Bone Grafts, Arthroscopy: J. Arthroscopic and Related Surgery, 10:188–197 (1994) (Raven Press, Ltd.).

Reid, B.D., The Sterways Process: A New Approach to Inactivating Viruses Using Gamma Radiation, Biologicals, 26:125–130 (1988) (The Int'l Assoc. of Biological Standardization).

Ripamonti, U. et al., Long–Term Evaluation of Bone Formation by Osteogenic Protein 1 in the Baboon and Relative Efficacy of Bone–Derived Bone Morphogenetic Proteins Delivered by Irradiated Xenogeneic Collagenous Matrices, J. Bone and Mineral Research, 15:1798–1809 (2000) (Am. Soc. for Bone and Mineral Res.).

Rittenhouse, E. A. et al., Sterilization of Aortic Valve Grafts for Transplantation, Archives of Surgery, 101:1–5 (1970).

Roe, S.C. et al., The Effect of Gamma Irradiation on Xenograft Tendon Bioprosthesis, Clinical Materials, 9:149–154 (1992) (Elsevier Science Publishers Ltd.).

Rohwer, R.G., Estimation of Scrapie Nucleic Acid MW from Standard Curves for Virus Sensitivity to Ionizing Radiation, Nature, 320:381 (1986) (Macmillan Journals Ltd.).

Rohwer, R.G., Scrapie Infectious Agent is Virus–like in Size and Susceptibility to Inactivation, Nature, 308:658–662 (1984).

Rohwer, R.G., The Scrapie Agent: "A Virus by Any Other Name", Current Topics in Microbiology and Immunology, 172:195–232 (1991).

Rohwer, R.G., et al., Scrapie–Virus of Viroid, The Case For a Virus, National Institutes of Neurological and Communicative Disorders and Stroke, NIH, pp. 333–355 (1980).

Rohwer, R.G., Virus–Like Sensitivity of the Scrapie Agent to Heat Inactivation, Science, 223:600–602 (1984) (American Association for the Advancement of Science).

Sakai, T. et al., Microbiological Studies on Drugs and Their Raw Materials. IV.[1] Sterlization of Microbial Contaminants in Enzyme Powder by Gamma Irradiation, Chem. Pharm. Bull., 26:1130–1134 (1978).

Salehpour, A. et al., Dose–Dependent Response of Gamma Irradiation on Mechanical Properties and Related Biochemical Composition of Goat Bone–Patellar Tendon–Bone Allografts, J. Orthopaedic Research, 13:898–906 (1995).

Salim,–Hanna, M. et al., Free Radical Scavenging Activity Of Carnosine, Free Rad. Res. Comms., 14:263–270 (1991) (Harwood Academic Publishers GmbH).

Sato, H. et al., Sterilization of Therapeutic Immunoadsorbents by Ionizing Radiation, The International Journal of Artificial Organs, 9:131–136 (1986).

Schwarz, N. et al., Irradiation–sterilization of Rat Bone Matrix Gelatin, Acta Orthop Scand, 59:165–167 (1988).

Shcheglova, S.G. et al., The Effect of the Power of Gamma–Radiation on the Radiation dose in the Sterilization of Drugs, Khim Fram ZH, 18:730–732 (1984) Derwent (Abstract) No. 111469.

Smith, C.W. et al., Mechanical Properties of Tendons: Changes With Sterilization and Preservation, J. Biomechanical Engineering, 118:56–61 (1996) (ASME).

Smith, R.A. et al., Gamma Irradiation of HIV–1, J. Orthopaedic Research, 19:815–819 (2001) (Elsevier Science Ltd.).

Song, K.B. et al., Effect of Gamma–irradiation on the Physiochemical Properties of Blood Plasma Proteins, 2002 Annual Meeting and Food Expo–Anaheim, California, Session 30C–1 Food and Chemistry: Proteins, (Jun. 2002) (Abstract).

Sullivan, R. et al., Inactivation of Thirty Viruses by Gamma Radiation, Applied Microbiology, 22:61–65 (1971) (American Society for Microbiology).

Sung, H. et al., Effects of Various Chemical Sterilization Methods on the Crosslinking and Enzymatic Degradation Characteristics of an Epoxy–Fixed Biological Tissue, Sterilization of Biological Tissues, J. Biomed. Mater. Res., 37:376–383 (1997) (John Wiley & Sons, Inc.).

Suomela, H., Inactivation of Viruses in Blood and Plasma Products, Transfusion Medicine Reviews, 7:42–57 (1993) (W.B. Saunders Company).

Toritsuka, Y. et al., Effect of Freeze–Drying or γ–Irradiation on Remodeling of Tendon Allograft in Rat Model, J. Orthopaedic Research, 15:294–300 (1997) (Orthopaedic Research Society).

Tylman, D., Mechanical Character of Liofilized and Sterilized by γ–Rays Bone Tissue, Chirurgia Narzadow Ruchu Ortop Pol, 31:229–234 (1966).

Vaida, R.I. et al., Structural–Functional Peculiarities of Myocardial Capillaries After Resecton of the Lungs, Arkn. Anat. Gistol. Embriol., 8:68–73 (1987).

Wangerin, K., et al., Behavior of Differently Sterilized Allogenic Lyophilized Cartilage Implants in Dogs, J. Oral Maxillofac Surg., 45:236–242 (1987).

Welch, W., A Comparative Study of Different Methods of Processing Aortic Homografts, Thorax, 24:746–749 (1969).

White, J.M. et al, Sterilization of Teeth by Gamma Radiation, J. Dent Res., 73:1560–1567 (1994).

Wientroub, S. et al., Influence of Irradiation on the Osteoinductive Potential of Demineralilzed Bone Matrix, Calcified Tissue International, 42:255–260 (1988) (Springer–Verlag New York Inc.).

Wong, B. et al., Copper Refolding of Prion Protein, Biochemical and Biophysical Research Communications, 276:1217–1224 (2000) (Academic Press).

Wong, B. et al., Differential Contribution of Superoxide Dismutase Activity by Prion Proteinin Vivo, Biochemical and Biophysical Research Communications, 273:136–139 (2000) (Academic Press).

Wong, B. et al. Prion Disease: A Loss of Antioxidant Function? Biochemical and Biophysical Research Communications, 275:249–252 (2000) (Academic Press).

Wyatt, D.E. et al., Is there Life After Irradiation? Part I: Inactivation of Biological Contaminants, BioPharm, pp. 34–39 (Jun. 1993).

Yarygina, G.A., Dose Rate Effect on Survival of Microorganisms Used As Test–Cultures in Radiation Sterilization of Medical Products, 9:32–39 (1973) (Radiats Tekh) Caplus Abstract No.2159557 (1973).

Zhang, Q. et al., Ethylene Oxide Does Not Extinguish the Osteoinductive Capacity of Demineralized Bone, Acta Orthop Scand, 68:104–108 (1997) (Scandinavian University Press).

Zhang, Y. et al., A Comprehensive Study of Physical Parameters, Biomechanical Properties and Statistical Correlations of Ilian Crest Bone Wedges Used in Spinal Fusion Surgery, Spine, 19:304–308 (1994) (J.B. Lippincott Co.).

(Abstract of EP0919198A2 and EP09191983A (Delphion-DERABS Abstract #G1999–304614)), prior art.

Website: www.wslfweb.org/docs/dstp2000.dtopdf/19–MD.pdf (Defense Science and Technology Plans, (Feb. 2000) p. 176, Section II, MD.03, U.S. Department of Defense Deputy Under Secretary of Defense (Science and Technology)).

Website: www.usacc.org/ataccc/ppt.html, (Advanced Technology Applications for Combat Casualty Care, 2001 Presentation, US Army Medical Research and Material Command Combat Casualty Care Research Program (2001)).

Website: www.usacc.org/RevisedStepB.html, Bakaltcheva, I. et al., (FY01 Request for Proposals–Intramural–Revised 2, Combat Casualty Care Research Program, (2002)).

Website: www.benvue.com/history/history_content.html, (2002).

Website: www.phase-technologies.com/html/vol.2no1.html, Jennings, T.A., (Glossary of Terms for Lyophilization) (1999).

Website: www.phase-technologies.com/html/vol.1no9.html, Jennings, T.A., (Overview of the Lyophilization Process) (1998).

Website: www.phase-technologies.com/html/vol.1no2.html, Jennings, T.A., (Role of Product Temperature in the Lyophilization Process) (1998).

Website: www.phase-technologies.com/html/vol.2no2.html, Jennings, T.A., (What I Wish I Knew About Lyophilization) (1999).

Website: www.phase-technologies.com/html/vol.1no7.html, Jennings, T.A., (Which Shelf Temperature During Lyophilization?) (1998).

Website: www.phase-technologies.com/html/vol.1no10.html, Jennings, T.A., (Yes, You have no Eutectic) (1998).

* cited by examiner

METHODS FOR STERILIZING BIOLOGICAL MATERIALS BY MULTIPLE RATES

This application is a continuation-in-part of U.S. application Ser. No. 09/973,958, filed Oct. 11, 2001, which is a continuation-in-part of PCT Application No. PCT/US01/09361, filed Mar. 23, 2001. The entire disclosure of these applications are hereby incorporated in their entirety.

BACKGROUND OF THE INVENTION

1. Field of the Invention

The present invention relates to methods for sterilizing biological materials to reduce the level of one or more biological contaminants or pathogens therein, such as viruses, bacteria (including inter- and intracellular bacteria, such as mycoplasmas, ureaplasmas, nanobacteria, chlamydia, rickettsias), yeasts, molds, fungi, single or multicellular parasites, and/or prions or similar agents responsible, alone or in combination, for TSEs.

2. Background of the Related Art

Many biological materials that are prepared for human, veterinary, diagnostic and/or experimental use may contain unwanted and potentially dangerous biological contaminants or pathogens, such as viruses, bacteria (including inter- and intracellular bacteria, such as mycoplasmas, ureaplasmas, nanobacteria, chlamydia, rickettsias), yeasts, molds, fungi, single or multicellular parasites, and/or prions or similar agents responsible, alone or in combination, for TSEs. Consequently, it is of utmost importance that any biological contaminant in the biological material be inactivated before the product is used. This is especially critical when the material is to be administered directly to a patient, for example in blood transfusions, blood factor replacement therapy, organ transplants and other forms of human therapy corrected or treated by intravenous, intramuscular or other forms of injection or introduction. This is also critical for the various biological materials that are prepared in media or via culture of cells or recombinant cells which contain various types of plasma and/or plasma derivatives or other biologic materials and which may contain prions, bacteria, viruses and other biological contaminants or pathogens.

Most procedures for producing biological materials have involved methods that screen or test the biological materials for one or more particular biological contaminants or pathogens rather than removal or inactivation of the contaminant(s) and/or pathogen(s) from the material. Materials that test positive for a biological contaminant or pathogen are merely not used. Examples of screening procedures include the testing for a particular virus in human blood from blood donors. Such procedures, however, are not always reliable and are not able to detect the presence of certain viruses, particularly in very low numbers. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the material is contaminated. Moreover, to date, there is no reliable test or assay for identifying prions within a biological material that is suitable for screening out potential donors or infected material. This serves to heighten the need for an effective means of destroying prions within a biological material, while still retaining the desired activity of that material. Therefore, it would be desirable to apply techniques that would kill or inactivate biological contaminants and pathogens during and/or after manufacturing the biological material.

The importance of these techniques is apparent regardless of the source of the biological material. All living cells and multi-cellular organisms can be infected with viruses and other pathogens. Thus the products of unicellular natural or recombinant organisms or tissues carry a risk of pathogen contamination. In addition to the risk that the producing cells or cell cultures may be infected, the processing of these and other biological materials creates opportunities for environmental contamination. The risks of infection are more apparent for multicellular natural and recombinant organisms, such as transgenic animals. Interestingly, even products from species as different from humans as transgenic plants carry risks, both due to processing contamination as described above, and from environmental contamination in the growing facilities, which may be contaminated by pathogens from the environment or infected organisms that co-inhabit the facility along with the desired plants. For example, a crop of transgenic corn grown out of doors, could be expected to be exposed to rodents such as mice during the growing season. Mice can harbour serious human pathogens such as the frequently fatal Hanta virus. Since these animals would be undetectable in the growing crop, viruses shed by the animals could be carried into the transgenic material at harvest. Indeed, such rodents are notoriously difficult to control, and may gain access to a crop during sowing, growth, harvest or storage. Likewise, contamination from overflying or perching birds has the potential to transmit such serious pathogens as the causative agent for psittacosis. Thus any biological material, regardless of its source, may harbour serious pathogens that must be removed or inactivated prior to the administration of the material to a recipient.

In conducting experiments to determine the ability of technologies to inactivate viruses, the actual viruses of concern are seldom utilized. This is a result of safety concerns for the workers conducting the tests, and the difficulty and expense associated with the containment facilities and waste disposal. In their place, model viruses of the same family and class are used.

In general, it is acknowledged that the most difficult viruses to inactivate are those with an outer shell made up of proteins, and that among these, the most difficult to inactivate are those of the smallest size. This has been shown to be true for gamma irradiation and most other forms of radiation as these viruses' diminutive size is associated with a small genome. The magnitude of direct effects of radiation upon a molecule are directly proportional to the size of the molecule, that is the larger the target molecule, the greater the effect. As a corollary, it has been shown for gamma-irradiation that the smaller the viral genome, the higher the radiation dose required to inactive it.

Among the viruses of concern for both human and animal-derived biological materials, the smallest, and thus most difficult to inactivate, belong to the family of Parvoviruses and the slightly larger protein-coated Hepatitis virus. In humans, the Parvovirus B19, and Hepatitis A are the agents of concern. In porcine-derived materials, the smallest corresponding virus is Porcine Parvovirus. Since this virus is harmless to humans, it is frequently chosen as a model virus for the human B19 Parvovirus. The demonstration of inactivation of this model parvovirus is considered adequate proof that the method employed will kill human B19 virus and Hepatitis A, and by extension, that it will also kill the larger and less hardy viruses such as HIV, CMV, Hepatitis B and C and others.

More recent efforts have focussed on methods to remove or inactivate contaminants in the products. Such methods include heat treating, filtration and the addition of chemical inactivants or sensitizers to the product.

Heat treatment requires that the product be heated to approximately 60° C. for about 70 hours which can be damaging to sensitive products. In some instances, heat inactivation can actually destroy 50% or more of the biological activity of the product.

Filtration involves filtering the product in order to physically remove contaminants. Unfortunately, this method may also remove products that have a high molecular weight. Further, in certain cases, small viruses may not be removed by the filter.

The procedure of chemical sensitization involves the addition of noxious agents which bind to the DNA/RNA of the virus and which are activated either by UV or other radiation. This radiation produces reactive intermediates and/or free radicals which bind to the DNA/RNA of the virus, break the chemical bonds in the backbone of the DNA/RNA, and/or cross-link or complex it in such a way that the virus can no longer replicate. This procedure requires that unbound sensitizer is washed from products since the sensitizers are toxic, if not mutagenic or carcinogenic, and cannot be administered to a patient.

Irradiating a product with gamma radiation is another method of sterilizing a product. Gamma radiation is effective in destroying viruses and bacteria when given in high total doses (Keathly et al., "Is There Life After Irradiation? Part 2," *BioPharm*, July–August, 1993, and Leitman, "Use of Blood Cell Irradiation in the Prevention of Post Transfusion Graft-vs-Host Disease," *Transfusion Science*, 10:219–239 (1989)). The published literature in this area, however, teaches that gamma radiation can be damaging to radiation sensitive products, such as blood, blood products, protein and protein-containing products. In particular, it has been shown that high radiation doses are injurious to red cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective". Unfortunately, many sensitive biological materials, such as monoclonal antibodies (Mab), may lose viability and activity if subjected to freezing for irradiation purposes and then thawing prior to administration to a patient.

In view of the difficulties discussed above, there remains a need for methods of sterilizing compositions containing one or more biological materials that are effective for reducing the level of active biological contaminants or pathogens without an adverse effect on the material(s).

The above references are incorporated by reference herein where appropriate for appropriate teachings of additional or alternative details, features and/or technical background.

SUMMARY OF THE INVENTION

An object of the invention is to solve at least the related art problems and disadvantages, and to provide at least the advantages described hereinafter.

Accordingly, it is an object of the present invention to provide methods of sterilizing biological materials by reducing the level of active biological contaminants or pathogens without adversely effecting the material. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof In accordance with these and other objects, a first embodiment of the present invention is directed to a method for sterilizing a biological material that is sensitive to radiation comprising irradiating the biological material with radiation for a time effective to sterilize the biological material at a rate effective to sterilize the biological material and to protect the biological material from radiation.

Another embodiment of the present invention is directed to a method for sterilizing a biological material that is sensitive to radiation comprising: i) applying to the biological material at least one stabilizing process selected from the group consisting of a) adding to said biological material at least one stabilizer in an amount effective to protect said biological material from said radiation; b) reducing the residual solvent content of said biological material to a level effective to protect said biological material from said radiation; c) reducing the temperature of said biological material to a level effective to protect said biological material from said radiation; d) reducing the oxygen content of said biological material to a level effective to protect said biological material from said radiation; e) adjusting the pH of said biological material to a level effective to protect said biological material from said radiation; and f) adding to said biological material at least one non-aqueous solvent in an amount effective to protect said biological material from said radiation; and ii) irradiating said biological material with a suitable radiation at an effective rate for a time effective to sterilize said biological material.

Another embodiment of the present invention is directed to a method for sterilizing a biological material that is sensitive to radiation, said method comprising: i) applying to the biological material at least one stabilizing process selected from the group consisting of: a) adding to the biological material at least one stabilizer; b) reducing the residual solvent content of the biological material; c) reducing the temperature of the biological material; d) reducing the oxygen content of the biological material; e) adjusting the pH of the biological material; and f) adding to the biological material at least one non-aqueous solvent; and ii) irradiating the biological material with a suitable radiation at an effective rate for a time effective to sterilize the biological material, wherein said at least one stabilizing process and the rate of irradiation are together effective to protect the biological material from the radiation.

Another embodiment of the present invention is directed to a method for sterilizing a biological material that is sensitive to radiation, said method comprising: i) applying to the biological material at least one stabilizing process selected from the group consisting of: a) adding to the biological material at least one stabilizer; b) reducing the residual solvent content of the biological material; c) reducing the temperature of the biological material; d) reducing the oxygen content of the biological material; e) adjusting the pH of the biological material; and f) adding to the biological material at least one non-aqueous solvent; and ii) irradiating the biological material with a suitable radiation at an effective rate for a time effective to sterilize the biological material, wherein said at least two stabilizing processes are together effective to protect the biological material from said radiation and further wherein said at least two stabilizing processes may be performed in any order.

Another embodiment of the present invention is directed to a composition comprising at least one biological material and at least one stabilizer in an amount effective to preserve the biological material for its intended use following sterilization with radiation.

Another embodiment of the present invention is directed to a composition comprising at least one biological material, wherein the residual solvent content of the biological material is at a level effective to preserve the biological material for its intended use following sterilization with radiation.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

DETAILED DESCRIPTION OF PREFERRED EMBODIMENTS

A. Definitions

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "biological material" is intended to mean any substance derived or obtained from a living organism. Illustrative examples of biological materials include, but are not limited to, the following: cells; tissues; blood or blood components; proteins, including recombinant and transgenic proteins, and proteinaceous materials; enzymes, including digestive enzymes, such as trypsin, chymotrypsin, alpha-glucosidase and iduronodate-2-sulfatase; immunoglobulins, including mono and polyimmunoglobulins; botanicals; food; and the like. Preferred examples of biological materials include, but are not limited to, the following: ligaments; tendons; nerves; bone, including demineralized bone matrix, grafts, joints, femurs, femoral heads, etc.; teeth; skin grafts; bone marrow, including bone marrow cell suspensions, whole or processed; heart valves; cartilage; corneas; arteries and veins; organs, including organs for transplantation, such as hearts, livers, lungs, kidneys, intestines, pancreas, limbs and digits; lipids; carbohydrates; collagen, including native, afibrillar, atelomeric, soluble and insoluble, recombinant and transgenic, both native sequence and modified; enzymes; chitin and its derivatives, including NO-carboxy chitosan (NOCC); stem cells, islet of Langerhans cells and other cells for transplantation, including genetically altered cells; red blood cells; white blood cells, including monocytes; and platelets.

As used herein, the term "sterilize" is intended to mean a reduction in the level of at least one active or potentially active biological contaminant or pathogen found in the biological material being treated according to the present invention.

As used herein, the term "biological contaminant or pathogen" is intended to mean a contaminant or pathogen that, upon direct or indirect contact with a biological material, may have a deleterious effect on a biological material or upon a recipient thereof. Such biological contaminants or pathogens include the various viruses, bacteria (including inter- and intracellular bacteria, such as mycoplasmas, ureaplasmas, nanobacteria, chlamydia, rickettsias), yeasts, molds, fungi, single or multicellular parasites, and/or prions or similar agents responsible, alone or in combination, for TSEs known to those of skill in the art to generally be found in or infect biological materials. Examples of biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C and variants thereof), pox viruses, toga viruses, Epstein-Barr viruses and parvoviruses; bacteria (including mycoplasmas, ureaplasmas, nanobacteria, chlamydia, rickettsias), such as Escherichia, Bacillus, Campylobacter, Streptococcus and Staphylococcus; parasites, such as Trypanosoma and malarial parasites, including Plasmodium species; yeasts; molds; and prions, or similar agents, responsible alone or in combination for TSE (transmissible spongiform encephalopathies), such as scrapie, kuru, BSE (bovine spongiform encephalopathy), CJD (Creutzfeldt-Jakob disease), Gerstmann-Straeussler-Scheinkler syndrome, and fatal familial insomnia. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in the biological material and/or a recipient thereof.

As used herein, the term "blood components" is intended to mean one or more of the components that may be separated from whole blood and include, but are not limited to, the following: cellular blood components, such as red blood cells, white blood cells, and platelets; blood proteins, such as blood clotting factors, enzymes, albumin, plasminogen, fibrinogen, and immunoglobulins; and liquid blood components, such as plasma, plasma protein fraction (PPF), cryoprecipitate, plasma fractions, and plasma-containing compositions.

As used herein, the term "cellular blood component" is intended to mean one or more of the components of whole blood that comprises cells, such as red blood cells, white blood cells, stem cells, and platelets.

As used herein, the term "blood protein" is intended to mean one or more of the proteins that are normally found in whole blood. Illustrative examples of blood proteins found in mammals, including humans, include, but are not limited to, the following: coagulation proteins, both vitamin K-dependent, such as Factor VII and Factor IX, and non-vitamin K-dependent, such as Factor VIII and von Willebrands factor; albumin; lipoproteins, including high density lipoproteins (HDL), low density lipoproteins (LDL), and very low density lipoproteins (VLDL); complement proteins; globulins, such as immunoglobulins IgA, IgM, IgG and IgE; and the like. A preferred group of blood proteins includes Factor I (fibrinogen), Factor II (prothrombin), Factor III (tissue factor), Factor V (proaccelerin), Factor VI (accelerin), Factor VII (proconvertin, serum prothrombin conversion), Factor VIII (antihemophiliac factor A), Factor IX (antihemophiliac factor B), Factor X (Stuart-Prower factor), Factor XI (plasma thromboplastin antecedent), Factor XII (Hageman factor), Factor XIII (protransglutamidase), von Willebrands factor (vWF), Factor Ia, Factor Ia, Factor IIIa, Factor Va, Factor VIa, Factor VIIa, Factor VIIIa, Factor IXa, Factor Xa, Factor XIa, Factor XIIa, and Factor XIIIa. Another preferred group of blood proteins includes proteins found inside red blood cells, such as hemoglobin and various growth factors, and derivatives of these proteins.

As used herein, the term "liquid blood component" is intended to mean one or more of the fluid, non-cellular components of whole blood, such as plasma (the fluid, non-cellular portion of the whole blood of humans or animals as found prior to coagulation) and serum (the fluid, non-cellular portion of the whole blood of humans or animals as found after coagulation).

As used herein, the term "a biologically compatible solution" is intended to mean a solution to which a biological material may be exposed, such as by being suspended or dissolved therein, and remain viable, i.e., retain its essential biological, pharmacological, and physiological characteristics.

As used herein, the term "a biologically compatible buffered solution" is intended to mean a biologically compatible solution having a pH and osmotic properties (e.g., tonicity, osmolality, and/or oncotic pressure) suitable for maintaining the integrity of the material(s) therein, including suitable for maintaining essential biological, pharmacological, and physiological characteristics of the material(s) therein. Suitable biologically compatible buffered solutions typically have a pH between about 2 and about 8.5, and are isotonic or only moderately hypotonic or hypertonic. Biologically compatible buffered solutions are known and readily available to those of skill in the art.

As used herein, the term "stabilizer" is intended to mean a compound or material that, alone and/or in combination, reduces damage to the biological material being irradiated to a level that is insufficient to preclude the safe and effective use of the material. Illustrative examples of stabilizers that are suitable for use include, but are not limited to, the following, including structural analogs and derivatives thereof: antioxidants; free radical scavengers, including spin traps, such as tert-butyl-nitrosobutane (tNB), α-phenyl-tert-butylnitrone (PBN), 5,5-dimethylpyrroline-N-oxide (DMPO), tert-butylnitrosobenzene (BNB), α-(4-pyridyl-1-oxide)-N-tert-butylnitrone (4-POBN) and 3,5-dibromo-4-nitroso-benzenesulphonic acid (DBNBS); combination stabilizers, i.e., stabilizers which are effective at quenching both Type I and Type II photodynamic reactions; and ligands, ligand analogs, substrates, substrate analogs, modulators, modulator analogs, stereoisomers, inhibitors, and inhibitor analogs, such as heparin, that stabilize the molecule(s) to which they bind. Preferred examples of additional stabilizers include, but are not limited to, the following: fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tetranor-dihydrolipoic acid, omega-3 fatty acids, omega-6 fatty acids, omega-9 fatty acids, furan fatty acids, oleic, linoleic, linolenic, arachidonic, eicosapentaenoic (EPA), docosahexaenoic (DHA), and palmitic acids and their salts and derivatives; carotenes, including alpha-, beta-, and gamma-carotenes; Co-Q10; xanthophylls; sucrose, polyhydric alcohols, such as glycerol, mannitol, inositol, and sorbitol; sugars, including derivatives and stereoisomers thereof, such as xylose, glucose, ribose, mannose, fructose, erythrose, threose, idose, arabinose, lyxose, galactose, allose, altrose, gulose, talose, and trehalose; amino acids and derivatives thereof, including both D- and L-forms and mixtures thereof, such as arginine, lysine, alanine, valine, leucine, isoleucine, proline, phenylalanine, glycine, serine, threonine, tyrosine, asparagine, glutamine, aspartic acid, histidine, N-acetylcysteine (NAC), glutamic acid, tryptophan, sodium capryl N-acetyl tryptophan, and methionine; azides, such as sodium azide; enzymes, such as Superoxide Dismutase (SOD), Catalase, and A4, A5 and A6 desaturases; uric acid and its derivatives, such as 1,3-dimethyluric acid and dimethylthiourea; allopurinol; thiols, such as glutathione and reduced glutathione and cysteine; trace elements, such as selenium, chromium, and boron; vitamins, including their precursors and derivatives, such as vitamin A, vitamin C (including its derivatives and salts such as sodium ascorbate and palmitoyl ascorbic acid) and vitamin E (and its derivatives and salts such as alpha-, beta-, gamma-, delta-, epsilon-, zeta-, and eta-tocopherols, tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4,5-diol; reducing substances, such as butylated hydroxyanisole (BHA) and butylated hydroxytoluene (BHT); cholesterol, including derivatives and its various oxidized and reduced forms thereof, such as low density lipoprotein (LDL), high density lipoprotein (HDL), and very low density lipoprotein (VLDL); probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); proteins, such as albumin, and peptides of two or more amino acids, any of which may be either naturally occurring amino acids, i.e., L-amino acids, or non-naturally occurring amino acids, i.e., D-amino acids, and mixtures, derivatives, and analogs thereof, including, but not limited to, arginine, lysine, alanine, valine, leucine, isoleucine, proline, phenylalanine, glycine, histidine, glutamic acid, tryptophan (Trp), serine, threonine, tyrosine, asparagine, glutamine, aspartic acid, cysteine, methionine, and derivatives thereof, such as N-acetylcysteine (NAC) and sodium capryl N-acetyl tryptophan, as well as homologous dipeptide stabilizers (composed of two identical amino acids), including such naturally occurring amino acids, as Gly—Gly (glycylglycine) and Trp—Trp, and heterologous dipeptide stabilizers (composed of different amino acids), such as carnosine (β-alanyl-histidine), anserine (β-alanyl-methylhistidine), and Gly-Trp; and flavonoids/flavonols, such as diosmin, quercetin, rutin, silybin, silidianin, silicristin, silymarin, apigenin, apiin, chrysin, morin, isoflavone, flavoxate, gossypetin, myricetin, biacalein, kaempferol, curcumin, proanthocyanidin B2-3-O-gallate, epicatechin gallate, epigallocatechin gallate, epigallocatechin, gallic acid, epicatechin, dihydroquercetin, quercetin chalcone, 4,4'-dihydroxy-chalcone, isoliquiritigenin, phloretin, coumestrol, 4',7-dihydroxy-flavanone, 4',5-dihydroxy-flavone, 4',6-dihydroxy-flavone, luteolin, galangin, equol, biochanin A, daidzein, formononetin, genistein, amentoflavone, bilobetin, taxifolin, delphinidin, malvidin, petunidin, pelargonidin, malonylapiin, pinosylvin, 3-methoxyapigenin, leucodelphinidin, dihydrokaempferol, apigenin 7-O-glucoside, pycnogenol, aminoflavone, purpurogallin fisetin, 2',3'-dihydroxyflavone, 3-hydroxyflavone, 3',4'-dihydroxyflavone, catechin, 7-flavonoxyacetic acid ethyl ester, catechin, hesperidin, and naringin. Particularly preferred examples include single stabilizers or combinations of stabilizers that are effective at quenching both Type I and Type II photodynamic reactions, and volatile stabilizers, which can be applied as a gas and/or easily removed by evaporation, low pressure, and similar methods.

As used herein, the term "residual solvent content" is intended to mean the amount or proportion of freely-available liquid in the biological material. Freely-available liquid means the liquid, such as water or an organic solvent (e.g., ethanol, isopropanol, polyethylene glycol, etc.), present in the biological material being sterilized that is not bound to or complexed with one or more of the non-liquid components of the biological material. Freely-available liquid includes intracellular water. The residual solvent contents related as water referenced herein refer to levels determined by the FDA approved, modified Karl Fischer method (Meyer and Boyd, Analytical Chem., 31:215–219, 1959; May, et al., *J. Biol. Standardization,* 10:249–259, 1982; Centers for Biologics Evaluation and Research, FDA, Docket No. 89D-0140, 83–93; 1990) or by near infrared spectroscopy. Quantitation of the residual levels of other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viruses, bacteria (including inter- and intracellular bacteria, such as mycoplasmas, ureaplasmas, nanobacteria, chlamydia, rickettsias), yeasts, molds, fungi, single or multicellular parasites, and/or prions or similar agents responsible, alone or in combination, for TSEs, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactines and their derivatives and analogs; angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphyrins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide. In addition, atoms which bind to prions, and thereby increase their sensitivity to inactivation by radiation, may also be used. An illustrative example of such an atom would be the Copper ion, which binds to the prion protein and, with a Z number higher than the other atoms in the protein, increases the probability that the prion protein will absorb energy during irradiation, particularly gamma irradiation.

As used herein, the term "proteinaceous material" is intended to mean any material derived or obtained from a living organism that comprises at least one protein or peptide. A proteinaceous material may be a naturally occurring material, either in its native state or following processing/purification and/or derivatization, or an artificially produced material, produced by chemical synthesis or recombinant/transgenic technology and, optionally, process/ purified and/or derivatized. Illustrative examples of proteinaceous materials include, but are not limited to, the following: proteins and peptides produced from cell culture; milk and other dairy products; ascites; hormones; growth factors; materials, including pharmaceuticals, extracted or isolated from animal tissue or plant matter, such as insulin; plasma, including fresh, frozen and freeze-dried, and plasma protein fraction; fibrinogen and derivatives thereof, fibrin, fibrin I, fibrin II, soluble fibrin and fibrin monomer, and/or fibrin sealant products; whole blood; protein C; protein S; alpha-1 anti-trypsin (alpha-1 protease inhibitor); butylcholinesterase; anticoagulants; streptokinase; tissue plasminogen activator (tPA); erythropoietin (EPO); urokinase; Neupogen™; anti-thrombin-3; alpha-galactosidase; iduronate-2-sulfatase; (fetal) bovine serum/horse serum; meat; immunoglobulins, including anti-sera, monoclonal antibodies, polyclonal antibodies, and genetically engineered or produced antibodies; albumin; alpha-globulins; beta-globulins; gamma-globulins; coagulation proteins; complement proteins; and interferons.

As used herein, the term "radiation" is intended to mean radiation of sufficient energy to sterilize at least some component of the irradiated biological material. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves. Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "E-beam" irradiation that involves their production via a machine. Visible light, both mono- and polychromatic, is produced by machines and may, in practice, be combined with invisible light, such as infrared and UV, that is produced by the same machine or a different machine.

As used herein, the term "to protect" is intended to mean to reduce any damage to the biological material being irradiated, that would otherwise result from the irradiation of that material, to a level that is insufficient to preclude the safe and effective use of the material following irradiation. In other words, a substance or process "protects" a biological material from radiation if the presence of that substance or carrying out that process results in less damage to the material from irradiation than in the absence of that substance or process. Thus, a biological material may be used safely and effectively after irradiation in the presence of a substance or following performance of a process that "protects" the material, but could not be used safely and effectively after irradiation under identical conditions but in the absence of that substance or the performance of that process.

As used herein, an "acceptable level" of damage may vary depending upon certain features of the particular method(s) of the present invention being employed, such as the nature and characteristics of the particular biological material and/ or non-aqueous solvent(s) being used, and/or the intended use of the biological material being irradiated, and can be determined empirically by one skilled in the art. An "unacceptable level" of damage would therefore be a level of damage that would preclude the safe and effective use of the biological material being sterilized. The particular level of damage in a given biological material may be determined using any of the methods and techniques known to one skilled in the art.

B. Particularly Preferred Embodiments

A first preferred embodiment of the present invention is directed to a method for sterilizing a biological material that is sensitive to radiation comprising irradiating the biological material with radiation for a time effective to sterilize the biological material at a rate effective to sterilize the biological material and to protect the biological material from radiation.

A second preferred embodiment of the present invention is directed to a method for sterilizing a biological material that is sensitive to radiation comprising: i) applying to the biological material at least one stabilizing process selected from the group consisting of a) adding to said biological material at least one stabilizer in an amount effective to protect said biological material from said radiation; b) reducing the residual solvent content of said biological material to a level effective to protect said biological material from said radiation; c) reducing the temperature of said biological material to a level effective to protect said biological material from said radiation; d) reducing the oxygen content of said biological material to a level effective to protect said biological material from said radiation; e) adjusting the pH of said biological material to a level effective to protect said biological material from said radiation; and f) adding to said biological material at least one non-aqueous solvent in an amount effective to protect said biological material from said radiation; and ii) irradiating said biological material with a suitable radiation at an effective rate for a time effective to sterilize said biological material.

A third preferred embodiment of the present invention is directed to a method for sterilizing a biological material that is sensitive to radiation, said method comprising: i) applying to the biological material at least one stabilizing process selected from the group consisting of: a) adding to the biological material at least one stabilizer; b) reducing the residual solvent content of the biological material; c) reducing the temperature of the biological material; d) reducing the oxygen content of the biological material; e) adjusting the pH of the biological material; and f) adding to the biological material at least one non-aqueous solvent; and ii) irradiating the biological material with a suitable radiation at an effective rate for a time effective to sterilize the biological material, wherein said at least one stabilizing process and the rate of irradiation are together effective to protect the biological material from the radiation.

A fourth preferred embodiment of the present invention is directed to a method for sterilizing a biological material that is sensitive to radiation, said method comprising: i) applying to the biological material at least one stabilizing process selected from the group consisting of: a) adding to the biological material at least one stabilizer; b) reducing the residual solvent content of the biological material; c) reducing the temperature of the biological material; d) reducing the oxygen content of the biological material; e) adjusting the pH of the biological material; and f) adding to the biological material at least one non-aqueous solvent; and ii) irradiating the biological material with a suitable radiation at an effective rate for a time effective to sterilize the biological material, wherein said at least two stabilizing processes are together effective to protect the biological material from said radiation and further wherein said at least two stabilizing processes may be performed in any order.

According to certain methods of the present invention, a stabilizer, or mixture of stabilizers, is added prior to irradiation of the biological material with radiation. This stabilizer is preferably added to the biological material in an amount that is effective to protect the biological material from the radiation. Suitable amounts of stabilizer may vary depending upon certain features of the particular method(s) of the present invention being employed, such as the particular stabilizer being used and/or the nature and characteristics of the particular biological material being irradiated and/or its intended use, and can be determined empirically by one skilled in the art.

According to certain methods of the present invention, the residual solvent content of the biological material is reduced prior to irradiation of the biological material with radiation. The residual solvent content is preferably reduced to a level that is effective to protect the biological material from the radiation. Suitable levels of residual solvent content may vary depending upon certain features of the particular method(s) of the present invention being employed, such as the nature and characteristics of the particular biological material being irradiated and/or its intended use, and can be determined empirically by one skilled in the art. There may be biological materials for which it is desirable to maintain the residual solvent content to within a particular range, rather than a specific value.

When the solvent is water, and particularly when the biological material is in a solid phase, the residual solvent content is generally less than about 15%, typically less than about 10%, more typically less than about 9%, even more typically less than about 8%, usually less than about 5%, preferably less than about 3.0%, more preferably less than about 2.0%, even more preferably less than about 1.0%, still more preferably less than about 0.5%, still even more preferably less than about 0.2% and most preferably less than about 0.08%.

The solvent may preferably be a non-aqueous solvent, more preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In certain embodiments of the present invention, the solvent may be a mixture of water and a non-aqueous solvent or solvents, such as ethanol and/or acetone. In such embodiments, the non-aqueous solvent(s) is preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In a preferred embodiment, when the residual solvent is water, the residual solvent content of a biological material is reduced by dissolving or suspending the biological material in a non-aqueous solvent that is capable of dissolving water.

Preferably, such a non-aqueous solvent is not prone to the formation of free-radicals upon irradiation and has little or no dissolved oxygen or other gas(es) that is (are) prone to the formation of free-radicals upon irradiation.

When the biological material is in a liquid phase, reducing the residual solvent content may be accomplished by any of a number of means, such as by increasing the solute concentration. In this manner, the concentration of protein in the biological material dissolved within the solvent may be increased to generally at least about 0.5%, typically at least about 1%, usually at least about 5%, preferably at least about 10%, more preferably at least about 15%, even more preferably at least about 20%, still even more preferably at least about 25%, and most preferably at least about 50%.

In certain embodiments of the present invention, the residual solvent content of a particular biological material may be found to lie within a range, rather than at a specific point. Such a range for the preferred residual solvent content of a particular biological material may be determined empirically by one skilled in the art.

While not wishing to be bound by any theory of operability, it is believed that the reduction in residual solvent content reduces the degrees of freedom of the biological material, reduces the number of targets for free radical generation and may restrict the solubility of these free radicals. Similar results might therefore be achieved by lowering the temperature of the biological material below its eutectic point or below its freezing point, or by vitrification to likewise reduce the degrees of freedom of the biological material. These results may permit the use of a higher rate and/or dose of radiation than might otherwise be acceptable. Thus, the methods described herein may be performed at any temperature that doesn't result in unacceptable damage to the biological material, i.e., damage that would preclude the safe and effective use of the biological material. Preferably, the methods described herein are performed at ambient temperature or below ambient temperature, such as below the eutectic point or freezing point of the biological material being irradiated.

The residual solvent content of the biological material may be reduced by any of the methods and techniques known to those skilled in the art for reducing solvent from a biological material without producing an unacceptable level of damage to the biological material. Preferred examples of such methods include, but are not limited to, lyophilization, evaporation, concentration, centrifugal concentration, vitrification, spray-drying, distillation, freeze-distillation and partitioning during and/or following lyophilization.

A particularly preferred method for reducing the residual solvent content of a biological material is lyophilization.

Another particularly preferred method for reducing the residual solvent content of a biological material is spray-drying.

Another particularly preferred method for reducing the residual solvent content of a biological material is vitrification, which may be accomplished by any of the methods and techniques known to those skilled in the art, including the addition of solute and or additional solutes, such as sucrose, to raise the eutectic point of the biological material, followed by a gradual application of reduced pressure to the biological material in order to remove the residual solvent, such as water. The resulting glassy material will then have a reduced residual solvent content.

According to certain methods of the present invention, the biological material to be sterilized may be immobilized upon a solid surface by any means known and available to one skilled in the art. For example, the biological material to be sterilized may be present as a coating or surface on a biological or non-biological substrate.

The radiation employed in the methods of the present invention may be any radiation effective for the sterilization of the biological material being treated. The radiation may be corpuscular, including E-beam radiation. Preferably the radiation is electromagnetic radiation, including x-rays, infrared, visible light, UV light and mixtures of various wavelengths of electromagnetic radiation. A particularly preferred form of radiation is gamma radiation.

According to the methods of the present invention, the biological material is irradiated with the radiation at a rate effective for the sterilization of the biological material, while not producing an unacceptable level of damage to that material. Suitable rates of irradiation may vary depending upon certain features of the methods of the present invention being employed, such as the nature and characteristics of the particular biological material being irradiated, the particular form of radiation involved and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to the methods of the present invention, the rate of irradiation may be optimized to produce the most advantageous combination of product recovery and time required to complete the operation. Both low (<3 kGy/hour) and high (>3 kGy/hour) rates may be utilized in the methods described herein to achieve such results. The rate of irradiation is preferably be selected to optimize the recovery of the biological material while still sterilizing the biological material. Although reducing the rate of irradiation may serve to decrease damage to the biological material, it will also result in longer irradiation times being required to achieve a particular desired total dose. A higher dose rate may therefore be preferred in certain circumstances, such as to minimize logistical issues and costs, and may be possible when used in accordance with the methods described herein for protecting a biological material from irradiation.

According to a particularly preferred embodiment of the present invention, the rate of irradiation is not more than about 3.0 kGy/hour, more preferably between about 0.1 kGy/hr and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr, more preferably at least about 6 kGy/hr, even more preferably at least about 16 kGy/hr, and even more preferably at least about 30 kGy/hr and most preferably at least about 45 kGy/hr or greater.

According to another particularly preferred embodiment of the present invention, the maximum acceptable rate of irradiation is inversely proportional to the molecular mass of the biological material being irradiated.

According to the methods of the present invention, the biological material to be sterilized is irradiated with the radiation for a time effective for the sterilization of the biological material. Combined with irradiation rate, the appropriate irradiation time results in the appropriate dose of irradiation being applied to the biological material. Suitable irradiation times may vary depending upon the particular form and rate of radiation involved and/or the nature and characteristics of the particular biological material being irradiated. Suitable irradiation times can be determined empirically by one skilled in the art.

According to the methods of the present invention, the biological material to be sterilized is irradiated with radiation up to a total dose effective for the sterilization of the biological material, while not producing an unacceptable level of damage to that material. Suitable total doses of radiation may vary depending upon certain features of the methods of the present invention being employed, such as the nature and characteristics of the particular biological material being irradiated, the particular form of radiation involved and/or the particular biological contaminants or pathogens being inactivated. Suitable total doses of radiation can be determined empirically by one skilled in the art. Preferably, the total dose of radiation is at least 25 kGy, more preferably at least 45 kGy, even more preferably at least 75 kGy, and still more preferably at least 100 kGy or greater, such as 150 kGy or 200 kGy or greater.

The particular geometry of the biological material being irradiated, such as the thickness and distance from the source of radiation, may be determined empirically by one skilled in the art. A preferred embodiment is a geometry that provides for an even rate of irradiation throughout the material. A particularly preferred embodiment is a geometry that results in a short path length for the radiation through the material, thus minimizing the differences in radiation dose between the front and back of the material or at its edges and center, if it or the radiation source is rotated. This may be further minimized in some preferred geometries, particularly those wherein the material has a constant radius about its axis that is perpendicular to the radiation source, by the utilization of a means of rotating the preparation about said axis. Similarly, there may be preferred geometries of the radiation source that may be determined empirically by one skilled in the art.

Similarly, according to certain methods of the present invention, an effective package for containing the biological material during irradiation is one which combines stability under the influence of irradiation, and which minimizes the interactions between the package and the radiation. Preferred packages maintain a seal against the external environment before, during and post-irradiation, and are not reactive with the biological material within, nor do they produce chemicals that may interact with the material within. Particularly preferred examples include but are not limited to containers that comprise glasses stable when irradiated, stoppered with stoppers made of rubber that is relatively stable during radiation and liberates a minimal amount of compounds from within, and sealed with metal crimp seals of aluminum or other suitable materials with relatively low Z numbers. Suitable materials can be determined by measuring their physical performance, and the amount and type of reactive leachable compounds post-irradiation and by examining other characteristics known to be important to the containment of biological materials empirically by one skilled in the art.

According to certain methods of the present invention, an effective amount of at least one sensitizing compound may optionally be added to the biological material prior to irradiation, for example to enhance the effect of the irradiation on the biological contaminant(s) or pathogen(s) therein, while employing the methods described herein to minimize the deleterious effects of irradiation upon the biological material. Suitable sensitizers are known to those skilled in the art, and include psoralens and their derivatives and inactines and their derivatives.

According to the methods of the present invention, the irradiation of the biological material may occur at any temperature that is not deleterious to the biological material being sterilized. According to one preferred embodiment, the biological material is irradiated at ambient temperature. According to an alternate preferred embodiment, the biological material is irradiated at reduced temperature, i.e. a temperature below ambient temperature or lower, such as 0° C., −20° C., −40° C., −60° C., −78° C. or −196° C. According to this embodiment of the present invention, the biological material is preferably irradiated at or below the freezing or eutectic point of the biological material. According to another alternate preferred embodiment, the biological material is irradiated at elevated temperature, i.e. a temperature above ambient temperature or higher, such as 37° C., 60° C., 72° C. or 80° C. While not wishing to be bound by any theory, the use of elevated temperature may enhance the effect of irradiation on the biological contaminant(s) or pathogen(s) and therefore allow the use of a lower total dose of radiation.

Most preferably, the irradiation of the biological material occurs at a temperature that protects the material from radiation. Suitable temperatures can be determined empirically by one skilled in the art.

In certain embodiments of the present invention, the temperature at which irradiation is performed may be found to lie within a range, rather than at a specific point. Such a range for the preferred temperature for the irradiation of a particular biological material may be determined empirically by one skilled in the art.

In a preferred embodiment, the rate of cooling may be optimized by one skilled in the art to minimize damage to the biological material prior to, during or following irradiation. In a more preferred embodiment the freezing and/or lyophylization process may be optimized so as to produce a partitioning of the component(s) of the biological mixture. In a more preferred embodiment, the desired component(s) of the mixture may be separated from the solvent, resulting in an effective increase in their concentration and reducing the damage done by reactive molecules produced by the irradiation of the solvent or other component(s) of the biological mixture. In another preferred embodiment, one or more stabilizer(s) in the biological mixture will also be partitioned with the desired component(s) of the biological mixture, thus enhancing the protection they afford and/or permitting a lower concentration of the stabilizer(s) to be employed. In an even more preferred embodiment, the stabilizer(s) within the biological mixture will also be partitioned with the desired component(s) of the biological mixture while the desired component(s) of the mixture, including the stabilizer(s), may be separated from the solvent, producing still less damage during irradiation.

According to another preferred embodiment, the material to be irradiated may be shielded from radiation other than that desired to sterilize the product in order to minimize the deleterious effects upon the biological material and/or any added stabilizer(s) by undesired radiation.

According to the methods of the present invention, the irradiation of the biological material may occur at any pressure which is not deleterious to the biological material being sterilized. According to one preferred embodiment, the biological material is irradiated at elevated pressure. More preferably, the biological material is irradiated at elevated pressure due to the application of sound waves or the use of a volatile. While not wishing to be bound by any theory, the use of elevated pressure may enhance the effect of irradiation on the biological contaminant(s) or pathogen (s) and/or enhance the protection afforded by one or more stabilizers, and therefore allow the use of a lower total dose of radiation. Suitable pressures can be determined empirically by one skilled in the art.

Generally, according to the methods of the present invention, the pH of the biological material undergoing sterilization is about 7. In some embodiments of the present invention, however, the biological material may have a pH of less than 7, preferably less than or equal to 6, more preferably less than or equal to 5, even more preferably less than or equal to 4, and most preferably less than or equal to 3. In alternative embodiments of the present invention, the biological material may have a pH of greater than 7, preferably greater than or equal to 8, more preferably greater than or equal to 9, even more preferably greater than or equal to 10, and most preferably greater than or equal to 11. According to certain embodiments of the present invention, the pH of the material undergoing sterilization is at or near the isoelectric point(s) of one or more of the components of the biological material. Suitable pH levels can be determined empirically by one skilled in the art.

Similarly, according to the methods of the present invention, the irradiation of the biological material may occur under any atmosphere that is not deleterious to the biological material being treated. According to one preferred embodiment, the biological material is held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the biological material is held under vacuum while being irradiated. According to a particularly preferred embodiment of the present invention, a biological material (lyophilized, liquid or frozen) is stored under vacuum or an inert atmosphere (preferably a noble gas, such as helium or argon, more preferably a higher molecular weight noble gas, and most preferably argon) prior to irradiation. According to an alternative preferred embodiment of the present invention, a liquid biological material is held under low pressure, to decrease the amount of gas, particularly oxygen, dissolved in the liquid, prior to irradiation, either with or without a prior step of solvent reduction, such as lyophilization. Such degassing may be performed using any of the methods known to one skilled in the art.

In another preferred embodiment, where the biological material contains oxygen or other gases dissolved within or associated with it, the amount of these gases within or associated with the material may be reduced by any of the methods and techniques known and available to those skilled in the art, such as the controlled reduction of pressure within a container (rigid or flexible) holding the material to be treated or by placing the material in a container of approximately equal volume.

In certain embodiments of the present invention, when the biological material to be treated is a tissue, the stabilizer is introduced according to any of the methods and techniques known and available to one skilled in the art, including soaking the tissue in a solution containing the stabilizer, preferably under pressure, at elevated temperature and/or in the presence of a penetration enhancer, such as dimethylsulfoxide. Other methods of introducing the stabilizer(s) into a tissue include, but are not limited to, applying a gas containing the stabilizer(s), preferably under pressure and/or at elevated temperature, injection of the stabilizer(s) or a solution containing the stabilizer(s) directly into the tissue, placing the tissue under reduced pressure and then introducing a gas or solution containing the stabilizer(s), dehydration of the tissue by means known to those skilled in the art, followed by re-hydration using a solution containing said stabilizer(s), and followed after irradiation, when desired, by subsequent dehydration with or without an additional re-hydration in a solution or solutions without said stabilizer (s), and combinations of two or more of these methods. One or more sensitizers may also be introduced into a tissue according to such methods.

It will be appreciated that the combination of one or more of the features described herein may be employed to further minimize undesirable effects upon the biological material caused by irradiation, while maintaining adequate effectiveness of the irradiation process on the biological contaminant (s) or pathogen(s). For example, in addition to the use of a stabilizer, a particular biological material may also be lyophilized, held at a reduced temperature and kept under vacuum prior to irradiation to further minimize undesirable effects.

It will further be appreciated that one or more of the methods for sterilizing described herein may be combined with one or more alternative methods known to those skilled in the art for sterilizing biological materials, such as treatment with detergent and/or heat.

The sensitivity of a particular biological contaminant or pathogen to radiation is commonly calculated by determining the dose necessary to inactivate or kill all but 37% of the agent in a sample, which is known as the D37 value. The desirable components of a biological material may also be considered to have a D37 value equal to the dose of radiation required to eliminate all but 37% of their desirable biological and physiological characteristics.

In accordance with certain preferred methods of the present invention, the sterilization of a biological material is conducted under conditions that result in a decrease in the D37 value of the biological contaminant or pathogen without a concomitant decrease in the D37 value of the biological material. In accordance with other preferred methods of the present invention, the sterilization of a biological material is conducted under conditions that result in an increase in the D37 value of the biological material. In accordance with the most preferred methods of the present invention, the sterilization of a biological material is conducted under conditions that result in a decrease in the D37 value of the biological contaminant or pathogen and a concomitant increase in the D37 value of the biological material.

EXAMPLES

The following examples are illustrative, but not limiting, of the present invention. Other suitable modifications and adaptations are of the variety normally encountered by those skilled in the art and are fully within the spirit and scope of the present invention. Unless otherwise noted, all irradiation was accomplished using a $^{60}$Co source.\

Example 1

In this experiment, the protective effect of the combination of ascorbate (20 mM), urate (1.5 mM) and trolox (200 mM) on gamma irradiated freeze-dried anti-insulin monoclonal immunoglobulin supplemented with 1% bovine serum albumin (BSA) was evaluated.

Methods

Samples were freeze-dried for approximately 64 hours, stoppered under vacuum, and sealed with an aluminum, crimped seal. Samples were irradiated at a dose rate of 1.83–1.88 kGy/hr to a total dose of 45.1–46.2 kGy at 4° C.

Monoclonal immunoglobulin activity was determined by a standard ELISA protocol. Maxisorp plates were coated with human recombinant insulin at 2.5 µg/ml overnight at 4° C. The plate was blocked with 200 µl of blocking buffer (PBS, pH 7.4, 2% BSA) for two hours at 37° C., and then washed six times with wash buffer (TBS, pH 7, 0.05% TWEEN 20). Samples were re-suspended in 500 µl of high purity water (100 ng/µl), diluted to 5 µg/ml in a 300 µl U-bottomed plate coated for either overnight or for two hours with blocking buffer. Serial 3-fold dilutions were performed, with a final concentration of 0.0022 µg/ml. Plates were incubated for one hour at 37° C. with agitation, and then washed six times with a wash buffer. Phosphatase-labelled goat anti-mouse IgG (H+L) was diluted to 50 ng/ml in binding buffer, and 100 µl was added to each well. The plate was incubated for one hour at 37° C. with agitation, and washed six times with wash buffers. One hundred µl of Sigma-104 substrate (1 mg/ml in DEA buffer) was added to each well, and reacted at room temperature. The plate was read on a Multiskan MCC/340 at 405 nm with the 620 nm absorbance subtracted.

Results

Freeze-dried anti-insulin monoclonal immunoglobulin, supplemented with 1% BSA, and gamma irradiated to 45 kGy, retained only about 68% of potency. Samples irradiated to 45 kGy in the presence of the stabilizer (ascorbate, urate and trolox), however, retained greater than 82% of potency.

Example 2

In this experiment, the protective effect of the combination of 200 µM Trolox, 1.5 mM urate, and 20 mM ascorbate on freeze-dried anti-insulin monoclonal immunoglobulin supplemented with 1% human serum albumin (HSA) and, optionally, 5% sucrose, irradiated at a high dose rate was evaluated.

Method

Samples were freeze-dried for approximately 64 hours, stoppered under vacuum, and sealed with an aluminum, crimped seal. Samples were irradiated at a dose rate of approximately 1.85 kGy/hr to a total dose of 45 kGy at 4° C.

Monoclonal immunoglobulin activity was determined by a standard ELISA protocol. Maxisorp plates were coated with human recombinant insulin at 2.5 µg/ml overnight at 4° C. The plate was blocked with 200 µl of blocking buffer (PBS, pH 7.4, 2% BSA) for two hours at 37° C., and then washed six times with wash buffer (TBS, pH 7, 0.05% TWEEN 20). Samples were re-suspended in 500 µl of high purity water (100 ng/µl), and diluted to 5 µg/ml in a 300 µl U-bottomed plate coated for either overnight or two hours with blocking buffer. Serial 3-fold dilutions were performed, with a final concentration of 0.0022 µg/ml. Plates were incubated for one hour at 37° C. with agitation, and then washed six times with wash buffer. Phosphatase-labelled goat anti-mouse IgG (H+L) was diluted to 50 ng/ml in binding buffer, and 100 µl was added to each well. The plate was incubated for one hour at 37° C. with agitation, and washed six times with wash buffers. One hundred µl of Sigma-104 substrate (1 mg/ml in DEA buffer) was added to each well and reacted at room temperature. The plate was read on a Multiskan MCC/340 at 405 nm with the 620 nm absorbance subtracted.

Results

Freeze-dried anti-insulin monoclonal immunoglobulin containing 1% HSA and the stabilizer (trolox/urate/ascorbate) retained about 87% of activity following gamma irradiation to 45 kGy. Freeze-dried anti-insulin monoclonal immunoglobulin containing only 1% HSA retained only 67% of activity following gamma irradiation to 45 kGy.

Freeze-dried anti-insulin monoclonal immunoglobulin containing 1% HSA, 5% sucrose and the stabilizer (trolox/urate/ascorbate) retained about 84% of activity following gamma irradiation to 45 kGy. Freeze-dried anti-insulin monoclonal immunoglobulin containing only 1% HSA and 5% sucrose retained only about 70% of activity following gamma irradiation to 45 kGy.

Example 3

In this experiment, the protective effect of ascorbate (200 mM), alone or in combination with Gly—Gly (200 mM), on a liquid polyclonal antibody preparation was evaluated.

Method

In 2 ml glass vials, samples of IGIV (50 mg/ml) were prepared with either no stabilizer or the stabilizer of interest. Samples were irradiated with gamma radiation (45 kGy total dose, dose rate 1.8 kGy/hr, temperature 4° C.) and then assayed for functional activity and structural integrity.

Functional activity of independent duplicate samples was determined by measuring binding activity for rubella, mumps and CMV using the appropriate commercial enzyme immunoassay (EIA) kit obtained from Sigma, viz., the Rubella IgG EIA kit, the Mumps IgG EIA kit and the CMV IgG EIA kit.

Structural integrity was determined by gel filtration (elution buffer: 50 mM NaPi, 100 mM NaCl, pH 6.7; flow rate: 1 ml/min; injection volume 50 µl) and SDS-PAGE (pre-cast tris-glycine 4–20% gradient gel from Novex in a Hoefer Mighty Small Gel Electrophoresis Unit running at 125V; sample size: 10 µl).

Results

Functional Activity

Irradiation of liquid polyclonal antibody samples to 45 kGy resulted in the loss of approximately 1 log of activity for rubella (relative to unirradiated samples). The addition of ascorbate alone improved recovery, as did the addition of ascorbate in combination with the dipeptide Gly—Gly.

Similarly, irradiation of liquid polyclonal antibody samples to 45 kGy resulted in the loss of approximately 0.5–0.75 log of activity for mumps. The addition of ascorbate alone improved recovery, as did the addition of ascorbate in combination with the dipeptide Gly—Gly.

Likewise, irradiation of liquid polyclonal antibody samples to 45 kGy resulted in the loss of approximately 1 log of activity for CMV. The addition of ascorbate alone improved recovery, as did the addition of ascorbate in combination with the dipeptide Gly—Gly.

Structural Analysis

Liquid polyclonal antibody samples irradiated to 45 kGy in the absence of a stabilizer showed significant loss of material and evidence of both aggregation and fragmentation. The irradiated samples containing ascorbate or a combination of ascorbate and the dipeptide Gly—Gly exhibited only slight breakdown and some aggregation.

Example 4

In this experiment, the protective effect of ascorbate (20 mM) and/or Gly—Gly (20 mM) on lyophilized anti-insulin monoclonal immunoglobulin irradiated at a high dose rate was evaluated.

Method

Samples were freeze-dried for approximately 64 hours and stoppered under vacuum and sealed with an aluminum, crimped seal. Samples were irradiated at a dose rate of 30 kGy/hr to a total dose of 45 kGy at 4° C.

Monoclonal immunoglobulin activity was determined by a standard ELISA protocol. Maxisorp plates were coated with human recombinant insulin at 2.5 µg/ml overnight at 4° C. The plate was blocked with 200 µl of blocking buffer (PBS, pH 7.4, 2% BSA) for two hours at 37° C. and then washed six times with wash buffer (TBS, pH 7, 0.05% TWEEN 20). Samples were re-suspended in 500 µl of high purity water (100 ng/µl), diluted to 5 µg/ml in a 300 µl U-bottomed plate coated for either overnight or two hours with blocking buffer. Serial 3-fold dilutions were performed, with a final concentration of 0.0022 µg/ml. Plates were incubated for one hour at 37° C. with agitation and then washed six times with a wash buffer. Phosphatase-labelled goat anti-mouse IgG (H+L) was diluted to 50 ng/ml in binding buffer and 100 µl was added to each well. The plate was incubated for one hour at 37° C. with agitation and washed six times with wash buffers. One hundred µl of Sigma-104 substrate (1 mg/ml in DEA buffer) was added to each well and reacted at room temperature. The plate was read on a Multiskan MCC/340 at 405 nm with the 620 nm absorbance subtracted.

Results

Lyophilized anti-insulin monoclonal immunoglobulin gamma irradiated to 45 kGy resulted in an average loss in activity of ~32% (average loss in avidity of ~1.5 fold).

Lyophilized anti-insulin monoclonal immunoglobulin samples irradiated to 45 kGy in the presence of 20 mM ascorbate alone had a 15% loss in activity (~1.1 fold loss in avidity), and those samples irradiated to 45 kGy in the presence of 20 mM Gly—Gly alone had a 23% loss in activity (~1.3 fold loss in avidity).

In contrast, lyophilized anti-insulin monoclonal immunoglobulin samples irradiated to 45 kGy in the presence of the stabilizer (20 mM ascorbate and 20 mM Gly—Gly) showed no loss in activity (no loss in avidity).

Example 5

In this experiment, the protective effect of ascorbate (200 mM) and/or Gly—Gly (200 mM) on liquid anti-insulin monoclonal immunoglobulin irradiated to 45 kGy.

Method

Liquid samples containing 100 µg antibody (2 mg/ml) with 10% BSA were irradiated at a dose rate of 1.83–1.88 kGy/hr to a total dose of 45.1–46.2 kGy at 4° C.

Monoclonal immunoglobulin activity was determined by a standard ELISA protocol. Maxisorp plates were coated with human recombinant insulin at 2.5 µg/ml overnight at 4° C. The plate was blocked with 200 µl of blocking buffer (PBS, pH 7.4, 2% BSA) for two hours at 37° C. and then washed six times with wash buffer (TBS, pH 7, 0.05% TWEEN 20). Samples were re-suspended in 500 µl of high purity water (100 ng/µl), diluted to 5 µg/ml in a 300 µl U-bottomed plate coated for either overnight or two hours with blocking buffer. Serial 3-fold dilutions were performed, with a final concentration of 0.0022 µg/ml. Plates were incubated for one hour at 37° C. with agitation and then washed six times with a wash buffer. Phosphatase-labelled goat anti-mouse IgG (H+L) was diluted to 50 ng/ml in binding buffer and 100 µl was added to each well. The plate was incubated for one hour at 37° C. with agitation and washed six times with wash buffers. One hundred µl of Sigma-104 substrate (1 mg/ml in DEA buffer) was added to each well and reacted at room temperature. The plate was read on a Multiskan MCC/340 at 405 nm with the 620 nm absorbance subtracted.

Results

Liquid anti-insulin monoclonal immunoglobulin gamma irradiated to 45 kGy exhibited a complete loss of activity.

Liquid anti-insulin monoclonal immunoglobulin samples irradiated to 45 kGy in the presence of 200 mM ascorbate alone exhibited a 48% loss in activity compared to unirradiated control.

In contrast, liquid anti-insulin monoclonal immunoglobulin samples irradiated to 45 kGy in the presence of the stabilizer (200 mM ascorbate and 200 mM Gly—Gly) showed only a 29% loss in activity.

Example 6

In this experiment, the protective effect of the combination of ascorbate (200 mM) and Gly—Gly (200 mM) on two different frozen enzyme preparations (a galactosidase and a sulfatase) was evaluated.

Method

In glass vials, 300 µl total volume containing 300 µg of enzyme (1 mg/ml) were prepared with either no stabilizer or the stabilizer of interest. Samples were irradiated with gamma radiation (45 kGy total dose, dose rate and temperature of either 1.616 kGy/hr and −21.5° C. or 5.35 kGy/hr and −21.9° C.) and then assayed for structural integrity.

Structural integrity was determined by SDS-PAGE. Three 12.5% gels were prepared according to the following recipe: 4.2 ml acrylamide; 2.5 ml 4X-Tris (pH 8.8); 3.3 ml water; 100 µl 10% APS solution; and 10 µl TEMED (tetramethylethylenediamine) and placed in an electrophoresis unit with 1× Running Buffer (15.1 g Tris base; 72.0 g glycine; 5.0 g SDS in 1 l water, diluted 5-fold). Irradiated and control samples (1 mg/ml) were diluted with Sample Buffer (+/−beta-mercaptoethanol) in Eppindorf tubes and then centrifuged for several minutes. 20 µl of each diluted sample (~10 µg) were assayed.

Results

Liquid galactosidase samples irradiated to 45 kGy in the absence of a stabilizer showed significant loss of material and evidence of both aggregation and fragmentation. Much greater recovery of material was obtained from the irradiated samples containing the combination of ascorbate and Gly—Gly.

Liquid sulfatase samples irradiated to 45 kGy in the absence of a stabilizer showed significant loss of material and evidence of both aggregation and fragmentation. Much greater recovery of material was obtained from the irradiated samples containing the combination of ascorbate and Gly—Gly.

Example 7

In this experiment, the protective effect of the combination of ascorbate (200 mM) and Gly—Gly (200 mM) on a frozen galactosidase preparation was evaluated. Method Samples were prepared in 2 ml glass vials containing 52.6 µl of a galactosidase solution (5.7 mg/ml), no stabilizer or the stabilizers of interest and sufficient water to make a total sample volume of 300 µl. Samples were irradiated at a dose rate of 1.616 or 5.35 kGy/hr at a temperature between −20 and −21.9° C. to a total dose of 45 kGy.

Structural integrity was determined by reverse phase chromatography. 10 µl of sample were diluted with 90 µl solvent A and then injected onto an Aquapore RP-300 (c-8) column (2.1×30 mm) mounted in an Applied Biosystems 130A Separation System Microbore HPLC. Solvent A: 0.1% trifluoroacetic acid; solvent B: 70% acetonitrile, 30% water, 0.085% trifluoroacetic acid.

Results

Liquid enzyme samples irradiated to 45 kGy in the absence of a stabilizer showed broadened and reduced peaks. Much greater recovery of material, as evidenced by significantly less reduction in peak size compared to control, was obtained from the irradiated samples containing the stabilizer (ascorbate and Gly—Gly).

Example 8

In this experiment, the protective effects of 200 mM glycylglycine, 200 mM ascorbate, and the combination of 200 mM Gly—Gly+200 mM ascorbate on gamma irradiated liquid anti-Ig Lambda Light Chain monoclonal antibody were evaluated.
Methods Vials containing 33.8 µg of anti-Ig Lambda Light Chain monoclonal antibody (0.169 mg/mL) plus 200 mM Gly—Gly, 200 mM ascorbate, or the combination of 200 mM ascorbate and 200 mM Gly—Gly, were irradiated at a rate of 1.752 kGy/hr to a total dose of about 45 kGy at a temperature of 4° C.

ELISA assays were performed as follows. Two microtitre plates were coated with Human IgGI, Lambda Purified Myeloma Protein at 2 µg/ml, and stored overnight at 4° C. The next day, an ELISA technique was performed using the standard reagents used in the Anti-Insulin ELISA. Following a one hour block, a 10 µg/ml dilution of each sample set was added to the first column of the plate and then serially diluted 3-fold through column 12. Incubation was then performed for one hour at 37° C. Next, a 1:8,000 dilution was made of the secondary antibody, Phosphatase-Labeled Goat Anti-Mouse IgG was added, and incubation was performed for one hour at 37° C. Sigma 104–105 Phosphatase Substrate was added, color was allowed to develop for about 15 minutes, and the reaction was stopped by adding 0.5 M NaOH. Absorbance was measured at 405 nm–620 nm.
Results Gamma irradiation of anti-Ig Lambda Light Chain monoclonal antibody to 45 kGy in the absence of stabilizers or in the presence of 200 mM Gly—Gly alone retained essentially no antibody activity. Samples that were gamma irradiated to 45 kGy in the presence of 200 mM ascorbate retained approximately 55% of antibody activity, but those irradiated in the presence of the stabilizer (200 mM ascorbate and 200 mM Gly—Gly) retained approximately 86% of antibody activity.

Example 9

In this experiment, the protective effects of a mixture of stabilizers (200 mM ascorbate and 200 mM glycylglycine) on gamma irradiated liquid anti-IgGI monoclonal antibody were evaluated.
Methods Vials were prepared containing 0.335 mg/ml of anti-IgGI or 0.335 mg/ml of anti-IgGI+200 mM ascorbate+200 mM Gly—Gly. The liquid samples were gamma irradiated to 45 kGy at 4° C. at a rate of 1.752 kGy/hr.

ELISA assays were performed as follows. Two microtitre plates were coated with Human IgG1, Lambda Purified Myeloma Protein at 2 µg/ml, and stored overnight at 4° C. The next day, an ELISA technique was performed using the standard reagents used in the Anti-Insulin ELISA. Following a one hour block, a 10 µg/ml dilution of each sample set was added to the first column of the plate and then serially diluted 3-fold through column 12. Incubation was then performed for one hour at 37° C. Next, a 1:8,000 dilution was made of the secondary antibody, Phosphatase-Labeled Goat Anti-Mouse IgG was added, and incubation was performed for one hour at 37° C. Sigma 104–105 Phosphatase Substrate was added, color was allowed to develop for about 15 minutes, and the reaction was stopped by adding 0.5 M NaOH. Absorbance was measured at 405 nm–620 nm.
Results Samples irradiated of liquid anti-IgGI antibody to 45 kGy alone retained essentially no antibody activity. In contrast, samples of liquid anti-IgGI antibody irradiated to 45 kGy in the presence of the stabilizer (200 mM ascorbate+200 mM Gly—Gly) retained 44% of antibody activity, more than was seen with ascorbate alone.

Example 10

In this experiment, the protective effects of 20 mM glycylglycine and 20 mM ascorbate on gamma irradiated freeze-dried anti-Ig Lambda Light Chain monoclonal antibody were evaluated.
Methods Vials containing 20 µg of liquid anti-Ig Lambda Light Chain monoclonal antibody and either 1% bovine serum albumin alone or 1% BSA plus 20 mM ascorbate and 20 mM Gly—Gly were freeze-dried, and irradiated to 45 kGy at a dose rate of 1.741 kGy/hr at 3.8° C.

ELISA assays were performed as follows. Four microtitre plates were coated with Human IgG1, Lambda Purified Myeloma Protein at 2 µg/ml, and stored overnight at 4° C. The next day, an ELISA technique was performed using the standard reagents used in the Anti-Insulin ELISA. Following a one hour block, a 10 µg/ml dilution of each sample set was added to the first column of the plate and then serially diluted 3-fold through column 12. Incubation was then performed for one hour at 37° C. Next, a 1:8,000 dilution was made of the secondary antibody, Phosphatase-Labeled Goat Anti-Mouse IgG was added, and incubation was performed for one hour at 37° C. Sigma 104–105 Phosphatase Substrate was added, color was allowed to develop for about 15 minutes, and the reaction was stopped by adding 0.5 M NaOH. Absorbance was measured at 405 nm–620 nm.
Results Samples of freeze-dried anti-Ig Lambda Light Chain monoclonal antibody gamma irradiated to 45 kGy with 1% BSA alone retained only 55% of antibody activity. In contrast, samples of freeze-dried anti-Ig Lambda Light Chain monoclonal antibody irradiated to 45 kGy in the presence of the stabilizer (20 mM ascorbate and 20 mM Gly—Gly) retained 76% of antibody activity.

Example 11

In this experiment, the protective effects of ascorbate and glycylglycine, alone or in combination, on gamma irradiated freeze-dried anti-IgG1 monoclonal antibody were evaluated.
Methods Vials containing 77.6 µg of anti-IgG1 monoclonal antibody, 1% human serum albumin, and one of 20 mM ascorbate, 20 mM Gly—Gly, or 20 mM ascorbate and 20 mM Gly—Gly, were lyophilized, and gamma irradiated to 47.4 to 51.5 kGy at a dose rate of 1.82 to 1.98 kGy/hr at 4° C.

ELISA assays were performed as follows. Four microtitre plates were coated with Human IgG1, Lambda Purified Myeloma Protein at 2 µg/ml, and stored overnight at 4° C. The next day, an ELISA technique was performed using the standard reagents used in the Anti-Insulin ELISA. Following a one hour block, a 7.75 µg/ml dilution of each sample set was added to the first column of the plate and then serially diluted 3-fold through column 12. Incubation was then performed for one hour at 37° C. Next, a 1:8,000 dilution was made of the secondary antibody, Phosphatase-Labeled Goat Anti-Mouse IgG was added, and incubation was performed for one hour at 37° C. Sigma 104–105 Phosphatase Substrate was added, color was allowed to develop for about 15 minutes, and the reaction was stopped by adding 0.5 M NaOH. Absorbance was measured at 405 nm–620 nm.

Results

Samples of freeze-dried monoclonal anti-IgG1 with 1% human serum albumin retained 62% of antibody activity following gamma irradiation when no stabilizers were present. In contrast, samples of freeze-dried monoclonal anti-IgG1 with 1% human serum albumin and the stabilizer retained 85.3% of antibody activity.

Example 12

In this experiment, the protective effect of a stabilizer (200 mM ascorbate and 200 mM Gly—Gly) on anti-insulin monoclonal immunoglobulin (50 mg/ml) supplemented with 0.1% human serum albumin (HSA) exposed to gamma irradiation up to 100 kGy was evaluated.

Methods

Samples were irradiated at a dose rate of 0.458 kGy/hr to a total dose of 25, 50 or 100 kGy at ambient temperature (20–25° C.).

Monoclonal immunoglobulin activity was determined by a standard ELISA protocol. Maxisorp plates were coated with human recombinant insulin at 2.5 μg/ml overnight at 4° C. The plate was blocked with 380 μl of blocking buffer (PBS, pH 7.4, 2% BSA) for two hours at 37° C. and then washed three times with wash buffer (TBS, pH 7, 0.05% TWEEN 20). Serial 3-fold dilutions were performed. Plates were incubated for one hour at 37° C. with agitation and then washed six times with a wash buffer. Phosphatase-labelled goat anti-mouse IgG (H+L) was diluted to 50 ng/ml in binding buffer and 100 μl was added to each well. The plate was incubated for one hour at 37° C. with agitation and washed eight times with wash buffers. One hundred μl of Sigma-104 substrate (1 mg/ml in DEA buffer) was added to each well and reacted at room temperature. The plate was read on a Multiskan MCC/340 at 405 nm–620 nm.

Results

Samples of anti-insulin monoclonal immunoglobulin supplemented with 1% HSA lost all binding activity when gamma irradiated to 25 kGy. In contrast, samples containing a combination of ascorbate and Gly—Gly retained about 67% of binding activity when irradiated to 25 kGy, 50% when irradiated to 50 kGy and about 33% when irradiated to 100 kGy.

Example 13

In this experiment, the protective effect of the combination of ascorbate, urate and trolox on gamma irradiated immobilized anti-insulin monoclonal immunoglobulin was evaluated.

Methods

The stabilizer of 200 mM ascorbate (Aldrich 26,855-0, prepared as 2M stock solution in water), 300 mM urate (Sigma U-2875m, prepared as a 2 mM stock solution in water) and 200 mM trolox (Aldrich 23,681-2, prepared as a 2 mM stock solution in PBS, pH 7.4) was prepared as a solution in PBS pH 7.4 and added to each sample being irradiated. Samples were irradiated to a total dose of 45 kGy at a dose rate of 1.92 kGy/hr at 4° C.

Monoclonal immunoglobulin activity was determined by a standard ELISA protocol. Maxisorp plates were coated with human recombinant insulin at 2 μg/ml overnight at 4° C. The plate was blocked with 200 μl of blocking buffer (PBS, pH 7.4, 2% BSA) for two hours at 37° C. and then washed six times with wash buffer (TBS, pH 7, 0.05% TWEEN 20). Samples were re-suspended in 500 μl of high purity water (100 ng/μl), diluted to 5 μg/ml in a 300 μl U-bottomed plate coated for either overnight or two hours with blocking buffer. Serial 3-fold dilutions were performed, with a final concentration of 0.0022 μg/ml. Plates were incubated for one hour at 37° C. with agitation and then washed six times with a wash buffer. Phosphatase-labelled goat anti-mouse IgG (H+L) was diluted to 50 ng/ml in binding buffer and 100 μl was added to each well. The plate was incubated for one hour at 37° C. with agitation and washed six times with wash buffers. One hundred μl of Sigma-104 substrate (1 mg/ml in DEA buffer) was added to each well and reacted at room temperature. The plate was read on a Multiskan MCC/340 at 405 nm with the 620 nm absorbance subtracted.

Results

Samples of immobilized anti-insulin monoclonal immunoglobulin lost all binding activity when gamma irradiated to 45 kGy. In contrast, samples containing the stabilizer (ascorbate/urate/trolox) retained about 75% of binding activity following gamma irradiation to 45 kGy.

Example 14

In this experiment, the protective effect of the combination of L-carnosine and ascorbate on gamma irradiated immobilized anti-insulin monoclonal immunoglobulin was evaluated.

Methods

L-carnosine was prepared as a solution in PBS pH 8–8.5 and added to each sample being irradiated across a range of concentration (25 mM, 50 mM, 100 mM or 200 mM). Ascorbate (either 50 mM or 200 mM) was added to some of the samples prior to irradiation. Samples were irradiated at a dose rate of 1.92 kGy/hr to a total dose of 45 kGy at 4° C.

Monoclonal immunoglobulin activity was determined by a standard ELISA protocol. Maxisorp plates were coated with human recombinant insulin at 2 μg/ml overnight at 4° C. The plate was blocked with 200 μl of blocking buffer (PBS, pH 7.4, 2% BSA) for two hours at 37° C. and then washed six times with wash buffer (TBS, pH 7, 0.05% TWEEN 20). Samples were re-suspended in 500 μl of high purity water (100 ng/μl), diluted to 5 μg/ml in a 300 μl U-bottomed plate coated for either overnight or two hours with blocking buffer. Serial 3-fold dilutions were performed, with a final concentration of 0.0022 μg/ml. Plates were incubated for one hour at 37° C. with agitation and then washed six times with a wash buffer. Phosphatase-labelled goat anti-mouse IgG (H+L) was diluted to 50 ng/ml in binding buffer and 100 μl was added to each well. The plate was incubated for one hour at 37° C. with agitation and washed six times with wash buffers. One hundred μl of Sigma-104 substrate (1 mg/ml in DEA buffer) was added to each well and reacted at room temperature. The plate was read on a Multiskan MCC/340 at 405 nm with the 620 nm absorbance subtracted.

Results

Samples of immobilized anti-insulin monoclonal immunoglobulin lost all binding activity when gamma irradiated to 45 kGy. In contrast, samples containing at least 50 mM L-carnosine and 50 mM ascorbate retained about 50% of binding activity following gamma irradiation to 45 kGy.

Example 15

In this experiment, the protective effects of a number of stabilizers on gamma irradiated lyophilized Factor VIII were evaluated.

Methods

Samples containing Factor VIII and the stabilizer of interest (cysteine and ascorbate; N-acetyl-cysteine and ascorbate; or L-carnosine and ascorbate) were lyophilized and stoppered under vacuum. Samples were irradiated at a dose rate of 1.9 kGy/hr to a total dose of 45 kGy at 4° C. Following irradiation, samples were reconstituted with water containing BSA (125 mg/ml) and Factor VIII activity was determined by a one-stage clotting assay using an MLA Electra 1400C Automatic Coagulation Analyzer.

Results

Factor VIII samples containing no stabilizer retained only 32.5% of Factor VIII clotting activity following gamma irradiation to 45 kGy. In contrast, Factor VIII samples containing cysteine and ascorbate retained 43.3% of Factor VIII clotting activity following irradiation. Similarly, Factor VIII samples containing N-acetyl-cysteine and ascorbate or L-carnosine and ascorbate retained 35.5% and 39.8%, respectively, of Factor VIII clotting activity following irradiation to 45 kGy.

Example 16

In this experiment, the protective effects of 1.5 mM uric acid in the presence of varying amounts of ascorbate on gamma irradiated immobilized anti-insulin monoclonal antibodies were evaluated.

Methods

Maxisorp Immuno microtitre plates were coated with 100 $\mu$l of anti-insulin monoclonal antibody (2.5 $\mu$g/ml), non-bound antibody was removed by rinsing, 1.5 mM uric acid was added, along with varying amounts (5, 10, 15, 20, 25, 30, 35, 40, 50, 60, 70, 80, 90, 100, 120, 140, 160, 180, 200, 300, 400 and 500 mM) of ascorbate, and were gamma irradiated to 45 kGy at a dose rate of 1.9 kGy/hr at 4° C.

Anti-insulin antibody binding was evaluated by the following procedure. Microtitre plates with anti-insulin monoclonal antibody immobilized therein were incubated and rinsed twice with full volumes of phosphate buffered saline (pH 7.4). Non-specific binding sites were blocked with full volumes of blocking buffer (PBS+2% bovine serum albumin) and 2 hours of incubation at 37° C. The wells were then washed 3 times with TBST (TBS pH 7.4, with 0.05% Tween 20), and to each well was added 100 $\mu$l of 10 ng/ml insulin-biotin in binding buffer (0.25% bovine serum albumin in PBS, pH 7.4). The titre plate was then covered/sealed and incubated one hour with shaking at 37° C. The microtitre plates where then washed with TBST for 4 sets of 2 washes/set, with about a 5 minute sitting period allowed between each set. Then, 100 $\mu$l of 25 ng/ml phosphatase-labeled Streptavidin was added to each well, the microtitre plate covered/sealed, and incubated at 37° C. with shaking for one hour. The microtitre plates were then washed with TBST for 4 sets of 2 washes per set, with about a 5 minute sitting period allowed between each set. To each well was then added 100 $\mu$l of 1 mg/ml Sigma 104 phosphatase substrate in DEA buffer (per liter: 97 ml of diethanolamine, 0.1 g $MgCl_2.6H_2O$, 0.02% sodium azide), and the plates incubated at ambient temperature with nutating. Absorbance was then measured at 405 nm–620 nm for each well.

Results

The stabilizer mixture of uric acid and ascorbate provided greater protection, as determined by activity retained following irradiation, than ascorbate alone across the range of concentrations employed. Moreover, with ascorbate alone, maximal protection was achieved at a concentration of about 50 mM ascorbate, whereas with the addition of 1.5 mM uric acid, maximal protection was achieved at a concentration of about 30 mM ascorbate.

Example 17

In this experiment, the protective effects of 2.25 mM uric acid in the presence of varying amounts of ascorbate on gamma irradiated immobilized anti-insulin monoclonal antibodies were evaluated.

Methods

Maxisorp Immuno microtitre plates were coated with 100 $\mu$l of anti-insulin monoclonal antibody (2.5 $\mu$g/ml), non-bound antibody was removed by rinsing, 1.5 mM uric acid was added, along with varying amounts (5, 10, 15, 20, 25, 30, 35, 40, 50, 60, 70, 80, 90, 100, 120, 140, 160, 180, 200, 300, 400 and 500 mM) of ascorbate, and were gamma irradiated to 45 kGy at a dose rate of 1.9 kGy/hr at 4° C.

Anti-insulin antibody binding was evaluated by the following procedure. Microtitre plates with anti-insulin monoclonal antibody immobilized therein were incubated and rinsed twice with full volumes of phosphate buffered saline (pH 7.4). Non-specific binding sites were blocked with full volumes of blocking buffer (PBS+2% bovine serum albumin) and 2 hours of incubation at 37° C. The wells were then washed 3 times with TBST (TBS pH 7.4, with 0.05% Tween 20), and to each well was added 100 $\mu$l of 10 ng/ml insulin-biotin in binding buffer (0.25% bovine serum albumin in PBS, pH 7.4). The titre plate was then covered/sealed and incubated one hour with shaking at 37° C. The microtitre plates where then washed with TBST for 4 sets of 2 washes/set, with about a 5 minute sitting period allowed between each set. Then, 100 $\mu$l of 25 ng/ml phosphatase-labeled Streptavidin was added to each well, the microtitre plate covered/sealed, and incubated at 37° C. with shaking for one hour. The microtitre plates were then washed with TBST for 4 sets of 2 washes per set, with about a 5 minute sitting period allowed between each set. To each well was then added 100 $\mu$l of 1 mg/ml Sigma 104 phosphatase substrate in DEA buffer (per liter: 97 ml of diethanolamine, 0.1 g $MgCl_2.6H_2O$, 0.02% sodium azide), and the plates incubated at ambient temperature with nutating. Absorbance was then measured at 405 nm–620 nm for each well.

Results

The stabilizer mixture of uric acid and ascorbate provided greater protection, as determined by activity retained following irradiation, than ascorbate alone across the range of concentrations employed. Moreover, with ascorbate alone, maximal protection was achieved at a concentration of about 75 mM ascorbate, whereas with the addition of 2.25 mM uric acid, maximal protection (100% activity retained after irradiation) was achieved at a concentration of about 25 mM ascorbate.

Example 18

In this experiment, the protective effects of various stabilizers on gamma irradiated lyophilized human coagulation Factor VIII (one step clotting assay) activity.

Methods

Sealed vials containing 12 IU of Baxter Anti-Hemophiliac Factor VIII (Human) and 2.5 mg of bovine serum albumin (total volume 350 $\mu$l) were combined with the stabilizer of interest and lyophilized. Lyophilized samples were subjected to gamma irradiation to 45 kGy at a dose rate of 1.9 kGy/hr at 4° C. Following gamma irradiation, each sample was reconstituted in 200 $\mu$l of high purity water (from NERL), and assayed for Factor VIII activity using a one-stage clotting assay on an MLA Electra 1400C Automatic Coagulation Analyzer (Hemoliance). The following stabilizer were tested: 200 mM ascorbate+300 $\mu$M uric acid; 300 $\mu$M uric acid+200 $\mu$M Trolox; and 200 mM ascorbate+300 $\mu$M uric acid+200 $\mu$M Trolox.

Results

When compared to unirradiated control, irradiated samples containing 200 mM ascorbate+300 µM uric acid exhibited a recovery of 53% of Factor VIII activity. Irradiated samples containing 300 µM uric acid+200 µM Trolox exhibited a recovery of 49% of Factor VIII activity and irradiated samples containing 200 mM ascorbate+300 µM uric acid+200 µM Trolox exhibited a recovery of 53% of Factor VIII activity. In contrast, irradiated samples containing no stabilizer exhibited a recovery of only 38% of Factor VIII activity.

Example 19

In this experiment, the protective effects of a combination of 200 µM Silymarin+200 mM ascorbate+200 µM Trolox (silymarin cocktail) and a combination of 200 µM Diosmin+ 200 mM ascorbate+200 µM Trolox (diosmin cocktail), on gamma irradiated lyophilized human anti-hemophiliac clotting Factor VIII (monoclonal) activity were evaluated.
Methods Aliquots of 200 µl of monoclonal human Factor VIII (21 IU/vial), alone or in combination with the cocktail of interest, were placed in 2 ml vials, frozen at −80° C., and lyophilized. Gamma irradiation to 45 kGy was performed at a dose rate of 1.9 kGy/hr at 4° C. Single-step clotting rates were determined using an MLA Electra 1400C Automatic Coagulation Analyzer (Hemoliance).
Results Lyophilized Factor VIII irradiated to 45 kGy retained about 18–20% of Factor VIII activity compared to fresh frozen Factor VIII. In contrast, samples containing the diosmin cocktail retained between 40–50% of Factor VIII activity following irradiation to 45 kGy and samples containing the silymarin cocktail retained about 25% of Factor VIII activity following irradiation to 45 kGy.

Example 20

In this experiment, the protective effects of the combination of ascorbate and trolox and the combination of ascorbate, trolox and urate on urokinase enzymatic activity were evaluated as a function of pH in phosphate buffer solution.
Methods Samples were prepared in 2 ml vials, each containing 1,000 IU of urokinase (Sigma) and 35 µl of µM phosphate buffer (pH=4, 5, 5.5, 6.0, 6.47, 7, 7.5, 7.8, 8.5 or 9.0). Stabilizers (a mixture of 100 µl of 3 mM trolox and 100 µl of 2 M sodium ascorbate or a mixture of 100 µl of 3 mM trolox, 100 µl of 2 M sodium ascorbate and 100 µl of 3 mM sodium urate) or trolox alone were added and the samples gamma irradiated to 45 kGy at a dose rate of 1.8 kGy/hr at 4° C. Residual urokinase activity was determined at room temperature at 5 and 25 minutes after commencement of reaction by addition of urokinase colorimetric substrate #1 (CalBiochem). Optical densities were measured at 405 nm, with subtraction of the optical density at 620 nm.
Results The irradiated samples containing a stabilizer exhibited much greater retention of urokinase activity compared to samples containing only a single stabilizer across the range of pH tested. More specifically, at pH 4, irradiated samples containing trolox/ascorbate (T/A) retained 65.1% of urokinase activity and samples containing trolox/ascorbate/urate (T/A/U) retained 66.2% of urokinase activity. In contrast, at pH 4, samples containing only trolox retained only 5.3% of urokinase activity. The following results were also obtained:

| pH | stabilizer | urokinase activity |
|---|---|---|
| 5.0 | trolox | 13% |
|  | T/A | 72.2% |
|  | T/A/U | 62.2% |
| 5.5 | trolox | 13% |
|  | T/A | 66.7% |
|  | T/A/U | 66.3% |
| 6.0 | trolox | 30% |
|  | T/A | 61.8% |
|  | T/A/U | 61.8% |
| 6.47 | trolox | 30% |
|  | T/A | 70.5% |
|  | T/A/U | 70.2% |
| 7.0 | trolox | 20% |
|  | T/A | 69.5% |
|  | T/A/U | 65.9% |
| 7.5 | trolox | 24% |
|  | T/A | 72.1% |
|  | T/A/U | 64.0% |
| 7.8 | trolox | 28% |
|  | T/A | 63.5% |
|  | T/A/U | 70.7% |
| 8.5 | trolox | 23% |
|  | T/A | 64.4% |
|  | T/A/U | 70.2% |
| 9.0 | trolox | 38% |
|  | T/A | 71.3% |
|  | T/A/U | 68.73% |

Example 21

In this experiment, the protective effects of the combination of ascorbate and urate on urokinase enzymatic activity were evaluated as a function of pH in phosphate buffer solution.
Methods Samples were prepared in 2 ml vials, each containing 1,000 IU of urokinase (Sigma) and 35 µl of 1M phosphate buffer (pH=4, 5, 6.0, 6.47, 7, 7.8 or 9.0). A stabilizer of 100 µl of 2 M sodium ascorbate and 100 µl of 3 mM sodium urate was added and the samples gamma irradiated to 45 kGy at a dose rate of 1.8 kGy/hr at 4° C. Residual urokinase activity was determined at room temperature at 5 and 25 minutes after commencement of reaction by addition of urokinase colorimetric substrate #1 (CalBiochem). Optical densities were measured at 405 nm, with subtraction of the optical density at 620 nm.
Results The irradiated samples containing a stabilizer exhibited much greater retention of urokinase activity compared to samples containing only urate across the range of pH tested. More specifically, irradiated samples containing ascorbate/urate retained between 48.97% (at pH 9.0) and 64.01% (at pH 6.47) of urokinase activity, whereas irradiated samples containing only urate retained essentially no urokinase activity.

Example 22

In this experiment, the protective effects of the combination of ascorbate (200 mM) and Gly—Gly (200 mM) on lyophilized galactosidase preparations were investigated.
Methods Samples were prepared in glass vials, each containing 300 µg of a lyophilized glycosidase and either no stabilizer or the stabilizer. Samples were irradiated with gamma radiation to varying total doses (10 kGy, 30 kGy and 50 kGy total dose, at a rate of 0.6 kGy/hr. and a temperature of −60° C.) and then assayed for structural integrity using SDS-PAGE.

Samples were reconstituted with water to a concentration of 1 mg/ml, diluted 1:1 with 2× sample buffer (15.0 ml 4× Upper Tris-SDS buffer (pH 6.8); 1.2 g sodium dodecyl sulfate; 6 ml glycerol; sufficient water to make up 30 ml; either with or without 0.46 g dithiothreitol), and then heated at 80° C. for 10 minutes. 10 μl of each sample (containing 5 μg of enzyme) were loaded into each lane of a 10% polyacrylamide gel and run on an electrophoresis unit at 125V for about 1.5 hours.

Results

About 80% of the enzyme was recovered following irradiation of the samples containing no stabilizer, with some degradation. Significantly less degradation was observed in the samples containing a combination of ascorbate and glycylglycine as the stabilizer.

Example 23

In this experiment, the protective effects of ascorbate and lipoic acid on gamma irradiated liquid Thrombin activity were evaluated.

Methods

Two microtitre dilution plates were prepared—one for samples to receive gamma irradiation, and one for control samples (no gamma irradiation)—containing a range of concentrations of ascorbate and lipoic acid. Samples receiving gamma irradiation were irradiated to 45 kGy at a dose rate of 1.788 kGy/hr at 4.2° C.

Thrombin activity was measured by conventional procedure, which was commenced by adding 50 μl of 1600 μM substrate to each 50 μl of sample in a well of a Nunc 96 low protein binding plate, and absorbance was read for 60 minutes at 10 minute intervals.

Results

When both ascorbate and lipoic acid were present, synergistic protective effects were apparent, as is shown by the following data:

| [ascorbate] | [lipoic acid] | % recovery of Thrombin activity |
|---|---|---|
| 0 mM | 100 mM | 10 |
| 10 mM | 0 mM | 2 |
| 10 mM | 200–225 mM | 80.3 |
| 50 mM | 100–175 mM | 82–85 |
| 100 mM | 10–25 mM | 78 |
| 100 mM | 0 mM | 52 |

Example 24

In this experiment, the protective effects of a combination of ascorbate and lipoic acid on gamma irradiated freeze-dried Thrombin activity were evaluated.

Methods

Two microtitre dilution plates were prepared—one for samples to receive gamma irradiation, and one for control samples (no gamma irradiation)—containing a range of concentrations of ascorbate and lipoic acid. Samples receiving gamma irradiation were irradiated to 45 kGy at a dose rate of 1.78 kGy/hr at 4.80° C.

Thrombin activity was measured by conventional procedure, which was commenced by adding 50 μl of 1600 μM substrate to each 50 μl of sample in a well of a Nunc 96 low protein binding plate, and absorbance was read for 60 minutes at 10 minute intervals.

Results

When both ascorbate and lipoic acid were present, synergistic protective effects were apparent, as is shown by the following data:

| [ascorbate] | [lipoic acid] | % recovery of Thrombin activity |
|---|---|---|
| 0 mM | 0 mM | 54.8 |
| 0 mM | 100 mM | 73.5 |
| 25 mM | 0 mM | 74.5 |
| 2.5 mM | 40 mM | 83.5 |
| 5 mM | 5 mM | 80.3 |
| 5 mM | 10 mM | 84.3 |
| 5 mM | 100 mM | 89.5 |
| 10 mM | 40 mM | 85 |
| 25 mM | 10 mM | 86.2 |
| 25 mM | 100 mM | 84.7 |

Example 25

In this experiment, the protective effects of a combination of ascorbate and hydroquinonesulfonic acid (HQ) on gamma irradiated liquid Thrombin were evaluated.

Methods

Two microtitre dilution plates were prepared—one for samples to receive gamma irradiation, and one for control samples (no gamma irradiation)—containing a range of concentrations of ascorbate and hydroquinonesulfonic acid (HQ). Samples receiving gamma irradiation were irradiated to 45 kGy at a dose rate of 1.78 kGy/hr at 3.5–4.9° C.

Thrombin activity was measured by conventional procedure, which was commenced by adding 50 μl of 1600 μM substrate to each 50 μl of sample in a well of a Nunc 96 low protein binding plate, and absorbance was read for 60 minutes at 10 minute intervals.

Results

When both ascorbate and hydroquinonesulfonic acid were present, synergistic protective effects were apparent, as is shown by the following data:

| [ascorbate] | [HQ] | % recovery of Thrombin activity |
|---|---|---|
| 0 mM | 0 mM | 0 |
| 0 mM | 187.5 mM | 2 |
| 200 mM | 0 mM | 59 |
| 200 mM | 187.5 mM | 68 |
| 50 mM | 187.5 mM | 70 |
| 50 mM | 100 mM | 70 |
| 50 mM | 50 mM | 66.9 |
| 100 mM | 75 mM | 73 |
| 100 mM | 100 mM | 73 |
| 200 mM | 25–50 mM | 72 |

Example 26

In this experiment, the protective effects of a combination of ascorbate (200 mM), urate (0.3 mM) and trolox (0.2 mM) on gamma irradiated liquid Thrombin were evaluated.

Methods

Samples were prepared of thrombin (5000 U/ml) and either no stabilizer or the stabilizer of interest. Samples receiving gamma irradiation were irradiated to 45 kGy at a dose rate of 1.852 kGy/hr at 4° C.

Following irradiation, thrombin activity was measured by conventional procedure.

Results

Samples of liquid thrombin containing no stabilizer retained no activity following irradiation to 45 kGy. In contrast, samples of liquid thrombin containing the ascorbate/trolox/urate mixture retained about 50% of thrombin activity following irradiation to 45 kGy.

Example 27

In this experiment, the protective effects of a combination of ascorbate (200 mM), urate (0.3 mM) and trolox (0.2 mM) on gamma irradiated liquid Thrombin were evaluated.

Methods

Samples were prepared of thrombin (5000 U/ml) and either no stabilizer or the stabilizer of interest and, optionally, 0.2% bovine serum albumin (BSA). Samples receiving gamma irradiation were irradiated to 45 kGy at a dose rate of 1.852 kGy/hr at 4° C.

Following irradiation, thrombin activity was measured by conventional procedure.

Results

Samples of liquid thrombin containing no stabilizer or BSA alone retained no activity following irradiation to 45 kGy. In contrast, samples of liquid thrombin containing the ascorbate/trolox/urate mixture retained about 50% of thrombin activity following irradiation to 45 kGy. Moreover, samples of liquid thrombin containing ascorbate/trolox/urate and BSA retained between 55 and 78.5% of thrombin activity following irradiation to 45 kGy.

Example 28

In this experiment, the protective effect of ascorbate (200 mM) and a combination of ascorbate (200 mM) and Gly—Gly (200 mM) on a frozen galactosidase preparation was evaluated.

Method

In glass vials, 300 $\mu$l total volume containing 300 $\mu$g of enzyme (1 mg/ml) were prepared with either no stabilizer or the stabilizer of interest. Samples were irradiated with gamma radiation (45 kGy total dose, dose rate and temperature of 1.616 kGy/hr and −21.5° C. or 5.35 kGy/hr and −21.9° C.) and then assayed for structural integrity.

Structural integrity was determined by SDS-PAGE. Three 12.5% gels were prepared according to the following recipe: 4.2 ml acrylamide; 2.5 ml 4x-Tris (pH 8.8); 3.3 ml water; 100 $\mu$l 10% APS solution; and 10$\mu$l TEMED (tetramethylethylenediamine). This solution was then placed in an electrophoresis unit with IX Running Buffer (15.1 g Tris base; 72.0 g glycine; 5.0 g SDS in 1 l water, diluted 5-fold). Irradiated and control samples (1 mg/ml) were diluted with Sample Buffer (+/−beta-mercaptoethanol) in Eppindorf tubes and then centrifuged for several minutes. 20 $\mu$l of each diluted sample (~10 $\mu$g) were assayed.

Results

Liquid enzyme samples irradiated to 45 kGy in the absence of a stabilizer showed significant loss of material and evidence of both aggregation and fragmentation. Much greater recovery of material was obtained from the irradiated samples containing ascorbate or a combination of ascorbate and Gly—Gly.

Example 29

In this experiment, the protective effect of ascorbate (200 mM) and a combination of ascorbate (200 mM) and Gly—Gly (200 mM) on a frozen galactosidase preparation was evaluated.

Method

Samples were prepared in 2 ml glass vials, each containing 52.6 $\mu$l of a glycosidase solution (5.7 mg/ml), and either no stabilizer or a stabilizer of interest, and sufficient water to make a total sample volume of 300 $\mu$l. Samples were irradiated with gamma radiation (45 kGy total dose, dose rate and temperature of either 1.616 kGy/hr and −21.5° C. or 5.35 kGy/hr and −21.9° C.) and then assayed for structural integrity.

Structural integrity was determined by reverse phase chromatography. 10 $\mu$l of sample were diluted with 90 $\mu$l solvent A and then injected onto an Aquapore RP-300 (c-8) column (2.1×30 mm) mounted in an Applied Biosystems 130A Separation System Microbore HPLC. Solvent A: 0.1% trifluoroacetic acid; solvent B: 70% acetonitrile, 30% water, 0.085% trifluoroacetic acid.

Results

Enzyme samples irradiated to 45 kGy in the absence of a stabilizer showed broadened and reduced peaks. Much greater recovery of material, as evidenced by significantly less reduction in peak size compared to control was obtained from the irradiated samples containing ascorbate or a combination of ascorbate and Gly—Gly.

Example 30

In this experiment, lyophilized galactosidase preparations were irradiated in the absence or presence of a stabilizer (100 mM sodium ascorbate).

Method

Glass vials containing 1 mg of enzyme were prepared with either no stabilizer or 100 mM sodium ascorbate (50 $\mu$l of 2M solution) and sufficient water to make 1 ml of sample. Samples were lyophilized, resulting in the following moisture levels: galactosidase with stabilizer, 3.4%; galactosidase without stabilizer, 3.2%. Lyophilized samples were irradiated with gamma radiation (45 kGy total dose at 1.8 kGy/hr and 4° C.) and then assayed for structural integrity.

Structural integrity was determined by SDS-PAGE. In an electrophoresis unit, 6 $\mu$g/lane of each sample was run at 120V on a 7.5%–15% acrylamide gradient gel with a 4.5% acrylamide stacker under non-reducing conditions.

Results

Lyophilized galactosidase samples irradiated to 45 kGy in the absence of a stabilizer showed significant recovery of intact enzyme with only some fragmentation. This contrasts to the much higher levels of degradation seen in the frozen liquid preparation described in Example 28, indicating that the reduction of solvent (water) significantly reduced radiation induced damage. Fragmentation was even further reduced by the addition of a stabilizer.

Example 31

In this experiment, lyophilized galactosidase preparations irradiated in the absence or presence of a stabilizer (200 mM sodium ascorbate or a combination of 200 mM ascorbate and 200 mM glycylglycine).

Methods

Samples were prepared in glass vials, each containing 300 $\mu$g of a lyophilized glycosidase and either no stabilizer or a stabilizer of interest. Samples were irradiated with gamma radiation to various total doses (10 kGy, 30 kGy and 50 kGy total dose, at a rate of 0.6 kGy/hr. at a temperature of −60° C.) and then assayed for structural integrity using SDS-PAGE.

Samples were reconstituted with water to a concentration of 1 mg/ml, diluted 1:1 with 2× sample buffer (15.0 ml 4× Upper Tris-SDS buffer (pH 6.8); 1.2 g sodium dodecyl sulfate; 6 ml glycerol; sufficient water to make up 30 ml; either with or without 0.46 g dithiothreitol), and then heated at 80° C. for 10 minutes. 10 $\mu$l of each sample (containing 5 $\mu$g of enzyme) were loaded into each lane of a 10% polyacrylamide gel and run on an electrophoresis unit at 125V for about 1.5 hours.

Results

About 80% of the enzyme was recovered following irradiation of the samples containing no stabilizer. These samples had a visible precipitate post-irradiation, while those with a stabilizer did not. Nevertheless, some degradation of the remaining soluble material without stabilizer was seen, particularly the emergence of a new band at approximately 116 kDa. Less degradation was observed in the samples containing ascorbate alone as the stabilizer, and even less degradation in the samples containing a combination of ascorbate and glycylglycine as the stabilizer. These results were better than those observed in the previous Example in which the preparation was lyophylized to reduce solvent (water) and irradiated at 4° C. indicating that the reduction in temperature to −60° C., along with increased concentrations of ascorbate and the addition of glycylglycine further reduced the damage to the glycosidase preparation.

Example 32

In this experiment, the protective effects of the flavonoids/flavonols diosmin and silymarin on gamma irradiated freeze-dried anti-insulin monoclonal immunoglobulin supplemented with 1% bovine serum albumin (BSA) were evaluated.

Methods

Samples were prepared by combining anti-insulin monoclonal antibody (50 ml of 2 mg/ml solution) and either diosmin (39.3 µM; Sigma cat# D3525 lot 125H0831) or silymarin (246 µM; Aldrich cat #24592-4) in 3 ml glass vials with 13 mm stoppers. Samples were freeze-dried for approximately 64 hours and stoppered under vacuum and sealed with an aluminum, crimped seal. Samples were irradiated at a dose rate of 1.83 kGy/hr to a total dose of 45 kGy at 4° C.

Monoclonal immunoglobulin activity was determined by a standard ELISA protocol. Maxisorp plates were coated with human recombinant insulin at 2.5 µg/ml overnight at 4° C. The plate was blocked with 200 µl of blocking buffer (PBS, pH 7.4, 2% BSA) for two hours at 37° C. and then washed six times with wash buffer (TBS, pH 7, 0.05% TWEEN 20). Samples were re-suspended in 500 µl of high purity water (100 ng/µl), diluted to 5 µg/ml in a 300 µl U-bottomed plate coated for either overnight or two hours with blocking buffer. Serial 3-fold dilutions were performed, with a final concentration of 0.0022 µg/ml. Plates were incubated for one hour at 37° C. with agitation and then washed six times with a wash buffer. Phosphatase-labelled goat anti-mouse IgG (H+L) was diluted to 50 ng/ml in binding buffer and 100 µl was added to each well. The plate was incubated for one hour at 37° C. with agitation and washed six times with wash buffers. 100 µl of Sigma-104 substrate (1 mg/ml in DEA buffer) was added to each well and reacted at room temperature. The plate was read on a Multiskan MCC/340 at 405 nm with the background absorbance at 620 nm subtracted.

Results

Freeze-dried anti-insulin monoclonal immunoglobulin, supplemented with 1% BSA, gamma irradiated to 45 kGy resulted in an average loss in activity of 1.5 fold (average loss in avidity of 33%, data not shown). Samples irradiated to 45 kGy in the presence of diosmin showed ~62% recovery of activity and those irradiated to 45 kGy in the presence of silymarin showed ~77% recovery of activity.

Example 33

In this experiment, the protective effects of a combination of 200 µM Silymarin+200 mM ascorbate+200 µM Trolox (silymarin cocktail) and a combination of 200 µM Diosmin+ 200 mM ascorbate+200 µM Trolox (diosmin cocktail), on gamma irradiated lyophilized human hemophiliac clotting Factor VIII activity were evaluated.

Methods

Aliquots of 200 µl of Baxter monoclonal human Factor VIII (21 IU/vial), alone or in combination with the cocktail of interest, were placed in 2 ml vials, frozen at −80° C., and lyophilized. Gamma irradiation to 45 kGy was performed at a dose rate of 1.9 kGy/hr at 4° C. Single-step clotting rates were determined using an MLA Electra 1400C Automatic Coagulation Analyzer (Hemoliance).

Results

Lyophilized Factor VIII irradiated to 45 kGy retained about 18–20% of Factor VIII activity compared to fresh frozen Factor VIII. In contrast, samples containing the diosmin cocktail retained between 40–50% of Factor VIII activity following irradiation to 45 kGy and samples containing the silymarin cocktail retained about 25% of Factor VIII activity following irradiation to 45 kGy.

Example 34

In this experiment, the protective effects of epicatechin and biacalein on gamma irradiated liquid and freeze-dried thrombin were evaluated.

Methods

Samples of thrombin (100 NIH units, 1 ml), alone or in the presence of epicatechin (200 mM) or purpurogallin (1M, Aldrich) or biacalein (50 mM; Aldrich), and 10% bovine serum albumin, were prepared and lyophilized. Lyophilized samples were gamma irradiated to 48.5–51.2 kGy at a dose rate of 1.846–1.949 kGy/hr at 4° C. All samples were then assayed for clotting activity by conventional chromagenic methodology.

Results

Lyophilized thrombin containing epicatechin retained 79.9% of thrombin activity following gamma irradiation, while lyophilized thrombin containing purpurogallin retained over 90% of thrombin activity following gamma irradiation. Lyophilized thrombin containing biacalein retained about 57% of thrombin activity following gamma irradiation.

Example 35

In this experiment, the protective effects of various concentrations of epicatechin on lyophilized thrombin irradiated to 45 kGy were evaluated.

Methods

Samples of thrombin (100 NIH units, 1 ml) were combined with various amounts of epicatechin (20, 40 or 80 mM; Aldrich) and 10% bovine serum albumin in 2 ml vials and then lyophilized. Samples were irradiated to a total dose of 45 kGy at 1.805 kGy/hr at 4° C. Irradiated samples were reconstituted in 50% glycerol and assayed for thrombin activity.

Results

Irradiated samples of thrombin containing 20, 40 or 80 mM epicatechin retained about 76%, 83% and 82%, respectively, of thrombin activity.

Example 36

In this experiment, the protective effects of rutin on gamma irradiated urokinase were evaluated.

Methods

Liquid urokinase (20,000 IU/ml; Sigman U-5004 reconstituted in sterile water-for-injection) was combined with rutin (1.35, 2.7, 27 or 10.8 mM) and gamma irradiated to 45 kGy at a dose rate of 1.92 kGy/hr at 4° C. Samples were assayed for urokinase activity at 37° C. in 100 mM Tris buffer at pH 8.8, with 0.2% PEG and 100 mM NaCl using a colormetric substrate (Calbiochem 672157). Absorbance was measured at 405 nm (with subtraction of the 620 nm signal) at 20 minute intervals, commencing 5 minutes into the assay.

Results

Irradiation without rutin eliminated all activity while samples of liquid urokinase containing rutin retained a greater level of urokinase activity following irradiation to 45 kGy.

Example 37

In this experiment, the protective effect of epicatechin on freeze-dried anti-insulin monoclonal antibody exposed to 45 kGy total dose of gamma irradiation was evaluated.

Materials

1. Anti-human insulin monoclonal antibody(mab) samples: Reconstituted with 500 μl water for 1.5 hr with nutating at 4° C.
2. F96 Maxisorp Immuno Plates: Nalge Nunc International Cat# 442404 Batch 052101.
3. Human recombinant insulin: Sigma 1-0259 lot 89H1195 stock at 5 mg/ml in 10 mM HCL
4. Anti-human Insulin Monoclonal Antibody Purified Clone #7F8: Biodesign International E86102M lot 7125000, 6.72 mg/ml.
5. Carbonate/Bicarbonate Coating Buffer pH 9.4
6. PBS pH 7.4
7. Blocking Buffer: 2%BSA/PBS pH 7.4
8. Wash Buffer: TBST (TBS pH 7.4 with 0.05%Tween20).
9. Round bottom well plates: Nunc 262146 batch 047121.
10. Affinity purified, phosphatase labeled goat anti-mouse IgG (H+L) KPL cat# 475-1806 lot XB 106 0.5 mg/ml in 50% glycerol.
11. Binding buffer: 0.25% BSA/PBS/0.05%Tween 20 pH 7.4
12. Phosphatase Substrate Buffer: DEA Buffer: (per 1 L: 97 mL Diethanolamine (Sigma D-8885), 0.1 g MgCl$_2$.6H$_2$O, 0.02% sodium azide). Store at 4° C.
13. Phosphatase Substrate: (p-nitrophenyl phosphate) Sigma 104–105, 5 mg per tablet. Prepare fresh as a 1 mg/ml solution in phosphatase substrate buffer. This solution is light sensitive and should be stored in the dark until ready to dispense.

Protocol

1. Coated wells of Maxisorp plates (5 plates total) with 100 μl 2.5 μg/ml insulin O/N at 4° C.
2. Washed wells 2–3 times with PBS.
3. Blocked non-specific binding sites by adding full volume of blocking buffer (~380 μl) to all wells and incubated for 2 hours at 37° C. In addition, blocked the non-specific binding sites of two round bottom plates under the same conditions.
4. Washed all wells 3 times with TBST. In the pre-blocked round bottom plates, prepared the dilution series of each anti-insulin mab sample going down the plate.

Removed blocking solution from the round bottom two plates and washed well twice with PBS.

Prepared 600 μl of 5 μg/ml mab sample (mab concentration in sample is 100 μg/ml, so diluted 30 μl sample into 570 μl binding buffer (in 1.5 ml microfuge tubes)).

Added 225 μl of 5 μg/ml mab sample to appropriate Row A of the three plates (see below for sample position and plate #).

Added 150 μl of binding buffer to all wells except Row A (excluding Column 1 and 12).

Made a 3-fold dilution series down the plate by transferring exactly 75 μL from Row A into Row B, mixing 6–8 times and then transferring exactly 75 μL from Row B to Row C, and continued in this way down the entire plate.

Transferred 100 μl of the diluted primary antibody from the U-bottom wells to the appropriate wells on the coated and blocked flat-bottom assay plate.

5. Covered the plates with plate sealers and incubated at 37° C. with shaking (Lab Line Titer Plate shaker set at 3) for 1 hour (went 75 min.).

6. Washed all plates with 3 sets of 2 washes each set using TBST (approximately 5 min interval between each set of washes). Added 100 μl of 50 ng/ml phosphatase-labeled goat anti-mouse antibody diluted into binding buffer to all wells.

1. Covered plate with plate sealer and incubated at 37° C. for one hour with shaking.
2. Washed all plates with 3 sets of 2 washes each set using TBST (approximately 5 min interval between each set of washes).
3. Added 100 μl of 1 mg/ml Sigma 104 phosphatase substrate in DEA buffer to each well.
4. Incubated at ambient temperature with shaking.
5. Determined absorbance at 405 nm, after subtracting the absorbance at 620 nm, after 15 minutes.

Results

Freeze-dried samples containing no stabilizer exhibited a 50% loss of antibody avidity following irradiation to 45 kGy. Freeze-dried samples containing epicatechin exhibited significantly greater antibody avidity following irradiation to 45 kGy.

Example 38

In this experiment, the effect of gamma radiation on dried urokinase suspended in polypropylene glycol (PPG) 400 or phosphate buffered saline (PBS) was determined.

Method

Six 1.5 ml polypropylene microfuge tubes containing urokinase and PPG400 (tubes 2 and 5), PBS (tubes 3 and 6) or dry urokinase alone (tubes 1 and 4) were prepared as indicated in the table below. Tubes 4–6 were gamma irradiated at 45 kGy (1.9 kGy/hr) at 4° C. Tubes 1–3 were controls (4° C.).

| Tube | Sample | weight of dry urokinase (mg) | volume PPG400 (μl) | volume PBS (μl) |
|---|---|---|---|---|
| 1 | dry urokinase alone | 3.2 | 0 | 0 |
| 2 | urokinase suspended in PPG400 | 3.16 | 126 | 0 |
| 3 | urokinase suspended in PBS | 3.08 | 0 | 123 |
| 4 | dry urokinase alone | 3.38 | 0 | 0 |
| 5 | urokinase suspended in PPG400 | 3.3 | 132 | 0 |
| 6 | urokinase suspended in PBS | 3.52 | 0 | 141 |

After irradiation, the samples were centrifuged at room temperature for 5 minutes at 14k RPM. PPG400 solvent was removed from tubes 2 and 5 and 120 μl PBS were added to those two tubes. 128 μl and 135 μl PBS were added to tubes 1 and 4, respectively (urokinase concentration of 40,000 IU/ml). All samples were then diluted 50-fold with PBS and absorbance at 280 nm was determined. 50 μl of each diluted sample were then added to a 96-well microtiter plate, followed by 50 μl of 3 mM substrate in 2× assay buffer. The plates were incubated at 37° C. with shaking and absorption read at both 405 and 620 nm every 20 minutes beginning 5 minutes after substrate addition. The absorption at 630 nm (background) was subtracted from the value at 405 nm to obtain a corrected absorption value. The final concentration of urokinase was 1000 IU/ml.

Materials

Urokinase—Sigma cat. # U-5004, lot 29H1054; 2.5 mg=4000 IU Urokinase.

PPG400—Fluka cat. # 81350.

Substrate—urokinase substrate 1, colormetric—Calbiochem. cat. # 672157, lot B23901, 5 mg vials, final concentration 1.5 mM.

2× Assay Buffer—100 mM Tris (pH 8.8), 100 mM NaCl, 0.2% PEG8000.

Results

Urokinase suspended in PPG400 and then gamma irradiated to a total dose of 45 kGy maintained the same percent activity as gamma irradiated dry powder urokinase (80%). In contrast, urokinase suspended in PBS subjected to the same gamma irradiation maintained only 6% activity.

Example 39

In this experiment, the activity (as shown by the ability to bind antigen) of immobilized anti-insulin monoclonal antibody was determined after irradiation in the presence of various forms of polypropylene glycol (molecular weights of 400, 1200 and 2000).

Method

In two 96-well microtiter plates (falcon plates—ProBind polystyrene cat. # 353915), the wells were washed four times with full volume PBS (pH 7.4). Once the two plates were prepared as described above, they were coated with 100 µl/well of freshly prepared 2 µg/ml anti-insulin in coating buffer and left overnight at 4° C. The plates were then washed briefly three times with PBS (pH 7.4) and 100 µµl of PPG400, PPG1200 or PPG2000 were added to specific wells. Each solution was prepared in a 11, i.e., 2-fold, dilution series with PBS. Both plates were covered tightly with a cap mat (Greiner cap mat cat. # 381070 (USA Scientific)) and irradiated at either 0 kGy/hr or 45 kGy (1.92 kGy/hr), both at 4° C.

Following irradiation, approximately 380 µl full volume blocking buffer were then added to all wells and the plates were incubated for two hours at 37° C. The plates were washed four times with TBST and 100 µl of 50 ng/ml biotin-labelled insulin in binding buffer were added to each well. The plates were covered with a plate sealer (Dynatech acetate plate sealers) and incubated at 37° C. with shaking (LabLine Titer Plate Shaker set at 3) for 1.5 hours. The plates were washed four times with TBST and 100 µl of 0.5 µg/ml phosphatase-labelled streptavidin in binding buffer were added to each well. The plates were covered with a plate sealer and incubated at 37° C. for one hour with shaking. The plates were then washed four times with TBST and 100 µl of 1 mg/ml phosphatase substrate in DEA buffer were added to each well and the plates were incubated at 37° C. with shaking. Absorption was read at both 405 and 620 nm at 5 minute intervals as needed. The absorption at 630 nm (background) was subtracted from the value at 405 nm to obtain a corrected absorption value.

Materials

Blocking buffer—2% BSA/PBS (pH 7.4).

TBST—Tris Buffered Saline (pH 7.4) with 0.05% Tween 20.

Biotin-Labelled Insulin—from bovine pancreas—Sigma 1–2258 lot 110H8065, 5 mg insulin, 1.2 mol. FITC per mol. insulin, reconstituted in 5 ml sterile water at 1.0 mg/ml stored at 4° C.

Binding Buffer—0.25% BSA/PBS (pH 7.4).

Phosphatase-Labelled Streptavidin—KPL cat. # 15-30-00; 0.5 mg/ml in 50% glycerol/$H_2O$ (stock diluted 1:1000).

DEA Buffer—per 1 L—97 ml diethanolamine (Sigma D-8885), 0.1 g $MgCl_2.6H_2O$, 0.02% sodium azide, stored at 4° C.

Phosphatase Substrate—p-nitrophenyl phosphate—Sigma 104–105, 5 mg/tablet. The phosphatase substrate was prepared fresh as a 1 mg/ml solution in phosphatase substrate buffer, i.e., DEA buffer. The solution is light sensitive so it had to be stored in the dark until ready to dispense.

Monoclonal IgG1 anti-Human Insulin—Biodesign Int. cat. # E86102M, lot 8J2877.

Coating Buffer—carbonate/bicarbonate (pH 9.4).

Polypropylene glycol P400 —Fluka cat. # 81350.

Polypropylene glycol P1200 —Fluka cat. # 81370.

Polypropylene glycol P2000 —Fluka cat. # 81380.

Results

Irradiated samples containing PPG exhibited approximately 50–63% of binding activity of unirradiated control. In contrast, irradiated samples containing PBS exhibited no binding activity.

Example 40

In this experiment, liquid thrombin containing 50% glycerol and spiked with porcine parvovirus (PPV) was irradiated to varying total doses of radiation.

Method

1. Add 100 µl 100% glycerol, 20 µl thrombin (100 U/ml thrombin) spiked with 50 µl PPV and optionally 20 µl (200 mM) sodium ascorbate as a stabilizer (adjusted to a total volume of 1 ml with $H_2O$) to Wheaton 3 ml tubes (in duplicate), and irradiate to a total dose of 10, 30 or 45 kGy at 1.8 kGy/hr at 4° C.

2. Label and seed 96-well cell culture plates to allow at least 4 well per dilution (seeding to be done one day before inoculation). Add 200 µl of cell suspension per well at a concentration of $4×10^4$/ml. The same cell culture medium is used for cell growth and maintenance after virus inoculation.

3. Perform virus inoculation when the cells sheets are 70–90% confluent. In this experiment 800 µl PK-13 growth media was added to 200 ul samples first.

4. Make appropriate dilution (1:5) of samples with PK-13 growth media, then filter sterilize each sample using low-protein-binding disc filters.

5. Add 50 µl of the pre-diluted sample to column 1 of a 96-well plate. In column 1 mix the medium and the sample together by pipetting up and down 4–5 times. With fresh tips transfer the necessary amount (50 µl) to the next column and repeat the mixing process. Empty all the liquid out of the tips and using the same set of tips, transfer the sample to the next column. Repeat this process in each column until column 12 is reached. When the sample in column 12 is mixed, empty the liquid out of the tips, withdraw the sample amount and dispose of this extra liquid in a waste bottle. This gives you 12 samples dilutions.

6. Return plates to the incubator at 37° C.

7. Observe microscopically and record the cytopathic effect in inoculated cultures on day 4–5 and day 7. The $TCID_{50}$ is calculated from CPE reading according to the method of Karber.

8. Positive controls were done by adding 50 µl PPV infecting stock, and negative controls were done by adding 50 µl PK-13 growth media followed by serial 1:5 dilutions.

Materials

Wheaton tubes—glass serum vials, Wheaton # 223684, lot # 1154132-02.

Thrombin—bovine origin, 5000 US Units (5000 U/ml stock).

Sodium Ascorbate—Aldrich Chem. Co. cat. # 26,855-0 (Milw, WI 53201).

Porcine Parvovirus (PPV)—ATCC # VR-742; PPV infecting stock was prepared by PEG8000 preparation wherein ⅕ volume of PEG8000 (20% in 2.5 M NaCl) was added to PPV and incubated at refrigerated temperatures for 24 hours after which, PPV was pelleted by 15,000 rpm for 45 minutes in a Beckman SW-28 rotor, and resuspended in ¹⁄₁₀ volume of PEG buffer. PPV titer of porcine parvovirus was determined by $TCID_{50}$ and was about 9.0 log/ml (032301 stock). PPV spike ratio was 1:4 (50 μl PPV stock mixed with 150 μl protein solution) into liquid thrombin.

PEG Buffer—0.1 M NaCl, 0.01 M Tris (pH 7.4), 1 mM EDTA.

Siliconized stoppers were used in the experiment obtained from American Stemli (Princeton, N.J.), 6720GC rubber formulation, lot # G009/7202.

Cells—PK-13 (ATCC # CRL-6489), passage # 14. Cells are maintained in PK-13 growth medium (Dulbecco's modified Eagle medium supplemented with 10% FBS and IX penicillin/streptomycin/L-glutamine).

Results

| Sample | $TCID_{50}$ Titer per 0.05 ml | Log Reduction |
| --- | --- | --- |
| 0 kGy/+200 mM sodium ascorbate | 6.29 | |
| 0 kGy/no stabilizer | 6.375 | |
| 10 kGy/+200 mM sodium ascorbate | 4.97 | 1.32 |
| 10 kGy/no stabilizer | 2.97 | 3.405 |
| 30 kGy/+200 mM sodium ascorbate | 3.05 | 3.24 |
| 30 kGy/no stabilizer | 2.35 | 4.025 |
| 45 kGy/+200 mM sodium ascorbate | 3.05 | 3.24 |
| 45 kGy/no stabilizer | 3.05 | 3.325 |

With a 10 kGy total dose, there was a 1.32 log and a 3.405 log reduction in PPV levels in the presence and absence of sodium ascorbate, respectively. Similarly, with a 30 kGy total dose, there was a 3.24 log and a 4.025 log reduction in PPV levels in the presence or absence, respectively, of sodium ascorbate. With a 45 kGy total dose, there was a 3.24 log and a 3.325 log reduction in PPV levels with or without ascorbate, respectively. This experiment demonstrates that inactivation of even small non-enveloped viruses is effective in the presence of a non-aqueous solvent both with and without an effective stabilizer.

Example 41

In this experiment, trypsin suspended in polypropylene glycol 400 was subjected to gamma irradiation at varying levels of residual solvent (water) content.

Method

Trypsin was suspended in polypropylene glycol 400 at a concentration of about 20,000 U/ml and divided into multiple samples. A fixed amount of water (0%, 1%, 2.4%, 4.8%, 7%, 9%, 10%, 20%, 33%) was added to each sample; a 100% water sample was also prepared which contained no PPG 400.

Samples were irradiated to a total dose of 45 kGy at a rate of 1.9 kGy/hr and a temperature of 4° C. Following irradiation, each sample was centrifuged to pellet the undissolved trypsin. The PPG/water soluble fraction was removed and the pellets resuspended in water alone for activity testing.

Assay conditions: 5 U/well trypsin (50 U/ml)+BAPNA substrate (0.5 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Signma Plot using the hyperbolic rectangular equation).

Results

The irradiated samples containing a mixture of polypropylene glycol (PPG 400) and water (up to 33% water) retained about 80% of the activity of an unirradiated trypsin control and activity equal to that of a dry (lyophilized) trypsin control irradiated under identical conditions. No activity was detected in the 100% water sample irradiated to 45 kGy.

Example 42

In this experiment, porcine heart valves were gamma irradiated in the presence of polypropylene glycol 400 (PPG400) and, optionally, a scavenger, to a total dose of 30 kGy (1.584 kGy/hr at −20° C.).

Materials

Tissue—Porcine Pulmonary Valve (PV) Heart valves were harvested prior to use and stored.

Tissue Preparation Reagents—

Polypropylene Glycol 400. Fluka, cat# 81350 lot# 386716/1

Trolox C. Aldrich, cat# 23,881-3 lot# 02507TS

Coumaric Acid. Sigma, cat# C-9008 lot# 49H3600 n-Propyl Gallate. Sigma, cat# P-3130 lot# 117H0526

α-Lipoic Acid. CalBiochem, cat# 437692 lot# B34484

Dulbecco's PBS. Gibco BRL cat# 14190-144 lot# 1095027

2.0 ml Screw Cap tubes. VWR Scientific Products, cat# 20170-221 lot# 0359

Tissue Hydrolysis Reagents—

Nerl $H_2O$. NERL Diagnostics cat# 9800-5 lot# 03055151

Acetone. EM Science cat# AX0125-5, lot# 37059711

6 N constant boiling HCl. Pierce cat# 24309, lot# BA42184

Int-Pyd (Acetylated Pyridinoline) HPLC Internal Standard. Metra Biosystems Inc. cat# 8006, lot# 9

Hydrochloric Acid. VWR Scientific cat# VW3110-3, lot# n/a

Heptafluorobutyric Acid (HFBA) Sigma cat# H-7133, lot# 20K3482

FW 214.0 store at 2–8° C.

SP-Sephadex C-25 resin. Pharmacia cat# 17-0230-01, lot# 247249 (was charged with NaCl as per manufacturer suggestion)

Hydrolysis vials—10 mm×100 mm vacuum hydrolysis tubes. Pierce cat# 29560, lot #BB627281

Heating module—Pierce, Reacti-therm. Model # 18870, S/N 1125000320176

Savant—Savant Speed Vac System:
1. Speed Vac Model SC110, model # SC110-120, serial # SC110-SD171002-1H
   a. Refrigerated Vapor Trap Model RVT100, model # RVT100-120V, serial # RVT1OO-58010538-1B
   b. Vacuum pump, VP 100 Two Stage Pump Model VP100, serial # 93024

Column—Phenomenex, Luna 5 μ C18(2) 100 Å, 4.6×250 mm. Part # OOG-4252-EO, S/N# 68740-25, B/N# 5291-29

HPLC System:

Shimadzu System Controller SCL-10A

Shimadzu Automatic Sample Injector SIL-10A (50 µl loop)

Shimadzu Spectrofluorometric Detector RF-10A

Shimadzu Pumps LC-10AD

Software—Class-VP version 4.1

Low-binding tubes—MiniSorp 100×15 Nunc-Immunotube. Batch # 042950, cat# 468608

Methods

A. Preparation of Stabilizer Solutions

Trolox C

MW=250; therefore, want 250 mg/ml for 1M or 125 mg/ml for 0.5 M actual weight=250.9 mg 250÷125 mg/ml=2.0 ml Not soluble; therefore an additional 2 ml of PPG was added. After water bath sonication and time, Trolox C is soluble at 125 mM.

Coumaric Acid

MW=164; therefore, 164 mg/ml for 1 M actual weight=164.8 mg 164.8 mg÷164 mg/ml=1.0 ml Water bath sonicated for approximately 15 minutes—not 100% soluble. An additional 1 ml PPG was added and further water bath sonicated.

n-Propyl Gallate

MW=212.2; therefore, 212 mg/ml for 1M or 106 mg/ml for 0.5 M actual weight=211.9 mg 211.9 mg÷106 mg/ml=2.0 ml Soluble after a 20–30 minute water bath sonication.

1 M α-Lipoic Acid

MW=206; therefore, 206 mg/ml actual weight=412 mg 412 mg÷206 mg/ml=2.0 ml

Very soluble after 10 minute water bath sonication.

Final Stocks of Scavengers 125 mM Trolox C—4 ml

1 M Lipoic Acid—2 ml 0.5 M Coumaric acid—2 ml 0.5 M n-Propyl Gallate—2 ml

B. Treatment of Valves Prior to Gamma-Irradiation

1. PV heart valves were thawed on wet ice.
2. Cusps were dissected out from each valve and pooled into 50 ml conical tubes containing cold Dulbecco's PBS.
3. Cusps were washed in PBS at 4° C. for approximately 1.5 hrs; changing PBS during that time a total of 6×.
4. 2 cusps were placed in each 2 ml screw cap tubes.
5. 1.2 ml of the following were added to two tubes (for 0 and 30 kGy):

PPG 125 mM Trolox C in PPG

SCb stabilizer—comprising of 1.5 ml 125 mM Trolox C, 300 µl 1 M Lipoic Acid, 600 µl 0.5 M Coumaric Acid and 600 µl 0.5 M n-Propyl Gallate. (Final concentrations: 62.5 mM, 100 mM, 100 mM and 100 mM, respectively.)

6. Tubes were incubated at 4° C., with rocking.
7. Stabilizer solutions and cusps were transferred into 2 ml glass vials for gamma-irradiation.
8. All vials were frozen on dry ice.
9. Control samples were kept in-house at −20° C.

C. Gamma-Irradiation of Tissue

Samples were irradiated at a rate of 1.584 kGy/hr at −20° C. to a total dose of 30 kGy.

D. Processing Tissue for Hydrolysis/Extraction

1. Since PPG is viscous, PBS was added to allow for easier transfer of material.
2. Each pair of cusps (2 per condition) were placed into a 50 ml Falcon tube filled with cold PBS and incubated on ice—inverting tubes periodically.
3. After one hour PBS was decanted from the tubes containing cusps in PPG/0 and 30 and replenished with fresh cold PBS. For the PPG samples containing Trolox C or stabilizer cocktail, fresh 50 ml Falcon tubes filled with cold PBS were set-up and the cusps transferred.
4. An additional 3 washes were done.
5. One cusp was transferred into a 2 ml Eppendorf tube filled with cold PBS for extraction. The other cusp was set-up for hydrolysis.

E. Hydrolysis of Tissue

Hydrolysis of Tissue

1. Each cusp was washed 6× with acetone in an Eppendorf tube (approximately 1.5 ml/wash).
2. Each cusp was subjected to SpeedVac (with no heat) for approximately 15 minutes or until dry.
3. Samples were weighed, transferred to hydrolysis vials and 6 N HCl added at a volume of 20 mg tissue/ml HCl:

| Sample ID | Dry Weight (mg) | µl 6 N HCl |
|---|---|---|
| 1. PPG/0 | 6.49 | 325 |
| 2. PPG/30 | 7.26 | 363 |
| 3. PPG T/0 | 5.80 | 290 |
| 4. PPG T/30 | 8.20 | 410 |
| 5. PPG SCb/0 | 6.41 | 321 |
| 6. PPG SCb/30 | 8.60 | 430 |

4. Samples were hydrolyzed at 110° C. for approximately 23 hours.
5. Hydrolysates were transferred into Eppendorf tubes and centrifuged @ 12,000 rpm for 5 min.
6. Supernatent was then transferred into a clean Eppendorf.
7. 50 µl of hydrolysate was diluted in 8 ml Nerl $H_2O$ (diluting HCl to approximately 38 mM).
8. Spiked in 200 µl of 2× int-pyd. Mixed by inversion. (For 1600 µl 2×int-pyd:160 µl 20×int-pyd+1440 µl Nerl $H_2O$.)
9. Samples were loaded onto SP-Sephadex C25 column (approximately 1×1 cm packed bed volume) that had been equilibrated in water. (Column was pre-charged with NaCl)
10. Loaded flow through once again over column.
11. Washed with 20 ml 150 mM HCl.
12. Eluted crosslinks with 5 ml 2 N HCl into a low binding tube.
13. Dried entire sample in Savant.

F. Analysis of Hydrolysates

Set-up the Following

| Sample | µl | µl $H_2O$ | µl HFBA |
|---|---|---|---|
| 1. PPG/0 kGy | 18 | 180 | 2 |
| 2. PPG/30 kGy | 59 | 139 | 2 |
| 3. PPG T/0 kGy | 67 | 171 | 2 |
| 4. PPG T/30 kGy | 64 | 134 | 2 |
| 5. PPG SCb/0 kGy | 10 | 188 | 2 |
| 6. PPG SCb/30 kGy | 32 | 166 | 2 |

Results

In the presence of PPG 400, the results were nearly identical whether the heart valve had been irradiated or not.

The addition of a single stabilizer (trolox C) or a stabilizer mixture produced even more effective results. The gel analysis confirmed the effectiveness of the protection provided by these conditions.

Example 43

In this experiment, the effects of gamma irradiation were determined on porcine heart valve cusps in the presence of 50% DMSO and, optionally, a stabilizer, and in the presence of polypropylene glycol 400 (PPG400).

Preparation of Tissue for Irradiation 1. 5 vials of PV and 3 vials of atrial valves (AV) were thawed on ice.
2. Thaw media was removed and valves rinsed in beaker filled with PBS.
3. Transferred each valve to 50 ml conical containing PBS. Washed by inversion and removed.
4. Repeated wash 3×.
5. Dissected out the 3 cusps (valves).
6. Stored in PBS in 2 ml screw top Eppendorf Vials (Eppendorfs) and kept on ice.

Preparation of Stabilizers

All stabilizers were prepared so that the final concentration of DMSO was 50%.

1 M Ascorbate in 50% DMSO

Aldrich cat# 26,855-0 lot# 10801HU 200 mg dissolved in 300 µl $H_2O$. Add 500 µl DMSO. The volume was adjusted to 1 ml with $H_2O$. Final pH was 8.0

1 M Coumaric Acid

Sigma cat# C-9008 lot# 49H3600. MW 164.2

Dissolve 34.7 mg in 106 µl DMSO, pH=≈3.0

138 µl $H_2O$ was added. Sample crashed out.

Coumaric went back into solution once pH was adjusted to 7.5 with 1 N NaOH.

1 M n-Propyl Gallate

Sigma cat# P-3130 lot# 117H0526. MW 212.2

Dissolve 58.2 mg in 138 µl DMSO.

Add 138 µl $H_2O$. Final pH is 6.5 or slightly lower.

Stabilizer Mixture 1.0 ml 500 mM Ascorbate
500 µl 1 M Coumaric Acid
300 µl 1 M n-propyl gallate
1.2 ml 50% DMSO
3.0 ml Method 1. 6 ml of a solution (stabilizer mixture or PPG400) was added to each sample and then the sample was incubated at 4° C. for 2.5 days. Valves and 1 ml of the solution in which they were incubated were then transferred into 2 ml irradiation vials. Each sample was irradiated with gamma irradiation at a rate of 1.723 kGy/hr at 3.6° C. to a total dose of 25 kGy.

Hydrolysis of Tissue

1. Washed each cusp 6× with acetone in a 2 ml Eppendorf Vial.
2. After final acetone wash, dried sample in Savant (without heat) for approximately 10–15 minutes or until dry.
3. Weighed the samples, transferred them to hydrolysis vials and then added 6 N HCl at a volume of 20 mg tissue/ml HCl:

| Sample ID | Dry Weight (mg) | µl 6 N HCl |
|---|---|---|
| 1. PBS/0 kGy | 11.4 | 570 |
| 2. PBS/25 kGy | 6.0 | 300 |
| 3. DMSO/0 kGy | 6.42 | 321 |
| 4. DMSO/25 kGy | 8.14 | 407 |
| 5. DMSO/SC-a/kGy | 8.7 | 435 |
| 6. DMSO/SC-a/25 kGy | 8.15 | 408 |
| 7. PPG/0 kGy | 13.09 | 655 |
| 8. PPG/25 kGy | 10.88 | 544 |

5. Samples were hydrolyzed at 110° C. for approximately 23 hours.
6. Hydrolysates were transferred into Eppendorf vials and centrifuged at 12,000 rpm for 5 min.
7. Supernatent was transferred into a clean Eppendorf vial.
8. 50 µl hydrolysate was diluted in 8 ml Nerl $H_2O$ (diluting HCl to approximately 37 mM).
9. Spiked in 200 µl of 2×int-pyd. Mixed by inversion. (For 2000 µl 2×int-pyd: 200 µl 20×int-pyd+1.8 ml Nerl $H_2O$.)
10. Samples were loaded onto SP-Sephadex C25 column (approximately 1×1 cm packed bed volume) that had been equilibrated in water. (Column was pre-charged with NaCl)
11. Loaded flow through once again over column.
12. Washed with 20 ml 150 mM HCl.
13. Eluted crosslinks with 5 ml 2 N HCl into a low binding tube. 50 ml 2 N HCl: 8.6 ml concentrated HCl adjusted to a volume of 50 ml with Nerl $H_2O$.
14. Dried entire sample in Savant.

Guanidine HCl Extraction and DEAE-Sepharose Purification of Proteoglycans

4M Guanidine HCl Extraction

1. Removed all three cusps from gamma irradiation vial and transferred to separate 50 ml conical tube.
2. Washed cusps five times with 50 ml dPBS (at 4° C. over approx. 5 hours) and determined wet weight of one cusp after damping on Kimwipe.
3. Transferred one cusp from each group to 1.5 ml microfuge tube and added appropriate volume of 4M guanidine HCl/150 mM sodium acetate buffer pH 5.8 with 2 µg/ml protease inhibitors (aprotinin, leupeptin, pepstatin A) to have volume to tissue ratio of 15 (see Methods in Enzymology Vol. 144 p.321—for optimal yield use ratio of 15 to 20).
4. Diced cusps into small pieces with scissors.
5. Nutated at 4° C. for ~48 hours.
6. Centrifuged at 16,500 RPM on Hermle Z-252M, 4° C.×10 min.
7. Collected guanidine soluble fraction and dialyze against PBS in 10K MWCO Slide-A-Lyzer overnight against 5 L PBS (3 slide-a-lyzers with one 5L and 5 slide-a-lyzers in another 5L) to remove guanidine.
8. Changed PBS and dialyzed for additional 9 hours at 4° C. with stirring.
9. Collected the dialysate and store at 4° C.
10. Centrifuged at 16,500 RPM on Hermle Z-252M, 4° C.×5 min
11. Removed PBS soluble fraction for DEAE-Sepharose chromatography.

DEAE-Sepharose Chromatography

1. Increase the NaCl concentration of 500 µl of PBS soluble guanidine extract to 300 mM NaCl (Assumed PBS soluble fractions were already at ~150 mM NaCl, so added 15 µl 5M NaCl stock to each 500 µl sample).
2. Equilibrated ~1 ml of packed DEAE-Sepharose (previously washed with 1M NaCl/PB pH 7.2) into 300 mM NaCl/PB pH 7.2 (Note: To make 300 mM NaCl/PB pH7.2—added 3 ml of 5M NaCl stock to 100 ml PBS).

3. Added 200 μl of 1:1 slurry of resin to 515 μl of GuHCl extracts (both at 300 mM NaCl).
4. Nutated at ambient temperature for one hour.
5. Centrifuged gently to pellet resin.
6. Removed "unbound" sample and stored at −20° C.
7. Washed resin 5 times with 1.5 ml of 300 mM NaCl/PBS, pH=7.2.
8. After last wash, removed all extra buffer using a 100 μl Hamilton syringe.
9. Eluted at ambient temperature with three 100 μl volumes of μM NaCl/PB pH 7.2. Stored at −20° C.

SDS-PAGE

5–20% gradient gels for analysis of PBS soluble Guanidine HCl extracts and DEAE-Sepharose chromatography.

1. Gel#1: GuHCl extracts/PBS soluble fractions—Toluidine blue and then Coomassie blue stained.
2. Gel#2: DEAE-Sepharose Eluant Fraction#1—Toluidine Blue stained then Coomassie Blue stained.

Quantification of Collagen Crosslinks by HPLC

1. Prepare 100–200 μl 1× solution in 1% heptafluorobutyric acid (HFBA).
2. Inject 50 μl on C18 HPLC column equilibrated with mobile phase.
3. Spectrofluorometer is set for excitation at 295 nm and emission at 395 nm.
4. Calculate the integrated fluorescence of Internal-Pyridinoline (Int-Pyd) per 1 μl of 1× solution of Int-Pyd.

Results

According to HPLC, the major peak represents the Internal-Pyridinoline (int-Pyd) peak. Irradiation in an aqueous environment (PBS) produced pronounced decreases in the smaller peaks. Reduction of the water content by the addition of a non-aqueous solvent (PPG 400) produced a nearly superimposable curve. DMSO was less effective, while DMSO plus a mixture of stabilizers was more effective at preserving the major peak although some minor peaks increased somewhat. The area under the pyd peak for each sample was calculated as shown in the table below. These results confirm the above conclusions and show that the amino acid crosslinks (pyd) found in mature collagen are effectively conserved in the samples containing PPG and DMSO with a scavenger mixture. Gel analysis reflected the major conclusions from the HPLC analysis, with significant loss of bands seen in PBS and retention of the major bands in the presence of non-aqueous solvents.

| Sample | Area of Pyd Peak |
| --- | --- |
| PBS/ 0 kGy | 94346 |
| PBS/ 25 kGy | 60324 |
| DMSO/ 0 kGy | 87880 |
| DMSO/ 25 kGy | 49030 |
| DMSO/ SCa/ 0 kGy | 75515 |
| DMSO/ SCa/ 25 kGy | 88714 |
| PPG/ 0 kGy | 99002 |
| PPG/ 25 kGy | 110182 |

Example 44

In this experiment, frozen porcine AV heart valves soaked in various solvents were gamma irradiated to a total dose of 30 kGy at 1.584 kGy/hr at −20° C.

Materials

1. Porcine heart valve cusps were obtained and stored at −80° C. in a cryopreservative solution (Containing Fetal calf serum, Penicillin-Streptomycin, Ml 99 media, and approximately 20% DMSO).
2. Dulbecco's Phosphate Buffered Saline: Gibco BRL cat#14190-144 lot 1095027
3. 2 ml screw cap vials: VWR cat# 20170-221 lot #0359
4. 2 ml glass vials: Wheaton cat# 223583 lot#370000-01
5. 13 mm stoppers: Stelmi~6720GC lot#G006/5511
6. DMSO: JT Baker cat# 9224-01 lot# H406307. Sodium ascorbate: Aldrich cat# 26,855-0 lot 10801HU; prepared as a 2M stock in Nerl water.
7. Fetal calf serum
8. Fetal calf serum
9. Penicillin-Streptomycin
10. M199 media
11. DMSO Methods:

Cryopreservative Procedure

Preparation of Solutions

Freeze Medium:

Fetal calf serum (FCS) (10%)=50 ml
Penicillin-Streptomycin=2.5 ml
M199=QS 500 ml
2M DMSO
DMSO=15.62 g
Freeze Medium=QS 100 ml
3M DMSO
DMSO=23.44 g
Freeze Medium=QS 100 ml 1. Place dissected heart valves (with a small amount of conduit/muscle attached) into glass freezing tubes (label with pencil).
2. Add 2 ml of freeze medium.
3. At 21° C., add 1 ml 2M DMSO solution.
4. At 5 minutes, add 1 ml 2M DMSO solution.
5. At 30 minutes, add 4 ml 3M DMSO solution.
6. At 45 minutes and 4° C., place freezing tubes on ice.
7. At 50 minutes and −7.2° C., seed bath.
8. At 55 minutes and −7.2° C., nucleate.
9. At 70 minutes, cool to −40° C. at 1° C./minute. Remove from bath and place in canister of $LN_2$, and store in cryogenic storage vessel.

Procedure for Irradiation of Heart Valves

1. Thawed AV heart valve cusps on wet ice.
2. Pooled cusps into 50 ml tubes.
3. Washed cusps with 50 ml dPBS at 4° C. while nutating. Changed PBS 5× over the course of 5 hrs.
4. Transferred cusps into 2 ml screw cap tubes (2 cusps/tube).
5. Added 1.0 ml of the following to two of each of two tubes: dPBS, 50% DMSO and 50% DMSO with 200 mM sodium ascorbate (2M sodium ascorbate stock was diluted as follows: 400 μl (2M)+1.6 ml water+2 ml 100% DMSO).
6. Incubated tubes at 4° C. with nutating for 46 hours.
7. Transferred solutions and cusps to glass 2 ml vials, stoppered and capped.
8. All vials were frozen on dry ice.
9. Frozen samples were then irradiated at −20° C. at a rate of 1.584 kGy/hr to a total dose of 30 kGy.

Results

According to HPLC analysis, irradiation in an aqueous environment (PBS) produced decreases in the smaller peaks. Reduction of the water content by the addition of a non-aqueous solvent (20% DMSO) reproduced these peaks more faithfully. Increasing the DMSO concentration to 50% was slightly more effective, while DMSO plus a mixture of stabilizers was very effective at preserving both the major and minor peaks. Gel analysis reflected the major conclusions from the HPLC analysis, with significant loss of bands seen in PBS and retention of the major bands in the presence of non-aqueous solvents with and without stabilizers.

Example 45

In this experiment, frozen porcine AV heart valves soaked in various solvents were gamma irradiated to a total dose of 45 kGy at approximately 6 kGy/hr at −70° C.

Materials

1. Porcine heart valve cusps were obtained and stored at −80° C. in a cryopreservative solution (Same solution as that in Example 44).
2. Dulbecco's Phosphate Buffered Saline: Gibco BRL cat#14190-144 lot 1095027
3. 2 ml screw cap vials: VWR cat# 20170-221 lot #0359
4. 2 ml glass vials: Wheaton cat# 223583 lot#370000-01
5. 13 mm stoppers: Stelmi 6720GC lot#G006/5511
6. DMSO: JT Baker cat# 9224-01 lot# H40630
7. Sodium ascorbate: Aldrich cat# 26,855-0 lot 10801HU; prepared as a 2M stock in Nerl water.
8. Polypropylene glycol 400 (PPG400): Fluka cat#81350 lot#386716/1

Methods

Cryopreservative Procedure is the same as that shown in Example 44.

1. Thawed AV heart valve cusps on wet ice. Dissected out cusps and washed the pooled cusps 6× with cold PBS.
2. Dried each cusp and transferred cusps into 2 ml screw cap tubes (2 cusps/tube).
3. Added 1.2 ml of the following to two of each of two tubes: dPBS, dPBS with 200 mM sodium ascorbate, PPG400, PPG400 for rehydration, 50% DMSO and 50% DMSO with 200 mM sodium ascorbate (2M sodium ascorbate stock was diluted as follows: 400 μl (2M)+1.6 ml water+2 ml 100% DMSO).
4. Incubated tubes at 4° C. with nutating for ~46 hours.
5. Replaced all solutions with fresh (with the following exception: for one PPG400 set, PPG400 was removed, the cusp washed with PBS+200 mM ascorbate, which was then removed and replaced with fresh PBS+200 mM ascorbate).
6. Incubated tubes at 4° C. with nutating for 46 hours.
7. Changed the solution on the PPG400 dehyd./PBS+ascorbate rehydration cusps prepared in step 5).
8. Incubated tubes at 4° C. with nutating for ~6 hours.
9. Transferred solutions and cusps to glass 2 ml vials, stoppered and capped.
10. All vials were frozen on dry ice.
11. Frozen samples were then irradiated at −70° C. at a rate of 6 kGy/hr to a total dose of 45 kGy.

Results

According to HPLC analysis irradiation in an aqueous environment (PBS) resulted in changes in the minor peaks and a right shift in the major peak. The inclusion of various non-aqueous solvents, reduction in residual water, and the addition of stabilizers produced profiles that more closely matched those of the corresponding controls. Gel analysis showed a significant loss of bands in PBS, while the other groups demonstrated a significant retention of these lost bands.

When comparing the results from Example 45 to the results from Examples 42, 43, and 44, it becomes apparent that lowering the temperature for the gamma irradiation usually results in a decrease in the amount of modification or damage to the collagen crosslinks. One illustration of this temperature dependence is the sample containing 50% DMSO and ascorbate, in which the additional peaks are markedly decreased as the temperature is lowered from −20° C. to −80° C.

Example 46

In this experiment, the protective effect of the dipeptide Gly—Gly (20 mM) on gamma irradiated freeze-dried anti-insulin monoclonal immunoglobulin supplemented with 1% human serum albumin (HSA) and 5% sucrose was evaluated.

Methods

Samples were freeze-dried for approximately 64 hours and stoppered under vacuum and sealed with an aluminum, crimped seal. Samples were irradiated at a dose rate of 1.83–1.88 kGy/hr to a total dose of 45.1–46.2 kGy at 4° C.

[258] Monoclonal immunoglobulin activity was determined by a standard ELISA protocol. Maxisorp plates were coated with human recombinant insulin at 2.5 μg/ml overnight at 4° C. The plate was blocked with 200 μl of blocking buffer (PBS, pH 7.4, 2% BSA) for two hours at 37° C. and then washed six times with wash buffer (TBS, pH 7, 0.05% TWEEN 20). Samples were re-suspended in 500 μl of high purity water (100 ng/μl), diluted to 5 μg/ml in a 300 μl U-bottomed plate coated for either overnight or two hours with blocking buffer. Serial 3-fold dilutions were performed, with a final concentration of 0.0022 μg/ml. Plates were incubated for one hour at 37° C. with agitation and then washed six times with a wash buffer. Phosphatase-labelled goat anti-mouse IgG (H+L) was diluted to 50 ng/ml in binding buffer and 100 μl was added to each well. The plate was incubated for one hour at 37° C. with agitation and washed six times with wash buffers. One hundred μl of Sigma-104 substrate (1 mg/ml in DEA buffer) was added to each well and reacted at room temperature. The plate was read on a Multiskan MCC/340 at 405 nm with the 620 nm absorbance subtracted.

Results

Freeze-dried anti-insulin monoclonal immunoglobulin, supplemented with 1% HSA, gamma irradiated to 45 kGy resulted in an average loss in activity of 1.5 fold (average loss in avidity of 33%). Samples irradiated to 45 kGy in the presence of the dipeptide Gly—Gly (20 mM) showed ~100% recovery of activity. Unirradiated samples containing the dipeptide Gly—Gly (20 mM) also showed ~100% recovery of activity.

Adding 5% sucrose to freeze-dried anti-insulin monoclonal immunoglobulin containing 1% HSA resulted in an average recovery of 70% of the activity in the sample irradiated to 45 kGy (average loss in activity of approximately 1.5 fold or approximately 30% loss in avidity). Samples irradiated to 45 kGy in the presence of Gly—Gly showed ~79% recovery of activity.

Similar results have been obtained upon the addition of 20 mM Gly—Gly or the combination of ascorbate (20 mM) and Gly—Gly (20 mM) to another monoclonal IgG biological material of different specificity (anti-Ig Lambda Light Chain).

Example 47

In this experiment, the protective effect of Gly—Gly (20 mM) on lyophilized anti-insulin monoclonal immunoglobulin was evaluated.

Method

In 3 ml glass vials, 1.0 ml total volume containing 100 μg anti-insulin monoclonal immunoglobulin, with 10 mg BSA (1%) and either no stabilizer or the stabilizer of interest was lyophilized. Samples were irradiated with gamma radiation (45 kGy total dose, dose rate 1.83 kGy/hr, temperature 4° C.) and then reconstituted with 1 ml of water. Karl Fischer moisture analysis was performed on the quadruplicate samples that did not contain immunoglobulin.

Immunoglobulin binding activity of independent duplicate samples was determined by a standard ELISA protocol: Maxisorp plates were coated overnight with 2.5 μg/ml insulin antigen. Three-fold serial dilutions of anti-insulin monoclonal immunoglobulin samples starting at 5 μg/ml were used. Goat anti-mouse phosphatase conjugate was used at 50 mg/ml. Relative potency values of irradiated samples compared to their corresponding unirradiated sample were calculated using the parallel line analysis software package (PLA 1.2 from Stegmann Systemberatung). Mass spectroscopy analysis was performed by M-scan, Inc. of Westchester Pa.

Results

Irradiation of lyophilized anti-insulin monoclonal immunoglobulin in the presence of 1% bovine serum albumin resulted in the loss of approximately 30% avidity (relative to unirradiated samples) of the immunoglobulin for its immobilized antigen. The addition of the dipeptide Gly—Gly resulted in recovery of 77–84% avidity.

Similar results have been obtained upon the addition of 200 mM ascorbate or the combination of ascorbate (200 mM) and Gly—Gly (200 mM) to two other monoclonal IgG preparations of different specificity (anti-Ig Lambda Light Chain and anti-IgG1).

Example 48

In this experiment, the protective effect of ascorbate (200 mM), alone or in combination with Gly—Gly (200 mM), on a liquid polyclonal antibody preparation was evaluated.

Method

In 2 ml glass vials, samples of IGIV (50 mg/ml) were prepared with either no stabilizer or the stabilizer of interest. Samples were irradiated with gamma radiation (45 kGy total dose, dose rate 1.8 kGy/hr, temperature 4° C.) and then assayed for functional activity and structural integrity.

Functional activity of independent duplicate samples was determined by measuring binding activity for rubella, mumps and CMV using the appropriate commercial enzyme immunoassay (EIA) kit obtained from Sigma, viz., the Rubella IgG EIA kit, the Mumps IgG EIA kit and the CMV IgG EIA kit.

Structural integrity was determined by gel filtration (elution buffer: 50 mM NaPi, 100 mM NaCl, pH 6.7; flow rate: 1 ml/min; injection volume 50 μl) and SDS-PAGE (pre-cast tris-glycine 4–20% gradient gel from Novex in a Hoefer Mighty Small Gel Electrophoresis Unit running at 125V; sample size: 10 μl).

Results

Functional Activity

Irradiation of liquid polyclonal antibody samples to 45 kGy resulted in the loss of approximately 1 log of activity for rubella (relative to unirradiated samples). The addition of ascorbate alone improved recovery, as did the addition of ascorbate in combination with the dipeptide Gly—Gly.

Similarly, irradiation of liquid polyclonal antibody samples to 45 kGy resulted in the loss of approximately 0.5–0.75 log of activity for mumps. The addition of ascorbate alone improved recovery, as did the addition of ascorbate in combination with the dipeptide Gly—Gly.

Likewise, irradiation of liquid polyclonal antibody samples to 45 kGy resulted in the loss of approximately 1 log of activity for CMV. The addition of ascorbate alone improved recovery, as did the addition of ascorbate in combination with the dipeptide Gly—Gly.

Structural Analysis

Liquid polyclonal antibody samples irradiated to 45 kGy in the absence of a stabilizer showed significant loss of material and evidence of both aggregation and fragmentation. The irradiated samples containing ascorbate or a combination of ascorbate and the dipeptide Gly—Gly exhibited only slight breakdown and some aggregation as demonstrated by gel filtration and SDS-PAGE.

Example 49

In this experiment, the protective effect of ascorbate (20 mM) and/or Gly—Gly (20 mM) on lyophilized anti-insulin monoclonal immunoglobulin irradiated at a high dose rate was evaluated.

Method

Samples were freeze-dried for approximately 64 hours and stoppered under vacuum and sealed with an aluminum, crimped seal. Samples were irradiated at a dose rate of 30 kGy/hr to a total dose of 45 kGy at 4° C.

Monoclonal immunoglobulin activity was determined by a standard ELISA protocol. Maxisorp plates were coated with human recombinant insulin at 2.5 μg/ml overnight at 4° C. The plate was blocked with 200 μl of blocking buffer (PBS, pH 7.4, 2% BSA) for two hours at 37° C. and then washed six times with wash buffer (TBS, pH 7, 0.05% TWEEN 20). Samples were re-suspended in 500 μl of high purity water (100 ng/μl), diluted to 5 μg/ml in a 300 μl U-bottomed plate coated for either overnight or two hours with blocking buffer. Serial 3-fold dilutions were performed, with a final concentration of 0.0022 μg/ml. Plates were incubated for one hour at 37° C. with agitation and then washed six times with a wash buffer. Phosphatase-labelled goat anti-mouse IgG (H+L) was diluted to 50 ng/ml in binding buffer and 100 μl was added to each well. The plate was incubated for one hour at 37° C. with agitation and washed six times with wash buffers. One hundred μl of Sigma-104 substrate (1 mg/ml in DEA buffer) was added to each well and reacted at room temperature. The plate was read on a Multiskan MCC/340 at 405 nm with the 620 nm absorbance subtracted.

Results

Freeze-dried anti-insulin monoclonal immunoglobulin gamma irradiated to 45 kGy resulted in an average loss in activity of ~32% (average loss in avidity of ~1.5 fold). [279] Lyophilized anti-insulin monoclonal immunoglobulin samples irradiated to 45 kGy in the presence of 20 mM ascorbate had only a 15% loss in activity (~1.1 fold loss in avidity), and those samples irradiated to 45 kGy in the presence of 20 mM Gly—Gly had only a 23% loss in activity (~1.3 fold loss in avidity). Lyophilized anti-insulin monoclonal immunoglobulin samples irradiated to 45 kGy in the presence of 20 mM ascorbate and 20 mM Gly—Gly showed no loss in activity (no loss in avidity).

Example 50

In this experiment, the protective effect of ascorbate (200 mM) and/or Gly—Gly (200 mM) on liquid anti-insulin monoclonal immunoglobulin irradiated to 45 kGy.

Method

Liquid samples containing 100 μg antibody (2 mg/ml) with 10% BSA were irradiated at a dose rate of 1.83–1.88 kGy/hr to a total dose of 45.1–46.2 kGy at 4° C.

Monoclonal immunoglobulin activity was determined by a standard ELISA protocol. Maxisorp plates were coated with human recombinant insulin at 2.5 μg/ml overnight at 4° C. The plate was blocked with 200 μl of blocking buffer (PBS, pH 7.4, 2% BSA) for two hours at 37° C. and then washed six times with wash buffer (TBS, pH 7, 0.05% TWEEN 20). Samples were re-suspended in 500 μl of high purity water (100 ng/μl), diluted to 5 μg/ml in a 300 μl U-bottomed plate coated for either overnight or two hours with blocking buffer. Serial 3-fold dilutions were performed, with a final concentration of 0.0022 μg/ml. Plates were incubated for one hour at 37° C. with agitation and then washed six times with a wash buffer. Phosphatase-labelled goat anti-mouse IgG (H+L) was diluted to 50 ng/ml in binding buffer and 100 μl was added to each well. The plate was incubated for one hour at 37° C. with agitation and washed six times with wash buffers. One hundred μl of Sigma-104 substrate (1 mg/ml in DEA buffer) was added to each well and reacted at room temperature. The plate was read on a Multiskan MCC/340 at 405 nm with the 620 nm absorbance subtracted.

Results

Liquid anti-insulin monoclonal immunoglobulin gamma irradiated to 45 kGy resulted in a complete loss of activity.

Liquid anti-insulin monoclonal immunoglobulin samples irradiated to 45 kGy in the presence of 200 mM ascorbate had a 48% loss in activity compared to control. Liquid anti-insulin monoclonal immunoglobulin samples irradiated to 45 kGy in the presence of both 200 mM ascorbate and 200 mM Gly—Gly showed only a 29% loss in activity.

Example 51

In this experiment, the protective effect of ascorbate (200 mM) and a combination of ascorbate (200 mM) and Gly—Gly (200 mM) on two different frozen enzyme preparations (a glycosidase and a sulfatase) was evaluated.

Method

In glass vials, 300 μl total volume containing 300 μg of enzyme (1 mg/ml) were prepared with either no stabilizer or the stabilizer of interest. Samples were irradiated with gamma radiation (45 kGy total dose, dose rate and temperature of either 1.616 kGy/hr and −21.5° C. or 5.35 kGy/hr and −21.9° C.) and then assayed for structural integrity.

Structural integrity was determined by SDS-PAGE. Three 12.5% gels were prepared according to the following recipe: 4.2 ml acrylamide; 2.5 ml 4×-Tris (pH 8.8); 3.3 ml water; 100 μl 10% APS solution; and 10 μl TEMED, and placed in an electrophoresis unit with 1× Running Buffer (15.1 g Tris base; 72.0 g glycine; 5.0 g SDS in 1 l water, diluted 5-fold). Irradiated and control samples (1 mg/ml) were diluted with Sample Buffer (+/−beta-ME) in Eppindorf tubes and then centrifuged for several minutes. 20 μl of each diluted sample (~10 μg) were assayed.

Results

Liquid glycosidase samples irradiated to 45 kGy in the absence of a stabilizer showed significant loss of material and evidence of both aggregation and fragmentation. Much greater recovery of material was obtained from the irradiated samples containing ascorbate or a combination of ascorbate and Gly—Gly.

Liquid sulfatase samples irradiated to 45 kGy in the absence of a stabilizer showed significant loss of material and evidence of both aggregation and fragmentation. Much greater recovery of material was obtained from the irradiated samples containing ascorbate or a combination of ascorbate and Gly—Gly.

Example 52

In this experiment, the protective effect of ascorbate (200 mM) and a combination of ascorbate (200 mM) and Gly—Gly (200 mM) on a frozen glycosidase preparation was evaluated.

Method

Samples were prepared in 2 ml glass vials containing 52.6 μl of a glycosidase solution (5.7 mg/ml), no stabilizer or the stabilizer(s) of interest and sufficient water to make a total sample volume of 300 μl. Samples were irradiated at a dose rate of 1.616 or 5.35 kGy/hr at a temperature between −20 and −21.9° C. to a total dose of 45 kGy.

Structural integrity was determined by reverse phase chromatography. 10 μl of sample were diluted with 90 μl solvent A and then injected onto an Aquapore RP-300 (c-8) column (2.1×30 mm) mounted in an Applied Biosystems 130A Separation System Microbore HPLC. Solvent A: 0.1% trifluoroacetic acid; solvent B: 70% acetonitrile, 30% water, 0.085% trifluoroacetic acid.

Results

Liquid enzyme samples irradiated to 45 kGy in the absence of a stabilizer showed broadened and reduced peaks. Much greater recovery of material, as evidenced by significantly less reduction in peak size compared to control, was obtained from the irradiated samples containing ascorbate or a combination of ascorbate and Gly—Gly.

Example 53

In this experiment, the protective effect of various stabilizers on anti-insulin monoclonal immunoglobulin (50 mg/ml) supplemented with 0.1% human serum albumin (HSA) exposed to gamma irradiation up to 100 kGy was evaluated. The stabilizers tested were ascorbate (200 mM) and a mixture of ascorbate (200 mM) and Gly—Gly (200 mM).

Methods

Samples were irradiated at a dose rate of 0.458 kGy/hr to a total dose of 25, 50 or 100 kGy at ambient temperature (20–25° C.).

Monoclonal immunoglobulin activity was determined by a standard ELISA protocol. Maxisorp plates were coated with human recombinant insulin at 2.5 jig/ml overnight at 4° C. The plate was blocked with 380 μl of blocking buffer (PBS, pH 7.4, 2% BSA) for two hours at 37° C. and then washed three times with wash buffer (TBS, pH 7, 0.05% TWEEN 20). Serial 3-fold dilutions were performed. Plates were incubated for one hour at 37° C. with agitation and then washed six times with a wash buffer. Phosphatase-labelled goat anti-mouse IgG (H+L) was diluted to 50 ng/ml in binding buffer and 100 μl was added to each well. The plate was incubated for one hour at 37° C. with agitation and washed eight times with wash buffers. One hundred μl of Sigma-104 substrate (1 mg/ml in DEA buffer) was added to each well and reacted at room temperature. The plate was read on a Multiskan MCC/340 at 405 nm with the 620 nm absorbance subtracted.

Results

Samples of anti-insulin monoclonal immunoglobulin supplemented with 1% HSA lost all binding activity when gamma irradiated to 25 kGy. In contrast, samples containing a combination of ascorbate and Gly—Gly retained about 67% of binding activity when irradiated to 25 kGy, 50% when irradiated to 50 kGy and about 33% when irradiated to 100 kGy. Samples containing ascorbate alone retained about 65% of binding activity when irradiated to 25 kGy, about 33% when irradiated to 50 kGy and about 12% when irradiated to 100 kGy.

Example 54

In this experiment, the protective effect of the dipeptide stabilizer L-carnosine, alone or in combination with ascorbate (50 mM), on gamma irradiated liquid urokinase was evaluated.

Methods

Liquid urokinase samples (2000 IU/ml) were prepared using a buffer solution containing 100 mM Tris pH 8.8, 100 mM NaCl, and 0.2% PEG 8000. Samples were irradiated at a dose rate of 1.92 kGy/hr to a total dose of 45 kGy at 4° C. [300] Urokinase activity was determined using a colorimetric assay. The substrate was Urokinase Substrate I, Colorimetric, Calbiochem 672157 lot B23901. Substrate was reconstituted in a buffer solution containing 50 mM Tris pH 8.8, 50 mM NaCl and 0.1% PEG 8000 to a concentration of 1 mM). Irradiated samples were centrifuged (1–1.5×1000 RPM, Sorvall RT6000B Refrigerated Centrifuge with Sorvall rotor H1000B) for approximately 3 minutes and then 50 µl of substrate solution were added. The samples with added substrate were incubated at 37° C. with shaking and absorbance at 406–620 nm determined at 20 minute intervals beginning 5 minutes after addition of substrate to the sample.

Results

L-carnosine showed a concentration dependent protection of liquid urokinase (from about 15 mM to about 62.5 mM) irradiated to a total dose of 45 kGy. At concentrations greater than 62.5 mM, no additional protective effect was observed. When L-carnosine was combined with ascorbate (50 mM), a protective effect on irradiated liquid urokinase was also observed.

Example 55

In this experiment, the protective effect of the dipeptide stabilizer anserine on gamma irradiated liquid urokinase was evaluated.

Methods

Liquid urokinase samples (2000 IU/ml) were prepared using a buffer solution containing 100 mM Tris pH 8.8, 100 mM NaCl, and 0.2% PEG 8000. Samples were irradiated at a dose rate of 1.92 kGy/hr to a total dose of 45 kGy at 4° C.

Urokinase activity was determined using a colorimetric assay. The substrate was Urokinase Substrate I, Colorimetric, Calbiochem 672157 lot B23901. Substrate was reconstituted in a buffer solution containing 50 mM Tris pH 8.8, 50 mM NaCl and 0.1% PEG 8000 to a concentration of 1 mM). Irradiated samples were centrifuged (1–1.5×1000 RPM, Sorvall RT6000B Refrigerated Centrifuge with Sorvall rotor H1000B) for approximately 3 minutes and then 50 µl of substrate solution were added. The samples with added substrate were incubated at 37° C. with shaking and absorbance at 406–620 nm determined at 20 minute intervals beginning 5 minutes after addition of substrate to the sample.

Results

The addition of anserine provided approximately 10–15% protection to liquid urokinase irradiated to a total dose of 45 kGy. In contrast, liquid urokinase samples containing no anserine showed a complete loss of activity.

Example 56

In this experiment, the protective effect of L-carnosine on gamma irradiated liquid urokinase was evaluated.

Methods

Liquid urokinase samples (2000 IU/ml) were prepared using a buffer solution containing 100 mM Tris pH 8.8, 100 mM NaCl, and 0.2% PEG 8000. Samples were irradiated at a dose rate of 1.92 kGy/hr to a total dose of 45 kGy at 4° C. [308] Urokinase activity was determined using a colorimetric assay. The substrate was Urokinase Substrate I, Colorimetric, Calbiochem 672157 lot B23901. Substrate was reconstituted in a buffer solution containing 50 mM Tris pH 8.8, 50 mM NaCl and 0.1% PEG 8000 to a concentration of 1 mM). Irradiated samples were centrifuged (1–1.5×1000 RPM, Sorvall RT6000B Refrigerated Centrifuge with Sorvall rotor H1000B) for approximately 3 minutes and then 50 µl of substrate solution were added. The samples with added substrate were incubated at 37° C. with shaking and absorbance at 406–620 nm determined at 20 minute intervals beginning 5 minutes after addition of substrate to the sample.

Results

L-carnosine showed a concentration dependent protection of liquid urokinase irradiated to a total dose of 45 kGy. At concentrations of 125 and 250 mM, L-carnosine protected approximately 60–65% of the activity of irradiated liquid urokinase.

Example 57

In this experiment, the protective effect of L-carnosine on gamma irradiated immobilized anti-insulin monoclonal immunoglobulin was evaluated.

Methods

L-carnosine was prepared as a 100 mM solution in PBS pH 8–8.5. Approximately 100 µl of this solution was added to each sample being irradiated. Samples were irradiated at a dose rate of 1.92 kGy/hr to a total dose of 45 kGy at 4° C.

Monoclonal immunoglobulin activity was determined by a standard ELISA protocol. Maxisorp plates were coated with human recombinant insulin at 2 µg/ml overnight at 4° C. The plate was blocked with 200 µl of blocking buffer (PBS, pH 7.4, 2% BSA) for two hours at 37° C. and then washed six times with wash buffer (TBS, pH 7, 0.05% TWEEN 20). Samples were re-suspended in 500 µl of high purity water (100 ng/µl), diluted to 5 µg/ml in a 300 µl U-bottomed plate coated for either overnight or two hours with blocking buffer. Serial 3-fold dilutions were performed, with a final concentration of 0.0022 µg/ml. Plates were incubated for one hour at 37° C. with agitation and then washed six times with a wash buffer. Phosphatase-labelled goat anti-mouse IgG (H+L) was diluted to 50 ng/ml in binding buffer and 100 µl was added to each well. The plate was incubated for one hour at 37° C. with agitation and washed six times with wash buffers. One hundred µl of Sigma-104 substrate (1 mg/ml in DEA buffer) was added to each well and reacted at room temperature. The plate was read on a Multiskan MCC/340 at 405 nm with the 620 nm absorbance subtracted.

Results

Samples of immobilized anti-insulin monoclonal immunoglobulin lost all binding activity when gamma irradiated to 45 kGy. In contrast, samples containing L-carnosine retained about 50% of binding activity following gamma irradiation to 45 kGy.

Example 58

In this experiment, the protective effect of L-carnosine, alone or in combination with ascorbate, on gamma irradiated immobilized anti-insulin monoclonal immunoglobulin was evaluated.

Methods

L-carnosine was prepared as a solution in PBS pH 8–8.5 and added to each sample being irradiated across a range of concentration (25 mM, 50 mM, 100 mM or 200 mM). Ascorbate (either 50 mM or 200 mM) was added to some of the samples prior to irradiation. Samples were irradiated at a dose rate of 1.92 kGy/hr to a total dose of 45 kGy at 4° C.

Monoclonal immunoglobulin activity was determined by a standard ELISA protocol. Maxisorp plates were coated with human recombinant insulin at 2 µg/ml overnight at 4° C. The plate was blocked with 200 µl of blocking buffer (PBS, pH 7.4, 2% BSA) for two hours at 37° C. and then washed six times with wash buffer (TBS, pH 7, 0.05% TWEEN 20). Samples were re-suspended in 500 µl of high purity water (100 ng/µl), diluted to 5 µg/ml in a 300 µl U-bottomed plate coated for either overnight or two hours with blocking buffer. Serial 3-fold dilutions were performed, with a final concentration of 0.0022 µg/ml. Plates were incubated for one hour at 37° C. with agitation and then washed six times with a wash buffer. Phosphatase-labelled goat anti-mouse IgG (H+L) was diluted to 50 ng/ml in binding buffer and 100 µl was added to each well. The plate was incubated for one hour at 37° C. with agitation and washed six times with wash buffers. One hundred µl of Sigma-104 substrate (1 mg/ml in DEA buffer) was added to each well and reacted at room temperature. The plate was read on a Multiskan MCC/340 at 405 nm with the 620 nm absorbance subtracted.

Results

Samples of immobilized anti-insulin monoclonal immunoglobulin lost all binding activity when gamma irradiated to 45 kGy. In contrast, samples containing at least 50 mM L-carnosine retained about 50% of binding activity following gamma irradiation to 45 kGy. No additional protection was observed in the samples containing ascorbate as well, i.e. about 50% of binding activity was retained in samples containing at least 50 mM L-carnosine.

Example 59

In this experiment, the protective effect of L-carnosine, alone or in combination with ascorbate, on gamma irradiated lyophilized Factor VIII was evaluated.

Methods

Samples containing Factor VIII and the stabilizer(s) of interest were lyophilized and stoppered under vacuum. Samples were irradiated at a dose rate of 1.9 kGy/hr to a total dose of 45 kGy at 4° C. Following irradiation, samples were reconstituted with water containing BSA (125 mg/ml) and Factor VIII activity was determined by a one-stage clotting assay using an MLA Electra 1400C Automatic Coagulation Analyzer.

Results

L-carnosine substantially improved the retention of Factor VIII clotting activity following gamma irradiation.

Example 60

In this experiment, plasma protein fractions were irradiated (45 kGy at 1.9 kGy/hr at ambient temperature) at varying levels of residual solvent content and in the presence or absence of volatile stabilizers.

Method

In glass vials, samples of a commercially available plasma protein fraction (2 mg/ml) were prepared having either 9% water containing small amounts of ethanol and acetone or ~1% water containing substantially no ethanol or acetone. Samples were irradiated with gamma radiation (45 kGy total dose at 1.9 kGy/hr and ambient temperature) and then assayed for structural integrity. Structural integrity was determined by SDS-PAGE, HPLSEC and reverse phase HPLC.

For SDS-PAGE, three 12.5% gels were prepared according to the following recipe: 4.2 ml acrylamide; 2.5 ml 4×-Tris (pH 8.8); 3.3 ml water; 100 µl 10% APS solution; and 10 µl TEMED, and placed in an electrophoresis unit with 1× Running Buffer (15.1 g Tris base; 72.0 g glycine; 5.0 g SDS in 1l water, diluted 5-fold). Irradiated and control samples (I mg/ml) were diluted with Sample Buffer (+/- beta-ME) in Eppindorf tubes and then centrifuged for several minutes. 20 µl of each diluted sample (~10 µg) were assayed.

For reverse phase HPLC, each sample was dissolved in water to a final concentration of 10 mg/ml. These solutions were then serially diluted into 0.1% trifluoroacetic acid to the desired concentration. 10 µg of each sample was loaded onto an Aquapore RP-300 (C-8) 2.1×30 mm Microbore HPLC: Applied Biosystems 130A Separation System, flow rate 0.2 ml/min. Solvent A: 0.1% trifluoroacetic acid; solvent B: 70% acetonitrile, 30% water, 0.085% trifluoroacetic acid.

For HPLSEC, each sample was diluted to 0.4 µg/µl and 50 µl thereof loaded onto a Phenomenex-Biosep S3000 (molecular range 5kDa-700 kDa) for an analysis concentration of 20 µg: 20l µl of 2 mg/ml stock solution+80 µl elution buffer (50 mM $NaP_i$+100 mM NaCl pH 6.7); flow rate 1 ml/min Results Both samples exhibited some breakdown of albumin upon irradiation to 45 kGy, with the sample having 9% water containing small amounts of ethanol and acetone exhibiting less breakdown and greater structural recovery than the sample containing less water and substantially no volatile stabilizers. The structural recovery of both samples, however, was sufficient for subsequent use of the albumin.

More specifically, SDS-PAGE analysis demonstrates better recovery of albumin monomer from the sample having 9% water containing small amounts of ethanol and acetone. Similarly, HPLSEC also indicates less aggregation in the sample having 9% water containing small amounts of ethanol and acetone. Reverse phase HPLC showed no significant difference between irradiated samples and control.

Example 61

Human albumin (25%) was spiked 1:100 with 10% brain homogenate from hamster adapted scrapie (strain 263K). The sample was mixed by vortexing, and 46-ml aliquots of scrapie-spiked albumin were dispensed into 10-ml serum vials. One vial was stored at −80° C. as a frozen control. Three vials were taken to a commercial irradiation facility. One vial (the 0 kGy control) was refrigerated to prevent bacterial growth. The remaining vials were irradiated at ambient temperature (20–25° C.) at a rate of 0.4 kGy/hr to a total dose of 26 or 50 kGy. Radiation dose was assessed by dosimeters attached to each vial and by external dosimeters placed in close proximity to the vials. The irradiated samples and the 0 kGy control were assayed for scrapie infectivity.

Infectivity was assayed by intracerebral inoculation of 0.05 ml of sample into 12 hamsters, which were then held for up to 6 months for observation. Three clinical endpoints were assessed: wobble, failure-to-rear and death. There was an at least 8–10 day delay in the appearance of each clinical symptom in the group inoculated with the sample treated at the higher dose compared with the unirradiated control. The data were compared with a nomogram constructed from the dose response of the incubation time for a large number of animals infected in limiting dilution series mode (R. Rowher, unpublished data). This nomogram correlated days to onset of disease (as evidenced by wobble) with $log_{10}$ $LD_{50}$ inoculated.

The effect of the radiation on the biological material (albumin) was determined by SDS-PAGE gel electrophoresis and high performance size exclusion chromatography as follows.

SDS-PAGE was conducted in 8% polyacrylamide gels in a Mighty Small Mini-Vertical Unit SE250/SE260. Samples were diluted 1:100 in PBS and then 1:1 in Laemmli Sample Buffer (Bio-Rad) with or without 5% β-mercaptoethanol. Sample load was 12.5 µg per lane. The molecular weight markers were Low-Range Standard (Bio-Rad). Electrophoresis was conducted for 30 minutes at 125 volts. Gels were stained with 0.1% Coomassie Brilliant Blue R-250 in 50% methanol, 10% acetic acid and destained with 5% methanol, 9% acetic acid.

HPLSEC was performed on 7.8×300 mm Biosep SEC columns (Phenomenex, Torrence, Calif.) in 130A Separation System (Applied Biosystems). The eluant buffer of 0.05M sodium phosphate, 0.1 M sodium chloride (pH 6.7) was filtered before use with 0.22 µl filters. Albumin solutions were diluted to a final concentration of 1.25 mg/ml in eluant buffer and 25 µl (31.25 µg protein) was injected. Flow rate was 1 m/min. Detection was by absorbance at 280 nm.

Results

For the unirradiated control, the median incubation time for onset of disease (wobble) was 75 days. For the irradiated samples, the median incubation time for onset of disease was 88 days for the sample irradiated to a total dose of 25 kGy and 90 days for the sample irradiated to 50 kGy. Comparison with the nomogram gave estimated values for the logo titers as 6.5 for the unirradiated control and 4.8 and 4.6 for the samples irradiated to 25 kGy and 50 kGy, respectively. Based on these estimates, the median reduction factors for the irradiated samples were 1.7 and 1.9 for the samples irradiated to 25 kGy and 50 kGy, respectively These represent estimates of the median reduction values, but do not convey the maximum possible reduction predicted by this experiment. To do this, the minimum value of the 95% confidence interval (CI) of the control group should be compared with the maximum value of the 95%CI of the radiation treated groups. This calculation will yield the maximum reduction factor of the titres that lies within the 95%CI. For the 50 kGy group this value was 3.5 logs reduction.

The susceptibility of biological contaminants or pathogens to radiation is often expressed as their $D_{37}$ value. This represents the dose of radiation required to reduce the number of active biological contaminants or pathogens to 37% of their pre-irradiation number. Thus the lower the $D_{37}$, the more susceptible a particular biological contaminant or pathogen is to the effects of the radiation. The $D_{37}$ of the scrapie prion has been determined experimentally to be approximately 47 kGy (Rohwer, *Nature,* 308, 5960, pp. 658–662, 1984). Utilizing the methodology described herein, the $D_{37}$ of the scrapie prion was unexpectedly found to be only 4.5 kGy. Thus the $D_{37}$ of the prion was decreased using the methods and formulation employed in this experiment. Thus increased destruction of the scrapie prion was achieved while maintaining the integrity of the biological material, a commercial therapeutic 25% solution of human albumin, used in this experiment.

Increased destruction of the scrapie prion was achieved while maintaining the essential biological and physiological characteristics of the preparation containing albumin being treated. This particular biological material, a 25% solution of human albumin, was examined both pre- and post-irradiation with gamma radiation to total doses of 25, 50 and 100 kGy. As shown by gel electrophoresis, the albumin was largely intact at radiation doses up to 50 kGy, with only a small amount of fragmentation and aggregation and a slight decrease in the amount of the monomeric form of albumin. The results were similar for all of the albumin samples, irrespective of whether they contained any ascorbate and/or hamster. At higher doses, minor changes were seen in the albumin samples, mostly in the form of an increased polymerization of albumin.

A more detailed analysis was made using HPLSEC. With irradiation, the amount of albumin monomer decreased (peak at 10.5 min), the amount of dimer increased (9 min) and the amount of polymer increased (7.2 min). These changes were all minimized in the presence of ascorbate. The remaining peaks at 12.6 and 15.3 min are those of ascorbate and the N-acetyl tryptophan stabilizer, respectively.

Example 62

In the experiment, lyophilized albumin (containing 5% urokinase) was irradiated at a rate of 1.847 kGy/hr at approximately 4° C. to a total dose of 10 or 40 kGy.

Samples were analyzed by gel filtration using a TSKgel G4000$SW_{x1}$ 30 cm×7.8 mm column, separation range 20 kDa—7,000 kDa, elution buffer 0.1M sodium phosphate/ 0.1M sodium sulfate (pH 6.5), flow rate 1 ml/min.

There was no change in the albumin when lyophilized and irradiated to either 10 kGy or 40 kGy total dose. In contrast, liquid albumin samples exhibited significant degradation when irradiated to 40 kGy total dose.

Example 63

In this experiment, samples of albumin solution (25%) were prepared and half of the samples sparged with Argon.

Samples were irradiated at a rate of 0.91, 0.92 or 1.01 kGy/hr to a total dose of 18.1, 23 and 30.4 kGy, respectively. Irradiated samples were assayed by SDS-PAGE for aggregation. SDS-PAGE showed only small amount of fragmentation (doublet below 66 kDa band on reduced gel) and aggregation (116 kDa band on non-reduced gel), even for samples irradiated to a total dose of 30.4 kGy.

HPLSEC showed the following peaks:

| Total dose (kGy) | polymer (w/Ar) | dimer (w/Ar) | polymer (no Ar) | dimer (no Ar) |
|---|---|---|---|---|
| 0 (control) | 4.0% | 1.8% | 4.4% | 2.7% |
| 18.1 | 5.1% | 5.6% | 5.1% | 6.6% |
| 23 | 6.2% | 7.0% | 6.0% | 8.7% |
| 30.4 | 7.2% | 8.3% | 7.3% | 9.8% |

As shown by HPLSEC, less dimerization was seen in samples that had been sparged with Argon prior to irradiation Example 64

In this experiment, plasma protein fractions were irradiated at −20° C. to varying total doses of radiation (10, 30 or 50 kGy).

Method

In glass vials, samples of a commercially available plasma protein fraction were prepared at a reduced solvent level of 9% water containing small amounts of ethanol and acetone. Samples were irradiated with gamma radiation at −20° C. at 1.608 kGy/hr. to a total dose of 10, 30 or 50 kGy and then assayed for structural integrity. Structural integrity was determined by SDS-PAGE and HPLSEC.

For SDS-PAGE, four 12.5% gels were prepared according to the following recipe: 4.2 ml acrylamide; 2.5 ml 4×-Tris (pH 8.8); 3.3 ml water; 100 μl 10% APS solution; and 10 μl TEMED, and placed in an electrophoresis unit with 1× Running Buffer (15.1 g Tris base; 72.0 g glycine; 5.0 g SDS in 1 l water, diluted 5-fold). Irradiated and control samples (1 mg/ml) were diluted with Sample Buffer (+/−beta-ME) in Eppindorf tubes and then centrifuged for several minutes. 20 l μl of each diluted sample (~10 μg) were assayed.

For HPLSEC, 31 μg of each sample was loaded onto a Biosep SEC S3000 7.7×300 mm column in an Applied Biosystems 130A Separation System, flow rate 1 ml/min in 50 mM $Na_2HPO_4$ (pH 6.7), 100 mM NaCl.

Results

SDS-PAGE analysis demonstrates quantitative recovery of albumin monomer from the irradiated samples, even up to a total dose of 50 kGy of radiation. Similarly, HPLSEC indicates no increase in aggregation in any of the irradiated samples, even up to a total dose of 50 kGy of radiation.

Example 65

In this experiment, baby hamster kidney (BHK) cells obtained from the American Type Culture Collection were grown on media containing 20% (volume/volume) fetal bovine serum (FBS) and were slowly acclimated so that they were eventually able to grow with only 0.25% FBS (which is 5% of their normal FBS requirement). As then FBS was reduced, the media was supplemented with a commercial plasma protein fraction, either unirradiated or irradiated at a temperature of −20° C. at 1.608 kGy/hr. to a total dose of 50 kGy radiation, so that the plasma protein fraction was 0.3% weight/volume of the media (600 mg).

Results

There was no observable difference between BHK cells grown on media containing unirradiated plasma protein fraction and BHK cells grown on media containing plasma protein fraction that had been irradiated to a total dose of 50 kGy.

Example 66

In this experiment, plasma protein fractions containing porcine parvovirus (PPV) were irradiated at −80° C. to varying total doses of radiation.

Method

PPV stock #7 was prepared using 20%PEG8000 in 2.5M NaCl. The PEG-precipitated virus pellet was resuspended in PEG buffer (0.1M NaCl, 0.01 M Tris (pH 7.4), 1 mM EDTA).

Method 1

50 μl of PK-13 media or PPV stock #7 was added to 2 ml Wheaton vials and allowed to dry overnight at 40° C. 50 mg of a commercial plasma protein fraction was added once the liquid was dry and the vials were stoppered and then irradiated at −80° C. at a rate of 5.202 kGy/hr. to a total dose of 10, 30 or 45 kGy.

Method 2

50 mg of a commercial plasma protein fraction was placed in a 2 ml Wheaton vial and then mixed with either 150 μl of PK-13 media or 150 μl of diluted PPV stock #7 (100 μl PK-13 media+50 μl PPV) until dissolved. The vials were stoppered and then irradiated at −80° C. at a rate of 5.202 kGy/hr to a total dose of 10, 30 or 45 kGy.

$TCID_{50}$ Assay

850 μl of PK-13 media (DMEM ATCC#3020002, 10% FBS Gibco#26140079, 1% Pen/Step/L-Glutamine Gibco#10378016) was added to each vial to bring the volume to 1 ml. Samples were then filter sterilized using 13 mm filters (Becton Dickenson #4454) and 3 ml syringes.

PK-13 cells (ATCC#CRL-6489) were maintained in PK-13 growth media and seeded at 40% confluency the day prior to infection in 96-well plates. When cells were 70–80% confluent, 50 μl of the desired irradiated sample (containing either PK-13 media or diluted PPV stock #7) was added to 4 wells.

SDS-PAGE

Following irradiation, stock solutions of samples were prepared in HPLC water (10 mg/ml) and then diluted (2 mg/ml). Samples were then diluted 1:1 with 2× sample buffer (with or without DTT) and then loaded onto gels: 5 μg (10 μl) for samples from Method 1 and 10 μg (10 μl) for samples from Method 2.

Results

PPV treated plasma protein fractions irradiated at −80° C. according to Method 1 exhibited a viral kill of 3.9 logs using a total dose of 45 kGy (0.084 log/kGy). PPV treated plasma protein fractions irradiated at −80° C. according to Method 2 exhibited a viral kill of 5.54 logs (0.123 log/kGy). The irradiated plasma protein fractions did not cause any cytopathic effects in PK-13 cells.

PPV treated plasma protein fractions irradiated at −80° C. were also assayed using SDS-PAGE.

Example 67

In this experiment, frozen preparations containing albumin and Factor VIII were irradiated.

Method

Samples containing albumin and Factor VIII were frozen and gamma irradiated to a total dose of 45 kGy.

Results

There was no difference between the FVIII activity of the control (unirradiated) sample and the FVIII activity of the sample frozen and gamma irradiated to 45 kGy.

Example 68

In this experiment, lyophilized trypsin was irradiated (45 kGy at 1.9 kGy/hr) alone or in the presence of a stabilizer (sodium ascorbate 100 mM) at varying levels of residual solvent content.

Method 1 ml aliquots of trypsin alone or with 100 mM sodium ascorbate (10 mg/ml) were placed in 3 ml vials. Samples were prepared in triplicate and subjected to lyophilization, either a primary drying cycle (22 hours, sample temp 0–10° C., shelf temp 35° C., 10 mT) or a combination of a primary drying cycle and a secondary drying cycle (60 hours, sample temp 40° C., shelf temp 40° C., 10 mT).

All samples were resuspended in 1 ml water, and then diluted 1:10 for assay. Assay conditions: 50 units/ml trypsin per well+BAPNA substrate starting at 3000 μg/ml was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

In the absence of stabilizer, lyophilized trypsin exposed to 45 kGy total dose gamma-irradiation showed recovery of 74% of control activity at the higher residual solvent content level, i.e. about 2.4% water, and recovery of 85% of control activity at the lower residual solvent content level, i.e., about 1.8% water.

In the presence of stabilizer, trypsin exposed to 45 kGy total dose gamma-irradiation showed recovery of 97% of control activity at higher residual solvent content levels, i.e. about 3.7% water, and recovery of 86% of control activity at lower residual solvent content levels, i.e. about 0.7% water.

Example 69

In this experiment, trypsin was irradiated (45 kGy at 1.6 kGy/hr. and 4° C.) in the presence of a stabilizer (sodium ascorbate 200 mM) as either a liquid or lyophilized preparation at varying pH levels.

Method 1 ml of 1 mg/ml (about 3000 IU/ml) trypsin aliquots in the presence of 35 mM phosphate buffer and 200 mM sodium ascorbate were made at varying pH levels between 5 and 8.5, inclusive. 400 µl of each solution was placed in 3 ml vials and then lyophilized and gamma-irradiated. The remaining portion of each solution was gamma-irradiated as a liquid. Lyophilized and liquid samples were assayed at the same time, under the following conditions: Assay conditions: 5 U/well trypsin (50 U/ml)+BATNA substrate (1 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

Liquid trypsin samples exposed to 45 kGy total dose gamma-irradiation showed recovery of between about 70 and 75% of control activity across the pH range tested. Lyophilized trypsin samples showed recovery of between about 86 and 97% of control activity across the same pH ranges. More specifically, the following results were observed:

| Sample # | pH | lyophilized (% of control activity) | liquid (% of control activity) |
|---|---|---|---|
| 1 | 5 | 91.11 | 69.87 |
| 2 | 5.5 | 94.38 | 74.86 |
| 3 | 6 | 85.54 | 75.77 |
| 4 | 6.47 | 96.26 | 71.79 |
| 5 | 7 | 90.40 | 75.59 |
| 6 | 7.5 | 96.79 | 75.63 |
| 7 | 7.8 | 90.62 | 74.55 |
| 8 | 8.5 | 89.59 | 71.08 |

Example 70

In this experiment, lyophilized trypsin was irradiated (42.7–44.8 kGy at 2.65 kGy/hr at 4° C.) alone or in the presence of a stabilizer (sodium ascorbate 200 mM).

Method 1 ml aliquots of trypsin alone or with 200 mM sodium ascorbate (1 mg/ml) were placed in 3 ml vials and frozen overnight at −70° C. Samples were prepared in quadruplicate and subjected to lyophilization, utilizing primary and secondary drying cycles (20 hours total).

All samples were resuspended in 1 ml water, and then diluted 1:10 for assay. Assay conditions: 50 units/ml trypsin per well+BATNA substrate starting at 3000 µg/ml was serially diluted 3-fold down a 96-well plate. The assay was set up in two 96-well plates and absorption read at both 405 and 620 µm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

In the absence of stabilizer, lyophilized trypsin exposed to gamma-irradiation showed recovery of 63% of control activity. In the presence of stabilizer, lyophilized trypsin exposed to gamma-irradiation showed recovery of 88% of control activity.

Example 71

In this experiment, trypsin that had been lyophilized (0.7% moisture) was irradiated (45 kGy at 1.867 kGy/hr at 3.2° C.) alone or in the presence of a stabilizer (sodium ascorbate 100 mM) at varying levels of residual solvent content.

Method 1 ml aliquots of trypsin alone or with 100 mM sodium ascorbate (10 mg/ml) were placed in 3 ml vials and frozen overnight at −70° C. Samples were prepared in quadruplicate and subjected to lyophilization (69.5 hours total run time; shelf temperature 35° C.).

All samples were resuspended in 1 ml water, and then diluted 1:10 for assay. Assay conditions: 50 units/ml trypsin per well+BAPNA substrate starting at 3000 µg/ml was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

In the absence of stabilizer, trypsin (3.9% water) exposed to 45 kGy total dose gamma-irradiation showed recovery of 77% of control activity. In the presence of stabilizer, trypsin (0.7% water) exposed to 45 kGy total dose gamma-irradiation showed recovery of 86% of control activity.

Example 72

In this experiment, lyophilized trypsin was irradiated (45 kGy at 1.9 kGy/hr) alone or in the presence of a stabilizer (sodium ascorbate 100 mM) at varying levels of residual solvent content.

Method 1 ml aliquots of trypsin alone or with 100 mM sodium ascorbate (10 mg/ml) were placed in 3 ml vials. Samples were prepared in triplicate and subjected to lyophilization, either a primary drying cycle (25 hours, sample temp 0–10° C., shelf temp 35° C., 10 mT) or a combination of a primary drying cycle and a secondary drying cycle (65 hours, sample temp 40° C., shelf temp 40° C., 10 mT).

All samples were resuspended in 1 ml water, and then diluted 1:10 for assay. Assay conditions: 50 units/ml trypsin per well+BAPNA substrate starting at 3000 µg/ml was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

In the absence of stabilizer, trypsin exposed to 45 kGy total dose gamma-irradiation showed recovery of 74% of control activity at the higher residual solvent content level, i.e. about 5.8% water, and recovery of 77% of control activity at the lower residual solvent content level, i.e., about 5.4% water.

In the presence of stabilizer, trypsin exposed to 45 kGy total dose gamma-irradiation showed recovery of 97% of control activity at higher residual solvent content levels, i.e. about 2.8% water, and recovery of 90% of control activity at lower residual solvent content levels, i.e. about 1.1%

Example 73

In this experiment, trypsin suspended in polypropylene glycol 400 was subjected to gamma irradiation at varying levels of residual solvent (water) content.

Method

Trypsin was suspended in polypropylene glycol 400 at a concentration of about 20,000 U/ml and divided into multiple samples. A fixed amount of water (0%, 1%, 2.4%, 4.8%, 7%, 9%, 10%, 20%, 33%) was added to each sample; a 100% water sample was also prepared which contained no PPG 400.

Samples were irradiated to a total dose of 45 kGy at a rate of 1.9 kGy/hr and a temperature of 4° C. Following irradiation, each sample was centrifuged to pellet the undissolved trypsin. The PPG/water soluble fraction was removed and the pellets resuspended in water alone.

Assay conditions: 5 U/well trypsin (50 U/ml)+BAPNA substrate (0.5 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

The irradiated samples containing a mixture of polypropylene glycol (PPG 400) and water (up to 33% water) retained about 80% of the activity of an unirradiated trypsin control and activity equal to that of a dry (lyophilized) trypsin control irradiated under identical conditions. No activity was detected in the 100% water sample irradiated to 45 kGy.

Example 74

In this experiment, an aqueous solution of trypsin was subjected to gamma irradiation at varying concentrations of a stabilizer (sodium ascorbate, alone or in combination with 1.5 mM uric acid).

Method

Trypsin samples (5 Units/sample) were prepared with varying concentrations of sodium ascorbate, alone or in combination with 1.5 mM uric acid. Samples were irradiated to a total dose of 45 kGy at a rate of 1.9 kGy/hr and a temperature of 4° C.

Assay conditions: 5 U/well trypsin (50 U/ml)+50 μl BAPNA substrate (1 mg/ml). The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

The irradiated samples containing at least 20 mM ascorbate retained varying levels of trypsin activity compared to an unirradiated control. Samples containing 125 mM or more ascorbate retained about 75% of the trypsin activity of an unirradiated control. Similar results were observed with samples containing ascorbate in combination with uric acid.

Example 75

In this experiment, the protective effect of ascorbate (200 mM) and a combination of ascorbate (200 mM) and Gly—Gly (200 mM) on two different frozen enzyme preparations (a glycosidase and a sulfatase) was evaluated.

Method

In glass vials, 300 μl total volume containing 300 μg of enzyme (1 mg/ml) were prepared with either no stabilizer or the stabilizer of interest. Samples were irradiated with gamma radiation (45 kGy total dose, dose rate and temperature of 1.616 kGy/hr and −21.5° C. or 5.35 kGy/hr and −21.9° C.) and then assayed for structural integrity.

Structural integrity was determined by SDS-PAGE. Three 12.5% gels were prepared according to the following recipe: 4.2 ml acrylamide; 2.5 ml 4×-Tris (pH 8.8); 3.3 ml water; 100 μl 10% APS solution; and 10 μl TEMED. This solution was then placed in an electrophoresis unit with 1× Running Buffer (15.1 g Tris base; 72.0 g glycine; 5.0 g SDS in 1 μl water, diluted 5-fold). Irradiated and control samples (1 mg/ml) were diluted with Sample Buffer (+/−beta-ME) in Eppindorf tubes and then centrifuged for several minutes. 20 μl of each diluted sample (~10 μg) were assayed.

Results

Liquid enzyme samples irradiated to 45 kGy in the absence of a stabilizer showed significant loss of material and evidence of both aggregation and fragmentation. Much greater recovery of material was obtained from the irradiated samples containing ascorbate or a combination of ascorbate and Gly—Gly.

Example 76

In this experiment, the protective effect of ascorbate (200 mM) and a combination of ascorbate (200 mM) and Gly—Gly (200 mM) on a frozen glycosidase preparation was evaluated.

Method

Samples were prepared in 2 ml glass vials, each containing 52.6 μl of a glycosidase solution (5.7 mg/ml), and either no stabilizer or a stabilizer of interest, and sufficient water to make a total sample volume of 300 μl. Samples were irradiated with gamma radiation (45 kGy total dose, dose rate and temperature of either 1.616 kGy/hr and −21.5° C. or 5.35 kGy/hr and −21.9° C.) and then assayed for structural integrity.

Structural integrity was determined by reverse phase chromatography. 10 μl of sample were diluted with 90 μl solvent A and then injected onto an Aquapore RP-300 (c-8) column (2.1×30 mm) mounted in an Applied Biosystems 130A Separation System Microbore HPLC. Solvent A: 0.1% trifluoroacetic acid; solvent B: 70% acetonitrile, 30% water, 0.085% trifluoroacetic acid.

Results

Enzyme samples irradiated to 45 kGy in the absence of a stabilizer showed broadened and reduced peaks. Much greater recovery of material, as evidenced by significantly less reduction in peak size compared to control, was obtained from the irradiated samples containing ascorbate or a combination of ascorbate and Gly—Gly.

Example 77

In this experiment, lyophilized trypsin was irradiated (45 kGy total dose at 1.9 kGy/hr. at 4° C.) in the presence of Tris buffer (pH 7.6) or phosphate buffer (pH 7.5).

Method

Aliquots of a 1000 IU/ml trypsin solution were placed in 3 ml vials and then lyophilized and gamma-irradiated. The remaining portion of each solution was gamma-irradiated as a liquid. Samples were assayed under the following conditions: Assay conditions: 5 U/well trypsin (50 U/ml)+BATNA substrate (1 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

Lyophilized trypsin samples exposed to 45 kGy total dose gamma-irradiation showed recovery of essentially all trypsin activity in the presence of Tris buffer and sodium ascorbate and recovery of 88% of trypsin activity in the presence of phosphate buffer and sodium ascorbate.

Example 78

In this experiment, lyophilized enzyme preparations (a glycosidase and a sulfatase) were irradiated in the absence or presence of a stabilizer (100 mM sodium ascorbate).

Method

Glass vials containing 1 mg of enzyme were prepared with either no stabilizer or 100 mM sodium ascorbate (50 $\mu$l of 2M solution) and sufficient water to make 1 ml of sample. Samples were lyophilized following moisture levels: glycosidase with stabilizer, 3.4%; glycosidase without stabilizer, 3.2%; sulfate with stabilizer, 1.8%; and sulfate without stabilizer, 0.7%. Lyophilized samples were irradiated with gamma radiation (45 kGy total dose at 1.8 kGy/hr and 4° C.) and then assayed for structural integrity.

Structural integrity was determined by SDS-PAGE. In an electrophoresis unit, 6 $\mu$g/lane of each sample was run at 120V on a 7.5%–15% acrylamide gradient gel with a 4.5% acrylamide stacker under non-reducing conditions.

Results

Lyophilized glycosidase samples irradiated to 45 kGy in the absence of a stabilizer showed significant recovery of intact enzyme with only some fragmentation. Fragmentation was reduced by the addition of a stabilizer.

Similarly, lyophilized sulfatase samples irradiated to 45 kGy in the absence of a stabilizer showed good recovery of intact enzyme, but with slightly more fragmentation. Fragmentation was again reduced by the addition of a stabilizer.

Example 79

In this experiment, lyophilized glycosidase preparations irradiated in the absence or presence of a stabilizer (200 mM sodium ascorbate or a combination of 200 mM ascorbate and 200 mM glycylglycine).

Methods

Samples were prepared in glass vials, each containing 300 $\mu$g of a lyophilized glycosidase and either no stabilizer or a stabilizer of interest. Samples were irradiated with gamma radiation to varying total doses (10 kGy, 30 kGy and 50 kGy total dose, at a rate of 0.6 kGy/hr. and a temperature of −60° C.) and then assayed for structural integrity using SDS-PAGE.

Samples were reconstituted with water to a concentration of 1 mg/ml, diluted 1:1 with 2× sample buffer (15.0 ml 4× Upper Tris-SDS buffer (pH 6.8); 1.2 g sodium dodecyl sulfate; 6 ml glycerol; sufficient water to make up 30 ml; either with or without 0.46 g dithiothreitol), and then heated at 80° C. for 10 minutes. 10 $\mu$l of each sample (containing 5 $\mu$g of enzyme) were loaded into each lane of a 10% polyacrylamide gel and run on an electrophoresis unit at 125V for about 1.5 hours.

Results

About 80% of the enzyme was recovered following irradiation of the samples containing no stabilizer, with some degradation. Less degradation was observed in the samples containing ascorbate alone as the stabilizer, and even less degradation in the samples containing a combination of ascorbate and glycylglycine as the stabilizer.

Example 80—Sterilization of Blood

A 200 ml bag of one day old packed red blood cells was used. Ethanol was added to the cells in order to achieve a final ethanol concentration of 0.01% v/v. The red blood cells were diluted by a factor of one in ten using a modified Citrate Phosphate Dextrose (CPD) solution having a pH of about 6.4 to 6.7 and having the following composition in a total volume of 500 ml:

| | |
|---|---|
| Citrate Acid Monohydrate | 0.2 g |
| Sodium Citrate Dihydrate | 27.3 g |
| Sodium Monobasic Phosphate | 2.2 g |
| Sodium Dibasic Phosphate | 1.0 g |
| Dextrose | 3.2 g |

The cells were irradiated in a commercial size gamma irradiator which contained a cobalt 60 source rack. Irradiation was done off carrier in an unprotected box. The cells were irradiated for twenty-four hours at a rate of approximately 1 kGy/hr. After the irradiation period the red blood cells were examined visually and were found to be viable, having a brilliant red color. A control sample, consisting of packed red blood cells that were not diluted with the above-described CPD solution, was not viable after irradiation.

Four days after the irradiation procedure, the diluted cells were tested for levels of various blood components and the results are shown in Table 1. The control sample consisted of blood from the same bag as the test sample but it did not undergo irradiation. Table I illustrates that dilution and irradiation of human blood cells did not significantly alter the white blood cell count. The platelet count and hematocrit values were slightly lower than the control; however, these values are still within the range that is seen in normal adult blood. The level of hemoglobin was higher than in the control indicating that some red blood cells did lyse during the procedure. This is also evidenced by the lower red blood cell count. Nevertheless, contrary to what has been previously published, up to 50 kGy of radiation did not destroy the components of blood by the present procedure. The cells were also counted and found to be viable after 25 kGy of gamma irradiation delivered at a low dose rate of 1 kGy/hr.

TABLE 1

| Component | Irradiated Blood | Control Blood |
| --- | --- | --- |
| White Blood Cells | 4 K/mm$^3$ | 4.8 K/mm$^3$ |
| Red Blood Cells | 3 Mi/mm$^3$ | 7.2 Mi/mm$^3$ |
| Hemoglobin | 42 g/dl | 21 g/dl |
| Hematocrit | 46% | 64% |
| Platelet | 100 k/mm$^3$ | 120 k/mm$^3$ |

TABLE 2

| Parameter | Control (%) | Irradiated (%) |
| --- | --- | --- |
| Polymer | 2 | 3 |
| Dimer | 7 | 8 |
| Monomer | 90 | 86 |
| Low Molecular Weight | 1 | 3 |
| pH | 7.05 | 6.97 |
| NTU(must be >20) | 11.4 | 11.4 |

Example 81—Sterilization of Dextrose

Dextrose (or glucose) containing solutions are used in the treatment of carbohydrate and fluid depletion, in the treatment of hypoglycemia, as a plasma expander, in renal dialysis and to counteract hepatotoxins (The Merck Index, Eleventh Edition, Merck & Co., Inc. (1989), and Martindale's Extra Pharmacopecia, p.1, 265) Dextrose is also the preferred source of carbohydrate in parental nutrition regiments (The Merck Index, Eleventh Edition, Merck & Co., Inc. (1989), and Martindale's Extra Pharmacopecia, p.1, 265) In all of the above applications, the dextrose must be sterilized before use. Sterilization of dextrose-containing products is generally done by heat sterilization or autoclaving. Unfortunately, these methods have been reported to degrade or carmelize dextrose-containing solutions resulting in a color change in the solution (Martindale's Extra Pharmacopecia p.1, 265) Gamma irradiation of glucose has also been reported to decompose glucose-containing solutions (Kawakishi, et al., "Radiation Induced Degradation of D-glucose in Anaerobic Condition," *Agric. Biol. Chem.*, June 1977) Therefore, there is a need for a method that can sterilize dextrose-containing products that does not degrade the product itself. In view of the problems of the prior art, a dextrose solution was treated according to the method of the present invention as follows.

A 5% dextrose solution was irradiated for 24 hours, at a rate of approximately 1 kGy/hr. After irradiation, the product was tested and it was found that there was no visible light spectrum change as compared to the non-irradiated control. Therefore, the present method can be useful in sterilizing products that contain dextrose.

In addition to the above experiment, fresh solutions of 5% and 50% dextrose were irradiated to 25 kGy over 36 hours at ambient temperature. The results were similar to those described above. In addition, UV/VIS scans were obtained and demonstrated a complete absence of the peak at 283.4 nm for "furfural" as per U.S.P. In contrast, dextrose samples sterilized using an autoclave contain the 283.4 furfural peak. "Furfurals" are carcinogenic.

Example 82—Sterilization of Human Serum Albumin

Normal Human Serum Albumin was irradiated as a 25% salt-poor solution to a total dose of 25 kGy over 36 hours using a Gammacell 220 (Co$^{60}$ is the gamma ray source in this instrument) The temperature was not controlled during the irradiation but it is estimated that the container holding the albumin solution was approximately 23° C. The results of HPLC analysis are given in Table 2.

As the results demonstrate, Normal Human Serum Albumin can safely be irradiated to 25 kGy (at a rate of approximately 0.7 kGy/hr) at room temperature without adversely affecting the essential properties of the protein. This has not been demonstrated before. All other attempts at irradiating serum albumin require that it be irradiated in the frozen stage. This adds to the cost and difficulty of doing the irradiation.

Example 83

Normal human blood from a healthy donor was taken in a heparinized tube, washed three times with standard CPD solution, then diluted 1:20 with CPD containing 0.01% v/v ethanol. This latter solution of CPD with 0.01% v/v ethanol is called SCPD. Two ml aliquots were then placed in 10 ml plastic test tubes and irradiated to different doses up to 26 kGy over 36 hours at room temperature. There was no haemolysis and the cells appeared intact if somewhat large and slightly irregular in shape. The cells were easily put into suspension and reconstituted in fresh buffer.

The following three experiments (Examples 84, 85 and 86) were conducted in order to determine the efficacy of the method when treating HIV-contaminated blood: In each Example the cells were similarly treated. In these experiments, the cells were gently agitated after 12, 16 and 24 hours of irradiation. Further, in the third experiment (Example 86), the cells were placed in T25 flasks to provide greater surface area and reduce the concentration due to settling in the bottom of the centrifuge tubes. In each case, the cells were irradiated at a dose rate of approximately 0.7 kGy/hr.

Example 84—Sterilization of HIV-containing Blood

The following experiments were undertaken with the following specific objectives:

1. To evaluate the toxicity of the process towards red blood cells (RBCs); and
2. To evaluate the anti-retroviral activity of the process.

Procedure

Initially, 2 ml of anticoagulated blood was obtained from an HIV-seronegative donor. The blood was centrifuged, and the plasma was removed. The remaining cell pellet was resuspended in 10 ml of the GPO buffer and centrifuged. This washing process was repeated a total of three times. The final pellet was resuspended in 40 ml of the SCPD buffer, and distributed into plastic tubes in 2 ml aliquots, with 16 separate aliquots being retained for further manipulation. For 8 of these tubes, an aliquote of HTLV-IIIB was added. This is a laboratory strain of the HIV virus and 100 tissue culture infective doses (TCID) were added to each of the tubes to be infected. For the remaining 8 tubes, a "mock" infection was performed, by adding a small amount of non-infectious laboratory buffer, phosphate buffered saline (PBS) Four infected and four non-infected tubes were subjected to the process. For comparison, the remaining 8 tubes (four infected and four non-infected) were handled in an identical manner, except that they were not subjected to the process.

It should be stated that at the beginning of the study, a separate aliquot of blood was obtained from the donor. This was processed in the clinical hematology laboratory and a complete hemogram was performed. These baseline results were compared to repeat testing on the study aliquots, which included evaluation of four processed and four unprocessed samples, all of which were not infected with HIV.

An aliquot of 0.5 ml of each of the infected study samples was inoculated on mononuclear cells (MCs) which had been obtained three days earlier. These cells had been suspended in RMPI culture medium, with 10% fetal calf serum and other additives (penicillin, streptomycin, glutamine and HEPES buffer) along with 1 $\mu$g/ml PHA-P. At the same time as this inocculation, the cells were resuspended in fresh medium with rIL-2 (20 U/ml) The cultures were maintained for 7 days. Twice weekly, a portion of the culture medium was harvested for the measurement of HIV p24 antigen levels (commercial ELISA kit, Coulter Electronics, Hialeah, Fla.) for the measurement of viral growth.

A separate aliquot of the eight infected study samples was used for viral titration experiments. Briefly, serial four-fold dilutions of the virus-containing fluids (ranging from 1:16 to 1:65,536) were inoculated in triplicate in 96-well, flat-bottom tissue culture plates. PHA-stimulated MCs were added to each well (4 million cells in 2 ml culture medium, with 111–2) An aliquot of the supernatant from each culture well was harvested twice weekly for the measurement of HIV p24 antigen levels. A well was scored as "positive" if the HIV p24 antigen value was >30 $\mu$g/ml.

The viral titer was calculated according to the Spearman-Karber method (se ACTG virology protocol manual) using the following equation:

$$M = xk + d[0.5 - (1/n)r]$$

M: titer (in log 4)
xk: dose of highest dilution
d: space between dilutions
n: number of wells per dilution
r: sum of total number of wells Results Red blood cell parameters for the baseline sample as well as for the unprocessed and processed study samples are shown in Table 3.

TABLE 3

| Sample/Number | MCV | MCH | MCHC |
|---|---|---|---|
| Baseline | 94.5 | 32.0 | 339 |
| Unprocessed-1 | 91.4 | 34.4 | 376 |
| Unprocessed-2 | 90.2 | 37.9 | 420 |
| Unprocessed-3 | 92.1 | 40.0 | 433 |
| Unprocessed-4 | 91.0 | 40.2 | 442 |
| Processed-1 | 133.4 | 37.8 | 284 |
| Processed-2 | 131.5 | 45.0 | 342 |
| Processed-3 | 128.5 | 38.9 | 303 |
| Processed-4 | 131.1 | 39.4 | 301 |

MCV: Mean Corpuscular Volume (femtoliters)
MCH: Mean Corpuscular Hemoglobin (picograms)
MCHC: Mean Corpuscular Hemoglobin Concentration (grams/liter)

As described above, HIV cultures were established using 0.5 ml aliquots of unprocessed and processed study samples. P24 antigen levels (pg/ml) from the study samples on day 4 and day 7 of culture are shown in Table 4.

TABLE 4

| Sample/Number | Day 4 | Day 7 |
|---|---|---|
| Unprocessed-1 | 1360 | 484 |
| Unprocessed-2 | 1180 | 418 |
| Unprocessed-3 | 1230 | 516 |
| Unprocessed-4 | 1080 | 563 |
| Processed-1 | 579 | 241 |
| Processed-2 | 760 | 303 |
| Processed-3 | 590 | 276 |
| Processed-4 | 622 | 203 |

Finally, one unprocessed sample and one processed sample were selected for the performance of direct viral titration without culture. The results are shown in Table 5.

TABLE 5

| Sample/Number | Titer (log 10 ml) |
|---|---|
| Unprocessed-1 | 1.5 |
| Processed-1 | 0.0 |

The red blood cells were minimally affected by the process, although some reproducible macrocytosis was observed. Although on co-culturing of processed samples, there appeared to be some residual live virus, this was not confirmed by direct titration experiments.

Example 85

The objective of this experiment was to evaluate the toxicity of the process towards red blood cells in a comprehensive manner.

Methods

For this experiment, 1 ml of anticoagulated blood was obtained from the same HIV-seronegative donor as in example 84. The blood was centrifuged and the plasma was removed. The remaining cell pellet was resuspended in 10 ml of the GPO buffer and centrifuged. This washing process was repeated a total of three times. The final pellet was resuspended in 20 ml of the SCPD buffer and distributed into plastic tubes in 2 ml aliquots with all 10 aliquots being retained for further manipulation. Eight tubes were subjected to the process, while the final two tubes were retained as control, unprocessed tubes. After the processing, all the tubes were centrifuged, and the resulting pellet was resuspended in 100 $\mu$l buffer. A complete hemogram was performed on these reconcentrated study samples.

As in the example 84, a separate aliquot of blood was obtained from the donor when the study sample was taken. A complete hemogram was performed on this baseline sample. As the study samples were re-concentrated to 33–50% of their original state, more direct comparisons with the baseline sample could be.

Results

Red blood cell parameters for the baseline sample as well as for the unprocessed and processed study samples are shown in Table 6.

TABLE 6

| Sample/Number | RCB | HGB | MCV | MCH | MCHC |
|---|---|---|---|---|---|
| Baseline | 4.76 | 152 | 94.9 | 31.9 | 336 |
| Unprocessed 1 | 0.99 | 33 | 90.2 | 33.0 | 366 |
| Unprocessed 2 | 1.08 | 41 | 89.5 | 38.3 | 427 |

TABLE 6-continued

| Sample/Number | RCB | HGB | MCV | MCH | MCHC |
|---|---|---|---|---|---|
| Processed 1 | 1.15 | 34 | 153.0 | 29.9 | 195 |
| Processed 2 | 1.15 | 34 | 155.9 | 29.4 | 189 |
| Processed 3 | 1.26 | 28 | 161.5 | 22.1 | 137 |
| Processed 4 | 0.79 | 24 | 158.4 | 30.8 | 194 |
| Processed 5 | 0.54 | 29 | 162.5 | 54.5 | 335 |
| Processed 6 | 1.04 | 32 | 163.0 | 31.3 | 192 |
| Processed 7 | 1.35 | 45 | 144.7 | 33.0 | 228 |
| Processed 8 | 1.22 | 45 | 135.8 | 36.5 | 269 |

RCB: Red Blood Cell Count (cells × $10^{12}$/liter)
HGB: Hemoglobin (grams/liter)
MCV: Mean Corpuscular Volume (femtoliters)
MCH: Mean Corpuscular Hemoglobin (picograms)
MCHC: Mean Corpuscular Hemoglobin Concentration (grams/liter)

There was macrocytosis of the cells which was present in all the processed samples. Comparable hemoglobin levels were measured in the unprocessed and processed samples. The absolute values were appropriate for the residual dilution. The red blood cells are preserved.

Example 86

Methods

For this experiment, 5 ml of anticoagulated blood was obtained from the same HIV-seronegative donor as in the examples 84 and 85. The blood was centrifuged, and the plasma was removed. The remaining cell pellet was resuspended in 100 ml of the GPO buffer, and centrifuged. This washing process was repeated a total of three times. The final pellet was resuspended in 100 ml of the SCPD buffer and distributed in 25 ml aliquots, in T25 tissue culture flasks, with all four aliquots being retained for further manipulation. Two flakes were subject to the process, while the other two were retained as control, unprocessed flasks. After the processing, the contents of each of the flasks was observed and a visual determination of the cells' capacity to absorb oxygen (turning a brighter red on exposure to ambient air) was made. Following this, the contents of the flasks were aspirated and centrifuged, with the residual pellet resuspended in a small volume of buffer. A complete hemogram was performed on these re-concentrated study samples.

As in Examples 84 and 85, a separate aliquot of blood was obtained from the donor when the study sample was taken. A complete hemogram was performed on this baseline sample. As the study samples were re-concentrated to 33–50% of their original state, direct comparisons of a number of specific parameters would be possible with the baseline sample.

Results

On visual inspection, there were no appreciable differences between the processed and unprocessed study samples. Specifically, there appeared to be a uniform distribution of well suspended cells. On exposure to ambient air, the contents of all flasks became somewhat brighter red. No specific quantitative measurements of oxygenation were made.

Red blood cell parameters for the baseline sample as well as for the unprocessed and processed study samples are shown in Table 7. The abbreviations used in Table 7 are defined under Table 6.

TABLE 7

| Sample/Number | RCB | HGB | MCV | MCH | MCHC |
|---|---|---|---|---|---|
| Baseline | 4.75 | 153 | 95.0 | 32.3 | 339 |
| Unprocessed-1 | 0.93 | 30 | 151.5 | 32.3 | 213 |
| Unprocessed-2 | 0.92 | 30 | 155.5 | 32.1 | 207 |
| Processed-1 | 0.82 | 27 | 156.5 | 32.8 | 209 |
| Processed-2 | 0.81 | 26 | 152.6 | 32.4 | 212 |

This experiment was designed to more closely approximate conditions of red blood cells to be transfused into a patient, and was consequently conducted at higher volumes. On a preliminary basis, it does not appear that the process impairs the red blood cells' ability to carry oxygen, although this should be measured more formally. Interestingly, in this experiment, there was no difference in cell size between the processed and unprocessed samples, both being large compared to baseline. Comparable hemoglobin levels were measured in all the study samples.

Example 87

In this experiment, Immunoglobulin G (IgG) was irradiated in lyophilized form.

Method

The results of HPLC analysis of IgG are given in Table 8. As the results demonstrate, the product appears to be unaffected after being irradiated to a dose of 25 kGy at room temperature when the irradiation is delivered at a rate of approximately 0.7 kGy/hr. This has not been previously demonstrated.

TABLE 8

| Parameter | Control (%) | Irradiated (%) |
|---|---|---|
| Polymer (must be >2%) | 1 | 1 |
| Dimer | 10 | 13 |
| Monomer | 88 | 84 |
| Low Molecular Weight | 1 | 2 |

The results presented by Gergely, et al., using freeze dried IgG showed that a portion of the protein was insoluble after an irradiation dose of 12 kGy to 25 kGy at standard irradiation dose rates. (Gergely, J., et al., "Studies of Gama-Ray-Irradiated Human Immunoglobulin G." SM-92/12 I.A.E.A.). In contrast, using the present method at a dose rate of approximately 0.7 kGy/hr, none of the protein was insoluble. This would indicate that little or no change or degradation of the protein occurred. Further, Gergely, et al., found that a liquid formulation of human IgG lost all of its activity after irradiation. In studies using the present method on intravenous immunoglobulin (IVIG) in liquid form, it was shown that greater than 70% of a specific antibody in hyperimmune IVIG was retained.

Example 88

In this experiment, alpha 1 proteinase inhibitor and fibrinogen were irradiated in lyophilized form.

Method

The samples were placed in a Gammacell 220 and irradiated according to the present process to a total dose of 25 kGy. Samples were then returned to the laboratory for analysis. The dose rate was 0.72 kGy/hr.

Results

The alpha 1 proteinase inhibitor, both treated and control, were 40% of a standard normal pooled plasma sample. The Mancini radial immunodiffusion technique was used as the assay.

The topical fibrinogen complex vials were reconstituted in 10 ml of water. Protamine sulphate vials were reconstituted in 10 ml of water. Protamine sulphate at a concentration of 10 mg/ml was added to the samples. There was instant formation of monomer in all three preparations.

Example 89

In this experiment, Factors VII, VIII and IV were irradiated in lyophilized form.
Method
The samples were placed in a Gamacell 220 and irradiated to various total doses at a dose rate of approximately 1 kGy/hr.
Results
Factor VII retained 67% activity at 20 kGy and 75% at 10 kGy. Factor VIII retained 77% activity at 20 kGy and 88% at 10 kGy. Similarly, Factor IV showed an activity level of 70% at 20 kGy and 80% at 10 kGy.

To our knowledge, no one has been able to achieve these results by irradiating the Factors at ambient temperature to such a high dose of radiation with such little loss of activity. This is in direct contrast with the results of Kitchen, et al., "Effect of Gamma Irradiation on the Human Immunodeficiency Virus and Human Coagulation Excellent results were found for the three Factors Proteins," Vox Sang 56:223–229 (1989), who found that "the irradiation of lyophilized concentrates is not a viable procedure." Similarly, Hiemstra, et al., "Inactivation of human immunodeficiency virus by gamma radiation and its effect on plasma and coagulation factors," Transfusion 31:32–39 (1991), also concluded that "Gamma radiation must be disregarded as a method for the sterilization of plasma and plasma-derived products, because of the low reduction of virus infectivity at radiation doses that still give acceptable recovery of biologic activity of plasma components."

Example 90

In this experiment, red blood cells were irradiated at a dose rate of 0.5 kGy/hr for periods of time ranging from 7.5 to 90 minutes in order to remove bacterial contaminants.
Method Red blood cells were collected from a healthy donor in EDTA, washed 3 times with GPO solution and resuspended in DPC to provide a 1:20 dilution based on the original blood volume. The cell suspension was then subdivided into 14 tubes. To seven of the tubes, approximately $1.0 \times 10^4$ Staphylococcus epidermidia were added. The cells were placed on ice for transport to the irradiation facility. All of the samples were placed in the chamber at ambient temperature and irradiated at 0.5 kGy/hr for periods of time to give total doses of 0.625, 0.125, 0.250, 0.375, 0.500 and 0.750 kGy, respectively. The samples were removed and agitated at each time point and placed on ice for transport either to the microbiology lab or the hematology lab for analysis.
Results The results of the microbiology assays are given in Table 9.

TABLE 9

| Radiation Dose (kGy) | Time (min.) | Number Surviving |
| --- | --- | --- |
| 0 | | 92,200 |
| 0.625 | 7.5 | 84,500 |
| 0.125 | 15 | 35,000 |
| 0.250 | 30 | 10,067 |

TABLE 9-continued

| Radiation Dose (kGy) | Time (min.) | Number Surviving |
| --- | --- | --- |
| 0.375 | 45 | 1,800 |
| 0.500 | 60 | 250 |
| 0.750 | 90 | 0 |

Thus, a dose of 0.75 kGy provides a 4.5 $\log_{10}$ reduction in bacterial survivors. This represents a significant safety factor for blood. Further, the D10 value is approximately 0.125 kGy which corresponds well with the values reported in the literature for similar species of staphylococcus (B. A. Bridges, "The effect of N-Ethylmaleimide on the radiation sensitivity of bacteria," J. Gen. Microbiol. 26:467–472 (1962), and Jacobs, G. P. and Sadeh, N., "Radiosensitization of Staphyloccocus aureus by p-hydroxybenzoic acid," Int. J. Radiat. Biol. 41:351–356 (1982).

This experiment demonstrates that red blood cells can be safely irradiated by the present method to a dose of 0.75 kGy at room temperature with no loss of cell function.

Example 91

In this experiment the protective effects of certain stabilizers were evaluated using lyophilized anti-insulin monoclonal immunoglobulin exposed to 45 kGy of low dose gamma irradiation. The stabilizers tested were: sodium ascorbate, methionine, and lipoic acid.
Method In 2 ml glass vials, a 0.5 ml total volume was lyophilized containing 50 μg anti-insulin monoclonal immunoglobulin, 5 mg bovine serum albumin (1%) and either no stabilizer or 50 mM of the stabilizer of interest. The samples were stoppered under vacuum. Samples were irradiated with gamma radiation (45 kGy total dose, dose rate 1.83 kGy/hr, temperature 4° C.) and then reconstituted with water.

Immunoglobulin binding activity of independent duplicate samples was determined by a standard ELISA protocol: 96-well microtitre plates were coated overnight with 2.5 μg/ml insulin antigen. Three-fold serial dilutions of anti-insulin monoclonal antibody samples starting at 5 μg/ml were used. Goat anti-mouse Ig conjungated to phosphatase used at 50 ng/ml. Sigma 104 alkaline phosphatase substrate was used at 1 mg/ml in DEA buffer. Binding activity was determined by absorbance at 405–620 nm.

Relative protection was determined by estimating the shift in the titration curve (i.e. concentration of immunoglobulin needed to observe the same amount of binding) of the irradiated sample compared to an unirradiated sample at approximately 50% of the maximum absorbance signal for the unirradiated sample.
Results Lyophilized samples containing no stabilizer retained 50% of immunoglobulin avidity following irradiation with 45 kGy gamma irradiation. This is in contrast to previous results in which 45 kGy of gamma radiation destroyed essentially all the activity of immunoglobulin when it was irradiated in solution. Thus, it is apparent that the reduction in residual water content by lyophilizing afforded significant protection on its own to the monoclonal immunoglobulin.

The addition of sodium ascorbate provided full recovery of activity after irradiation of the sample. Both methionine and lipoic acid provided significant recovery of activity (76–83%) of activity after irradiation as compared to the unirradiated sample. Similar results (65% recovery of activity) were also seen for pupurogalin.

Example 92

In this experiment, the protective effects of certain stabilizers were evaluated using lyophilized anti-insulin monoclonal immunoglobulin exposed to 45 kGy of low dose gamma irradiation. The stabilizers tested were: sodium ascorbate, N-acetyl cysteine, glutathione and mixtures of urate/trolox and ascorbate/urate/trolox.

Method

In 3 ml glass vials, a 1.0 ml total volume was lyophilized containing 100 μg anti-insulin monoclonal immunoglobulin, 10 mg bovine serum albumin (1%) and either no stabilizer or the stabilizer of interest. The samples were stoppered under vacuum. Samples were irradiated with gamma radiation (45 kGy total dose, dose rate 1.83 kGy/hr, temperature 4° C.) and then reconstituted with 1.0 ml water.

Immunoglobulin binding activity of independent duplicate samples was determined by a standard ELISA protocol: Maxisorb plates were coated overnight with 2.5 μg/ml insulin antigen. Three-fold serial dilutions of anti-insulin monoclonal immunoglobulin samples starting at 5 μg/ml were used. Goat anti-mouse Ig conjugated to phosphatase was used at 50 ng/ml. Binding activity was determined by absorbance at 405–620 nm.

Relative protection was determined using a parallel line analysis software package (PLA 1.2 from Stegmann Systemberatung).

Results

Lyophilized samples containing no stabilizer retained 70% of immunoglobulin avidity following irradiation with 45 kGy gamma irradiation. This is in contrast to previous results in which 45 kGy of gamma radiation destroyed essentially all the activity of immunoglobulin when it was irradiated in solution. Thus, it is apparent that the reduction in residual water content by lyophilizing afforded significant protection on its own The presence of sodium ascorbate increased recovery by 20%, i.e. such that there is 90% avidity recovered after irradiation. The remaining stabilizers resulted in recovery of 77–84% of avidity.

Example 93

In this experiment, the protective effects of primary lyophilizing (which leaves a relatively "high moisture" content in the product) and the combination of both primary and secondary lyophilizing (which results in a product with relatively "low moisture") on the radiation sensitivity of a monoclonal immunoglobulin were determined.

Methods

In 3 ml glass vials, 1.0 ml total volume was lyophilized (using either only primary or a combination of both primary and secondary drying) containing 100 μg anti-insulin monoclonal immunoglobulin, 10 mg bovine serum albumin (1%) and either no stabilizer or 100 mM of sodium ascorbate. The samples were stoppered under vacuum. Samples were irradiated with gamma radiation (45 kGy total dose, dose rate between 2.03 and 2.13 kGy/hr, temperature 4° C.) and then reconstituted with 1.0 ml water.

Immunoglobulin binding activity of independent duplicate samples was determined by a standard ELISA protocol: Maxisorb plates were coated overnight with 2.5 μg/ml insulin antigen. Three-fold serial dilutions of anti-insulin mAb samples starting at 5 μg/ml were used. Goat anti-mouse Ig conjugated to phosphatase was used at 50 ng/ml. Binding activity was determined by absorbance at 405–620 nm.

Results

In the absence of a stabilizer, there was better recovery of the anti-insulin immunoglobulin after irradiation from the samples that had undergone the secondary "low moisture" drying cycle, i.e., a lower total moisture content in the absence of a stabilizer improved recovery.

In the presence of the stabilizer, however, there was very good recovery of antibody activity after 45 kGy irradiation, irrespective of whether the sample had undergone only the primary "high moisture" drying cycle or had also undergone the secondary "low moisture" drying cycle.

Example 94

In this experiment, the protective effect of certain stabilizers on the activity of lyophilized anti-insulin monoclonal immunoglobulin was determined. The stabilizers tested were: sodium ascorbate; trolox/urate/ascorbate mixtures; and N-acetyl cysteine.

Methods

Anti-insulin monoclonal immunoglobulin supplemented with 1% of human serum albumin (and, optionally, 5% sucrose) was lyophilized, stoppered under vacuum, and irradiated (total dose 45 kGy; dose rate between 1.83 and 1.88 kGy/hr) Immunoglobulin binding activity was determined using the standard ELISA protocol described above.

Results

Irradiation of lyophilized anti-insulin immunoglobulin supplemented with 1% HSA to a dose of 45 kGy resulted in an average loss of avidity of about 33%. The addition of the following stabilizers significantly improved recovery: 20 mM sodium ascorbate (100% recovery); 200 μM trolox/1.5 mM urate/20 mM ascorbate (87% recovery); 20 mM N-acetyl cysteine (82% recovery The addition of 5% sucrose to the lyophilized immunoglobulin containing 1% HSA resulted in an average loss of avidity of about 30% when irradiated to a dose of 45 kGy. The addition of the following stabilizers significantly improved recovery: 20 mM sodium ascorbate (88% recovery); 200 μM trolox/1.5 mM urate/20 mM ascorbate (84%) recovery); 20 mM Nacetyl cysteine (72% recovery).

Example 95

In this experiment, the protective effect of stabilizers (ascorbate) on the activity of lyophilized anti-insulin monoclonal immunoglobulin was determined when the sample was irradiated at a high dose rate (30 kGy/hr).

Methods

Anti-insulin monoclonal immunoglobulin was lyophilized and irradiated at a rate of 30 kGy/hr (total dose 45 kGy). Immunoglobulin binding activity was determined using the standard ELISA protocol described above.

Results

Irradiation of lyophilized anti-insulin immunoglobulin to a dose of 45 kGy resulted in an average loss of activity of about 32%. The addition of 20 mM sodium ascorbate provided 85% recovery of avidity compared to an unirradiated sample.

Example 96

In this experiment, an IgM monoclonal immunoglobulin specific for murine $IgG_3$ was irradiated at a low dose rate in the presence or absence of a stabilizer.

Method

Liquid rat anti-murine $IgG_3$ monoclonal IgM (in a PBS buffer with 10 mM sodium azide; concentration of antibody was 666 ng/pl) was irradiated at a rate of 1.8 kGy/hr to a total dose of either 10 kGy or 45 kGy. Samples either contained no stabilizer or a stabilizer mixture containing 20 mM citrate, 300 μM urate and 200 mM ascorbate.

Immunoglobulin activity was analyzed by standard ELISA protocol using murine IgG3 as the coating antigen and a phosphatase-conjugated anti-rat 1 gM detection antibody.

Results

Liquid samples containing no stabilizer lost all functional immunoglobulin activity following irradiation with either 10 kGy or 45 kGy gamma irradiation. The presence of a stabilizer, however, provided full recovery of activity following irradiation with 10 kGy gamma radiation and 88% recovery of activity following irradiation with 45 kGy gamma radiation.

Example 97

In this experiment, the protective effects of certain stabilizers were evaluated using immobilized anti-human insulin monoclonal immunoglobulin exposed to 45 kGy of low dose-rate gamma irradiation. The stabilizers tested were: sodium ascorbate, reduced glutathione, sodium formaldehyde sulfoxylate, and polypropylene glycol.

Method

Two plates were coated with 100 µl/well of freshly prepared 2 µg/ml anti-insulin immunoglobulin in coating buffer overnight at 4° C. The plates were washed briefly three times with PBS. A two-fold dilution series of each stabilizer in PBS was prepared. 100 µl of a selected stabilizer solution was added to each well. The plates were covered tightly with a cap mat. One plate was irradiated at 1.92 kGy/hr for a total of 45 kGy at 4° C. The control plate received 0 kGy and was stored at 4° C.

Immunoglobulin binding activity was determined by a standard ELISA protocol. The plate wells were emptied and were washed four times with a full volume of PBS. A full volume of blocking buffer (approximately 380 µl) was added to all wells and incubated for two hours at 37° C. All wells were washed four times with TBST (TBS pH 7.4 with 0.05% TWEEN 20). One hundred µl of 50 ng/ml biotin-labelled insulin in binding buffer was added to each well. The plates were covered with a plate sealer and incubated at 37° C. while shaking (LabLine titer plate shaker set at 3) for 1.5 hours. The plates were then washed four times with TBST. One hundred µl of 0.5 µg/ml phosphatase labelled Streptavidin (stock diluted 1:1000 in binding buffer) was added to each well. The plates were covered with a plate sealer and incubated at 37° C. for one hour with shaking. The plates were then washed four times with TBST. One hundred µl of 1 mg/ml Sigma 104 phosphatase substrate in DEA buffer was added to each well. The plates were then incubated at 37° C. with shaking. Absorbance was determined at 405 nm–628 nm at 5 minute intervals.

Results

Sodium ascorbate exhibited a dose-dependent protective effect. Samples containing between 31–250 mM of sodium ascorbate exhibited 73–81% greater retained activity.

Samples containing glutathione exhibited approximately 25% greater retention of monoclonal immunoglobulin activity, that was dose dependent up to a glutathione concentration of about 31 mM.

Samples treated with sodium formaldehyde sulfoxylate exhibited approximately 50% greater retained activity than control samples at a stabilizer concentration of 31 mM.

All three forms of polypropylene glycol [i.e., polypropylene P400 (Fluka 81350); polypropylene P1200 (Fluka 81370); and polypropylene P2000 (Fluka 81380)] exhibited a protective effect. Samples treated with polypropylene glycol exhibited approximately 50–60% increased retention of activity relative to control samples.

Example 98

In this experiment, the optimal concentration of sodium ascorbate to protect immobilized anti-insulin monoclonal immunoglobulins from 45 kGy of gamma irradiation was determined. It was also determined whether the presence of 1.5 mM uric acid has any effect on the stabilizing nature of ascorbate of immobilized monoclonal immunoglobulin exposed to 45 kGy gamma irradiation.

Method

Two plates were coated overnight at 4° C. with 100 µl of 2.5 µg/ml anti-insulin monoclonal immunoglobulin in coating buffer. The coating solution was discarded and the wells washed two times with PBS. Twenty-five µl of 4× ascorbate solution was added to appropriate wells. Seventy-five µl of water was added to the urate-free wells (rows a–d). Twenty five µl of water was added to the urate containing wells (rows e–h). Fifteen µl of 3 mM urate was added to the urate containing wells (rows e–h). The plates were covered with a 96-well cap mat. One plate was irradiated with gamma radiation at 1.9 kGy/hr for a total of 45 kGy at 4° C. The other plate was stored at 4° C. as a travel control.

Immunoglobulin binding activity was determined by a standard ELISA protocol as follows. The well contents were removed, and the wells washed twice with a full volume of PBS. Non-specific binding sites were blocked by adding a full volume of blocking buffer (approximately 380 µl) to all wells and incubated for two hours at 37° C. All wells were washed three times with TBST. One hundred µl of 10 ng/ml insulin-biotin in binding buffer was added to each well (stock diluted 1:100,000 in binding buffer). The plates were covered with a plate sealer and incubated at 37° C. with shaking (LabLine titer plate shaker set at three) for one hour. The plates were washed with TBST for four sets of two washes each set, usually leaving five minutes between each set. One hundred pl of 25 ng/ml phosphatase-labelled Streptavidin (stock diluted 1:20,000 in binding buffer) was added to each well. Plates were covered with a plate sealer and incubated at 37° C. for one hour with shaking. Each plate was washed with TBST for four sets of two washes each set, usually leaving approximately five minutes between each set. One hundred µl of 1 ng/ml Sigma 104 phosphatase substrate in DEA buffer was added to each well.

The plates were incubated at ambient temperature with nutation. Absorbance was determined at 405 nm–620 nm.

Results

It was determined that the optimal concentration of sodium ascorbate necessary to provide maximal protection of immobilized anti-insulin monoclonal immunoglobulins in an aqueous environment (in the absence of uric acid) is approximately 150 mM. Approximately 50% recovery of the anti-insulin binding activity was achieved at a concentration of approximately 150 mM ascorbate. The addition of 1.5 mM uric acid resulted in a slight left shift in the ascorbate dose curve (~5 mM) and appeared to cause maximal recovery of activity to be achieved at a lower concentration of ascorbate (~30 mM).

Example 99

In this experiment, the optimal concentration of sodium ascorbate to protect immobilized monoclonal immunoglobulin from 45 kGy gamma irradiation was determined. The experiment also determined whether the presence of 2.25 mM of uric acid affects the stabilizing effect of ascorbate.

Method

Two plates were coated overnight at 4° C. with 100 µl of 2.5 µg/ml anti-insulin monoclonal immunoglobulin in coating buffer. The coating solution was discarded and the wells washed twice with PBS. Twenty-five µl of 4× ascorbate solution was added to appropriate wells. Seventy-five µl of water was added to the urate-free wells (rows a–d). Seventy-five μl of 3 mM urate stock was added to the urate-containing wells (rows eh) (f.c.=2.25 mM). The plates were covered with a 96-well cap mat. One plate was irradiated with gamma radiation at 1.9 kGy/hr for a total of 45 kGy at 4 W. The other plate was stored at 4 W as a travel control.
Results The optimal concentration of sodium ascorbate necessary to provide maximum protection of immobilized anti-insulin monoclonal immunoglobulin in an aqueous environment (in the absence of uric acid) was determined to be approximately 70 mM. The addition of uric acid (2.25 mM) resulted in a slight left shift of the ascorbate dose curve (~5 mM) and appeared to cause maximum recovery of activity to be achieved at a lower concentration of ascorbate (Q25 mM). It was found that there is a biphasic nature to the irradiated samples without uric acid. Recovery improved significantly between 0–20 mM ascorbate, leveled off from 20–50 mM ascorbate, and then went up again until maximum recovery was observed at approximately 70 mM ascorbate.

Example 100

In this experiment, the protective effect of various stabilizers on gamma irradiated freeze-dried anti-insulin monoclonal immunoglobulin supplemented with 1% human serum albumin (HSA) and 5% sucrose was evaluated. The stabilizers tested were: ascorbate (20 mM); a mixture of trolox (200 mM), urate (1.5 uM), and ascorbate (20 mM); n-acetyl-1-cysteine (20 mM); reduced glutathione (20 mM); and the dipeptide, Gly—Gly (20 mM).
Method Samples were freeze-dried for approximately 64 hours and stoppered under vacuum and sealed with an aluminum, crimped seal. Samples were irradiated at a dose rate of 1.83–1.88 kGy/hr to a total dose of 45.1–46.2 kGy at 4° C.

Monoclonal immunoglobulin activity was determined by a standard ELISA protocol. Maxisorp plates were coated with human recombinant insulin at 2.5 μg/ml overnight at 4° C. The plate was blocked with 200 μl of blocking buffer (PBS, pH 7.4, 2% BSA) for two hours at 37° C. and then washed six times with wash buffer (TBS, pH 7, 0.05% TWEEN 20). Samples were re-suspended in 500 μl of high purity water (100 ng/μl), diluted to 5 μg/ml in a 300 μl U-bottomed plate coated for either overnight or two hours with blocking buffer. Serial 3-fold dilutions were performed, with a final concentration of 0.0022 μg/ml. Plates were incubated for one hour at 37° C. with agitation and then washed six times with a wash buffer. Phosphatase-labeled goat anti-mouse IgG (H+L) was diluted to 50 ng/ml in binding buffer and 100 μl was added to each well. The plate was incubated for one hour at 37° C. with agitation and washed six times with wash buffers. One hundred μl of Sigma104 substrate (1 mg/ml in DEA buffer) was added to each well and reacted at room temperature. The plate was read on a Multiskan MCC/340 at 405 nm with the 620 nm absorbance subtracted.
Results Freeze-dried anti-insulin monoclonal immunoglobulin, supplemented with 1% HSA, gamma irradiated to 45 kGy resulted in an average loss in activity of 1.5 fold (average loss in avidity of 33%)

Samples irradiated to 45 kGy in the presence of stabilizers gave varying results:

20 mM ascorbate=~100% recovery 200 uM trolox, 1.5 mM urate, 20 mM ascorbate=~87% recovery 20 mM, n-acetyl-1-cysteine=82% recovery 20 mM reduced glutathione=~76% recovery 20 mM Gly—Gly=~100% recovery Adding 5% sucrose to freeze-dried anti-insulin monoclonal immunoglobulin containing 1% HSA resulted in an average recovery of 70% of the activity in the sample irradiated to 45 kGy (average loss in activity of approximately 1.5 fold or approximately 30% loss in avidity)

The samples that radiated to 45 kGy in the presence of the aforementioned stabilizers had reduced activities upon addition of 5% sucrose:

20 mM ascorbate=88% recovery 200 uM trolox, 1.5 mM urate, 20 mM ascorbate=~84% recovery 20 mM n-acetyl-1-cysteine=~72% recovery 20 mM reduced glutathione=~69% recovery 20 mM gly—gly=79% recovery Similar results have been obtained upon the addition of 20 mM ascorbate, 20 mM Gly—Gly or the addition of 20 mM of both ascorbate and Gly—Gly to another monoclonal IgG preparation of different specificity (anti-Ig Lambda Light Chain).

Example 101

In this experiment, the protective effect of ascorbate (asc, 20 mM), ascorbate (20 mM)/urate (1.5 mM)/trolox (200 μM) cocktail (AUT), n-acetyl-cysteine (neutral form: NAC-n, acidic form: NAC-a, both at 20 mM), Gly—Gly (20 mM), reduced glutathione (GSH, 20 mM), diosmin (39.3 μM) and silymarin (246 μM) on lyophilized anti-insulin monoclonal immunoglobulin was evaluated.
Method In 3 ml glass vials, 1.0 ml total volume containing 100 μg anti-insulin monoclonal immunoglobulin, with 10 mg BSA (1%) and either no stabilizer or the stabilizer of interest was lyophilized. Samples were irradiated with gamma radiation (45 kGy total dose, dose rate 1.83 kGy/hr, temperature 4° C.) and then reconstituted with 1 ml of water. Karl Fischer moisture analysis was performed on the quadruplicate samples that did not contain immunoglobulin.

Immunoglobulin binding activity of independent duplicate samples was determined by a standard ELISA protocol: Maxisorp plates were coated overnight with 2.5 μg/ml insulin antigen. Three-fold serial dilutions of anti-insulin monoclonal immunoglobulin samples starting at 5 μg/ml were used. Goat anti-mouse phosphatase conjugate was used at 50 mg/ml. Relative potency values of irradiated samples compared to their corresponding unirradiated sample were calculated using the parallel line analysis software package (PLA 1.2 from Stegmann Systemberatung). Mass spectroscopy analysis was performed by M-scan, Inc. of Westchester Pa.
Results Irradiation of lyophilized anti-insulin monoclonal immunoglobulin in the presence of 1% bovine serum albumin resulted in the loss of approximately 30% avidity (relative to unirradiated samples) of the immunoglobulin for its immobilized antigen. The addition of ascorbate alone improved the recovery by 20%, such that there was approximately 90% avidity recovered after irradiation. The addition of ascorbate/urate/trolox cocktail, the dipeptide Gly—Gly, neutral n-acetyl-cysteine, reduced glutathione, or silymarin resulted in recovery of 77–84% avidity.

Similar results have been obtained upon the addition of 200 mM ascorbate, 200 mM Gly—Gly or the addition of 200 mM of both ascorbate and Gly—Gly to two other monoclonal IgG preparations of different specificity (anti-Ig Lambda Light Chain and anti-IgG1).

Example 102

In this experiment, the stability of anti-insulin monoclonal immunoglobulin irradiated in the liquid form in the presence or absence of ascorbate was evaluated.

Method

Anti-insulin monoclonal immunoglobulin was diluted to 1 mg/ml and irradiated at 4° C. in the presence or absence of 200 mM ascorbate to a total dose of 0, 15, or 45 kGy of gamma radiation.

Immunoglobulin binding activity of independent duplicate samples was determined by a standard direct ELISA protocol generally as described in the previous example.

Results

The addition of 200 mM ascorbate resulted in recovery of 100% of immunoglobulin binding activity of samples irradiated with 15 kGy of radiation and recovery of 71.7% and 80.4% of the activity of samples radiated with 45 kGy of radiation compared to the in-house dilution control and the 0 kGy plus ascorbate control, respectively. As determined by polyacrylamide gel electrophoresis, irradiation of the anti-insulin immunoglobulins and the absence of the stabilizer resulted in protein aggregation as evidenced by high molecular weight bands on polyacrylamide gels. Additionally, a significant loss of material was apparent. The addition of 200 mM ascorbate had a protective effect on the immunoglobulins irradiated at 15 kGy and 45 kGy, as demonstrated by the recovery of an intact $IgG_1$ band and as well as heavy and light chain bands.

When duplicates of the 15 kGy plus 200 mM ascorbate samples were averaged, the antigen binding activity was not significantly different from that of the dilution control. In contrast, irradiating the samples containing ascorbate to 45 kGy resulted in an average 2-fold and 2.5-fold decrease in avidity when compared to the in-house dilution control and stock control, respectively. The SDS-PAGE analysis indicated that in the absence of ascorbate, irradiating the anti-insulin monoclonal immunoglobulins resulted in significant loss of material and a generation of high molecular weight aggregate. The addition of 200 mM ascorbate prevented aggregate formation and resulted in recovery of approximately 80% and approximately 50% of the immunoglobulins following irradiation to 15 kGy and 45 kGy, respectively.

Example 103

This experiment was conducted to determine whether low pH (4.5) diminishes the stabilizing effect of L-ascorbic acid on monoclonal immunoglobulin irradiated to 45 kGy with gamma radiation.

Method

An anti-human insulin monoclonal Ig (Anti-Human Insulin Monoclonal Immunoglobulin, Purified Clone #7F8;BioDesign International #E86102M, lot 7125000) was irradiated as a liquid at a rate of 1.774 kGy/hr ($^{60}$Co) in the presence and absence of 200 mM L-Ascorbic acid to a total dose of 45 kGy, at pH 6.8 and 4.5. Following irradiation, the samples were assayed for their antigen-specific binding capability in an ELISA assay using insulin-coated plates as targets. Structural analysis of the Ig was done via standard SDS-PAGE electrophoresis under both reduced and non-reduced conditions.

Results

The ELISA functional assay results showed that recovery of the monoclonal immunoglobulin in the presence of ascorbate was not dependent on pH. The graphs for pH 6.8 and 4.5 were virtually superimposable. A slight loss of activity was seen at both pH values upon the addition of ascorbic acid and again following irradiation, however the magnitude of this reduction was small in comparison to the complete loss of activity seen when irradiation takes place in the absence of ascorbate.

SDS-PAGE electrophoresis gels showed a complete destruction of the immunoglobulin at 45 kGy in the absence of ascorbic acid at both pH 3.8 and pH 4.5. The addition of 200 mM ascorbic acid maintained the same apparent structure upon irradiation. A pH of 4.5 may have inhibited aggregation.

These results indicate that, in the presence of 200 mM ascorbic acid, monoclonal Ig could be irradiated to at least 45 kGy while retaining structure and activity at both pH 6.7 and 4.5.

Example 104

In this experiment the level of viral inactivation and monoclonal immunoglobulin activity retention in anti-insulin monoclonal immunoglobulin infected with porcine parvovirus (PPV) irradiated with $^{60}$Co gamma radiation at an approximate rate of 1.8 kGy/hour at 4° C. was evaluated.

Method

PPV was utilized as a model virus for Human Parvovirus B19, a non-enveloped virus that is considered the most difficult virus of concern in human-sourced biologics and a close analog of the other members of the Parvovirus family that are also considered the most difficult viruses of concern in animal-sourced biologics.

A high titre PPV stock was spiked into a preparation of a monoclonal immunoglobulin directed against insulin. A protectant (sodium ascorbate) was added to some samples at a final concentration of 200 mM.

The samples to be irradiated were exposed to $^{60}$Co radiation at an approximate rate of 1.8 kGy/hour at 4° C.

After irradiation of some of the samples, aliquots of the spiked samples were taken and used to titre the amount of remaining infective virus particles. Briefly, the samples were assayed in a viral detection bioassay known as a Cytopathic Effect test (CPE). A cell line capable of being infected by the PPV virus and lysed by it (Porcine Kidney cells, also known as PK-13 cells) were added to 96-well assay plates to form a monolayer of approximately 70% confluence. Quadruplicate aliquots of the samples were added to the wells in a limiting-dilution series (5-fold dilutions). The plates were then incubated for 7–8 days and then examined to determine if viable cells remained in the wells. The resulting data was analysed using a Limiting-Dilution method as described by Karber to determine the viral.

Results

The application of gamma radiation effectively inactivated the virus in a dose-dependent manner. The addition of 200 mM sodium ascorbate to the monoclonal immunoglobulin resulted in a significant reduction in the viral inactivation at lower doses, but at higher doses this effect was much smaller. The application of 45 kGy of gamma radiation to samples containing ascorbate resulted in greater than 4 logs of viral inactivation.

Example 105

This experiment was conducted to evaluate the level of activity retention achieved when irradiating monoclonal immunoglobulins in both liquid and lyophilized forms with E-beam radiation in the presence or absence of sodium ascorbate.

Method

Anti-Insulin IgG$_1$ was tested in liquid and after having been lyophilized. Samples were prepared both with and without 200 mM and 20 mM sodium ascorbate in the liquid and lyophilized state, respectively.

The samples to be irradiated (both with and without ascorbate) were exposed to E-beam irradiation at an approximate rate of 45 kGy/hour at 77–88° F. The E-beam energy was 7 MeV and a total dose of approximately 45 kGy was given. Control samples consisted of unirradiated samples with and without ascorbate that traveled to and from the irradiation site, and a reference control sample that did not travel to the irradiation site. During transport the samples were kept at 4° C.

After irradiation the lyophilized samples were reconstituted with distilled water. All samples were then tested in an anti-human insulin ELISA assay as described in Example 100. Approximate measures of the recovery of antigen binding activity were performed by hand as the concentration of Ig that produced approximately 50% of the maximum CD.

Results

When in the liquid state the application of E-beam radiation completely inactivated the Ig. In the presence of ascorbate, there was a clear recovery of activity, but the magnitude was limited.

The lyophilization of the Ig prior to irradiation had a greater effect upon the recovery of activity than the addition of ascorbate alone to the liquid. Approximately 50% of the antigen-binding activity was retained when ascorbate-free Ig was irradiated. The addition of 20 mM ascorbate prior to lyophilization resulted in complete recovery of activity.

Example 106

In this experiment, the effects of gamma irradiation

Preparation of Antioxidant Stock Solutions

The following stock solutions were prepared:

2M sodium ascorbate in water (Spectrum S1349 QP 0839)

2 mM trolox C in DPBS (Aldrich 23,881-3, 02507TS, 53188-07-01)

0.5M lipoic acid (Calbiochem 437692, B34484)

0.5M coumaric acid in ethyl alcohol (Sigma)

1M n-propyl gallate in ethyl alcohol (Sigma P3130, 60K0877)

0.2M L-histidine in PBS (Sigma H8776, 69H1251)

2M D-(+)-trehalose in water (Sigma T9531, 61K7026)

10 mg/ml ergothionine in water (Sigma E7521, 21K1683)

0.04M poly-lysine (Sigma, MW=461)

1M thiourea (Sigma T8656, 11K01781)

Preparation of Ligament Samples

Samples were prepared by cutting ACL in half longitudinally. The lengths of each ACL were measured and used for irradiation. The samples were placed in tubes with the following conditions:

1. ACL in water (Control)
2. ACL+200 mM sodium ascorbate, pH 7.63
3. ACL+0.1M thiourea, pH 6.64
4. ACL+200 mM histidine, pH 8.24
5. ACL+500 mM trehalose, pH 5.36
6. ACL+5 mg/ml ergothionine, pH 6.0
7. ACL+0.01M poly-lysine, pH 5.59
8. ACL dehydrated+(100 μM trolox C, 100 mM coumaric acid, 100 mM lipoic acid, 100 mM-propyl gallate), pH 5.24

Method

ACL's 1–7 described above were incubated for about 1 to about 2 hours with shaking in a shaking incubator at 37° C. For the dehydration (8), the ACL was incubated with polypropylene glycol 400 (PPG400) for 1 hour at 37° C. The PPG400 treated ACL was incubated with the antioxidant mixture described above for 1 hour at 37° C. After about 2 hours of incubation, the ACL tubes were decanted and fresh solutions of antioxidants, or water for 1, were added to each ACL tube. Following this, the tubes ACL's were incubated for 3 days at 4° C., decanted and freeze-dried.

The samples were irradiated with 0 kGy and 45 kGy at 1.677 kGy/hr.

The samples were rehydrated with water for a few hours at room temperature. The length of the ACL's was measured and a small piece was cut from each irradiated ACL. The cut pieces were weighed with the following results:

| Sample Number | O kGy (mg) | 45 kGy (mg) |
|---|---|---|
| 1 | 134.5 | 150.45 |
| 2 | 171.95 | 148 |
| 3 | 288.6 | 183.06 |
| 4 | 229.3 | 226.54 |
| 5 | 260 | 197.5 |
| 6 | 165.14 | 132.68 |
| 7 | 289.34 | 164.88 |
| 8 | 114.5 | 83.93 |

Guanidine CH1 Extraction

The ACL samples were extracted with 4M GuHCl in 0.5M NaOac, pH 5.8, and 5 mM EDTA, 10 mM benzamidine and 1 mM PMSF for a final concentration of 100 mg/ml or wet tissue weight/ml of extraction buffer. The samples were incubated on the nutator for 2 days at 4° C.

Following incubation, the extracts were centrifuged using a tabletop centrifuge and the pellets were transferred into 2 ml tubes and washed 3 times with 2 ml of 0.5M HOAC. Pepsin was added to the pellets at a 1:10 ratio of enzyme to tissue in 0.5N HOAC. The samples were incubated at 4° C. overnight and another portion of pepsin was added to each pellet. The samples were incubated on the nutator at 4° C. overnight.

The samples were centrifuged and washed 3 times with 100 mM Tris, pH 8.0, and 20 mM CaCl$_2$. Trypsin was added at a 1:20 ratio of enzyme to wet weight. The samples were mixed and incubated at 37° C. overnight.

To the pepsin-digested supernatant, NaCl from 5M stock solution was added to a final concentration of 1M. The supernatants were centrifuged for 15 minutes at 22,000 g in a cold room. Collagen gel pellets were resuspended in 1 ml of 0.5N HOAC with gentle mixing at 4° C.

The pepsin digested collagens for the samples were dialyzed against 5 mM HOAC overnight. Determined the OD 218 nm for each collagen preparation. A turbidity assay was performed for these collagens using purified pepsin-digested collagen as a control.

Results

From the SDS-PAGE of the pepsin digest, the antioxidant cocktail treated ACL (8) showed the best recovery compared to other antioxidants. The HMW bands were protected after irradiation in the presence of cocktails. The trypsin digest did not provide any conclusive results.

For the purified pepsin-digested collagen, the PPG dehydration and rehydration with scavenger cocktails showed the best recovery by SDS-PAGE. They yield was 88% for the cocktails compared to 32% for the control (1). Some of the HMW bands were destroyed by irradiation even in the presence of scavenger cocktails. These other scavengers were not effective protecting the collagen in this experiment. One possible explanation is that the scavengers were not absorbed deep inside the ACL, since the ACL's were simply soaked with these scavengers.

The turbidity test assay was not working well for the collagen isolated from these ACL. There could be some other proteins interfering with the assay. However, these collagens could from fibrils. The irradiated collagen in the presence of cocktail scavengers has a lower final turbidity and smaller rate of fibril formation compared to the unirradiated collagen.

Using PPG400 for dehydration of the ACL irreversibly changed the morphology of the ACL, even after rehydration.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The foregoing embodiments and advantages are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A method for sterilizing fetal bovine serum comprising irradiating said fetal bovine serum with gamma radiation at ambient temperature or below at an effective dose rate for a period of time effective to sterilize said fetal bovine serum, wherein said effective dose rate is not constant and comprises a rate between 0.1 kGy/hr to 3.0 kGy/hr for at least a portion of said period of time and a rate of at least 6.0 kGy/hr for at least another portion of said period of time.

2. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time.

3. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time.

4. The method according to claim 1, wherein said effective dose rate comprises a rate between 0.5 kGy/hr to 1.0 kGy/hr for at least a portion of said period of time and a rare of at least 6.0 kGy/hr for at least another portion of said period of time.

5. The method according to claim 1, wherein said irradiating is conducted at a temperature below ambient temperature.

6. The method according to claim 1, wherein said irradiating is conducted at a temperature below the freezing point of said fetal bovine serum.

7. The method according to claim 1, wherein prior to said irradiating said fetal bovine serum contains at least one active biological contaminant selected from the group consisting of bacteria, viruses, mycoplasmas, parvoviruses and prions.

8. The method according to claim 1, wherein prior to said irradiating said fetal bovine serum contains active viruses.

9. The method according to claim 1, wherein prior to said irradiating said fetal bovine serum contains active prions.

10. The method according to claim 1, wherein prior to said irradiating said fetal bovine serum contains active bacteria.

11. The method according to claim 1, wherein prior to said irradiating said fetal bovine serum contains active mycoplasmas.

12. The method according to claim 1, wherein prior to said irradiating said fetal bovine serum contains active parvovixuses.

13. The method according to claim 1, wherein said fetal bovine contains a stabilizer selected from the group consisting of: ascorbic acid or a salt thereof; glutathione vitamin E; albumin; cysteine; uric acid or a salt thereof; methionine; histidine; N-acetyl cysteine; fatty acids, glucose; and mixtures of two or more thereof.

14. The method according to claim 1, wherein said fetal bovine serum contains uric acid or a salt thereof.

15. The method according to claim 1, wherein said fetal bovine serum contains albumin.

16. The method according to claim 1, wherein said fetal bovine serum contains glucose.

17. The method according to claim 1, wherein said fetal bovine serum contains at least one fatty acid.

18. The method according to claim 1, further comprising adjusting the pH of said fetal bovine serum prior to said irradiating.

19. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and said irradiating is conducted at a temperature below ambient temperature.

20. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and said irradiating is conducted at a temperature below ambient temperature.

21. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and said irradiating is conducted at a temperature below ambient temperature.

22. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and said irradiating is conducted at a temperature below the freezing point of said fetal bovine serum.

23. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and said irradiating is conducted at a temperature below the freezing point of said fetal bovine serum.

24. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and said irradiating is conducted at a temperature below the freezing point of said fetal bovine serum.

25. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and prior to said irradiating said fetal bovine serum contains active viruses.

26. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and prior to said irradiating said fetal bovine serum contains active viruses.

27. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and prior to said irradiating said fetal bovine serum contains active viruses.

28. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and prior to said irradiating said fetal bovine serum contains active prions.

29. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and prior to said irradiating said fetal bovine serum contains active prions.

30. The method according to claim 1, wherein said effective dose rate comprises a rate between 0.5 kGy/hr to 1.0 kGy/hr for at least a portion of said period of time and a rate of at least 6.0 kGv/hr for at least another portion of said period of time and prior to said irradiating said fetal bovine serum contains active prions.

31. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and prior to said irradiating said fetal bovine serum contains active bacteria.

32. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and prior to said irradiating said fetal bovine serum contains active bacteria.

33. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and prior to said irradiating said fetal bovine serum contains active bacteria.

34. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and prior to said irradiating said fetal bovine serum contains active mycoplasmas.

35. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and prior to said irradiating said fetal bovine serum contains active mycoplasmas.

36. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and prior to said irradiating said fetal bovine serum contains active mycoplasmas.

37. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and prior to said irradiating said fetal bovine serum contains active parvoviruses.

38. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and prior to said irradiating said fetal bovine serum contains active parvoviruses.

39. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and prior to said irradiating said fetal bovine serum contains active parvoviruses.

40. The method according to claim 1, wherein said effective dose rate comprises a rate between 0.25 kGy/hr to 2.0 kGy/hr for at least a portion of said period of time and a rate of at Least 6.0 kGy/hr for at Least another portion of said period of time and said fetal bovine serum contains albumin.

41. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and said fetal bovine serum contains albumin.

42. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and said fetal bovine serum contains albumin.

43. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and said fetal bovine serum contains glucose.

44. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and said fetal bovine serum contains glucose.

45. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and said fetal bovine serum contains glucose.

46. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and said fetal bovine serum contains uric acid or a salt thereof.

47. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and said fetal bovine serum contains uric acid or a salt thereof.

48. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and said fetal bovine serum contains uric acid or a salt thereof.

49. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and said fetal bovine serum contains at least one fatty acid.

50. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and said fetal bovine serum contains at least one fatty acid.

51. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and said fetal bovine serum contains at least one fatty acid.

52. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and further comprising adjusting the pH of said fetal bovine serum prior to said irradiating.

53. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and further comprising adjusting the pH of said fetal bovine serum prior to said irradiating.

54. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and further comprising adjusting the pH of said fetal bovine serum prior to said irradiating.

55. The method according to claim 1, wherein said irradiating is conducted at a temperature below ambient temperature and further wherein prior to said irradiating said fetal bovine serum contains active prions.

56. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active prions.

57. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active prions.

58. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active prions.

59. The method according to claim 1, wherein said irradiating is conducted at a temperature below the freezing point of said fetal bovine serum and further wherein prior to said irradiating said fetal bovine serum contains active prions.

60. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active prions.

61. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active prions.

62. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active prions.

63. The method according to claim 1, wherein said irradiating is conducted at a temperature below ambient temperature and further wherein prior to said irradiating said fetal bovine serum contains active viruses.

64. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active viruses.

65. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active viruses.

66. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active viruses.

67. The method according to claim 1, wherein said irradiating is conducted at a temperature below the freezing point of said fetal bovine serum and further wherein prior to said irradiating said fetal bovine serum contains active viruses.

68. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active viruses.

69. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active viruses.

70. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active viruses.

71. The method according to claim 1, wherein said irradiating is conducted at a temperature below ambient temperature and further wherein prior to said irradiating said fetal bovine serum contains active bacteria.

72. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active bacteria.

73. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active bacteria.

74. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active bacteria.

75. The method according to claim 1, wherein said irradiating is conducted at a temperature below the freezing point of said fetal bovine serum and further wherein prior to said irradiating said fetal bovine serum contains active bacteria.

76. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active bacteria.

77. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active bacteria.

78. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active bacteria.

79. The method according to claim 1, wherein said irradiating is conducted at a temperature below ambient temperature and further wherein prior to said irradiating said fetal bovine serum contains active mycoplasmas.

80. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active mycoplasmas.

81. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active mycoplasmas.

82. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active mycoplasmas.

83. The method according to claim 1, wherein said irradiating is conducted at a temperature below the freezing point of said fetal bovine serum and further wherein prior to said irradiating said fetal bovine serum contains active mycoplasmas.

84. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active mycoplasmas.

85. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted 86. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active mycoplasmas.

87. The method according to claim 1, wherein said irradiating is conducted at a temperature below ambient temperature and further wherein prior to said irradiating said fetal bovine serum contains active parvoviruses.

88. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active parvoviruses.

89. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active parvoviruses.

90. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active parvoviruses.

91. The method according to claim 1, wherein said irradiating is conducted at a temperature below the freezing point of said fetal bovine serum and further wherein prior to said irradiating said fetal bovine serum contains active parvoviruses.

92. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active parvoviruses.

93. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active parvoviruses.

94. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active parvoviruses.

95. The method according to claim 1, wherein said irradiating is conducted at a temperature below ambient temperature and further wherein said fetal bovine serum contains uric acid or a salt thereof.

96. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein said fetal bovine serum contains uric acid or a salt thereof.

97. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and said fetal bovine serum contains uric acid or a salt thereof.

98. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein, said irradiating is conducted at a temperature below ambient temperature and further wherein said fetal bovine serum contains uric acid or a salt thereof.

99. The method according to claim 1, wherein said irradiating is conducted at a temperature below the freezing point of said fetal bovine serum and further wherein said fetal bovine serum contains uric acid or a salt thereof.

100. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains uric acid or a salt thereof.

101. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains uric acid or a salt thereof.

102. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains uric acid or a salt thereof.

103. The method according to claim 1, wherein said irradiating is conducted at a temperature below ambient temperature and further wherein said fetal bovine serum contains albumin.

104. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein said fetal bovine serum contains albumin.

105. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein said fetal bovine serum contains albumin.

106. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein said fetal bovine serum contains albumin.

107. The method according to claim 1, wherein said irradiating is conducted at a temperature below the freezing point of said fetal bovine serum and further wherein said fetal bovine serum contains albumin.

108. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains albumin.

109. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains albumin.

110. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains albumin.

111. The method according to claim 1, wherein said irradiating is conducted at a temperature below ambient temperature and further wherein said fetal bovine serum contains glucose.

112. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein said fetal bovine serum contains glucose.

113. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein said fetal bovine serum contains glucose.

114. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein said fetal bovine serum contains glucose.

115. The method according to claim 1, wherein said irradiating is conducted at a temperature below the freezing point of said fetal bovine serum and further wherein said fetal bovine serum contains glucose.

116. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains glucose.

117. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains glucose.

118. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains glucose.

119. The method according to claim 1, wherein said irradiating is conducted at a temperature below ambient temperature and further wherein said fetal bovine serum contains at least one fatty acid.

120. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein said fetal bovine serum contains at least one fatty acid.

121. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein said fetal bovine serum contains at least one fatty acid.

122. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein said fetal bovine serum contains at least one fatty acid.

123. The method according to claim 1, wherein said irradiating is conducted at a temperature below the freezing point of said fetal bovine serum and further wherein said fetal bovine serum contains at least one fatty acid.

124. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains at least one fatty acid.

125. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains at least one fatty acid.

126. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein said fetal bovine serum contains at least one fatty acid.

127. The method according to claim 1, wherein said irradiating is conducted at a temperature below ambient temperature, said method further comprising adjusting the pH of said fetal bovine serum prior to said irradiating.

128. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature, said method further comprising adjusting the pH of said fetal bovine serum prior to said irradiating.

129. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature, said method further comprising adjusting the pH of said fetal bovine serum prior to said irradiating.

130. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature, said method further comprising adjusting the pH of said fetal bovine serum prior to said irradiating.

131. The method according to claim 1, wherein said irradiating is conducted at a temperature below the freezing point of said fetal bovine serum, said method further comprising adjusting the pH of said fetal bovine serum prior to said irradiating.

132. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum, said method further comprising adjusting the pH of said fetal bovine serum prior to said irradiating.

133. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum, said method further comprising adjusting the pH of said fetal bovine serum prior to said irradiating.

134. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum, said method further comprising adjusting the pH of said fetal bovine serum prior to said irradiating.

135. The method according to claim 1, wherein said irradiating is conducted at a temperature below ambient temperature and further wherein prior to said irradiating said fetal bovine serum contains active prions, said method further comprising adjusting the pH of said fetal bovine serum prior to said irradiating.

136. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active prions, said method further comprising adjusting the pH of said fetal bovine serum prior to said irradiating.

137. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active prions, said method further comprising adjusting the pH of said fetal bovine serum prior to said irradiating.

138. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active prions, said method further comprising adjusting the pH of said fetal bovine serum prior to said irradiating.

139. The method according to claim 1, wherein said irradiating is conducted at a temperature below the freezing point of said fetal bovine serum and further wherein prior to said irradiating said fetal bovine serum contains active prions, said method further comprising adjusting the pH of said fetal bovine serum prior to said irradiating.

140. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active prions, said method further comprising adjusting the pH of said fetal bovine serum prior to said irradiating.

141. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active prions, said method further comprising adjusting the pH of said fetal bovine serum prior to said irradiating.

142. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active prions, said method further comprising adjusting the pH of said fetal bovine serum prior to said irradiating.

143. The method according to claim 1, wherein said irradiating is conducted at a temperature below ambient temperature and further wherein prior to said irradiating said fetal bovine serum contains active viruses, said method further comprising adjusting the pH of said fetal bovine serum prior to said irradiating.

144. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active viruses, said method further comprising adjusting the pH of said fetal bovine serum prior to said irradiating.

145. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active viruses, said method further comprising adjusting the pH of said fetal bovine serum prior to said irradiating.

146. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active viruses, said method further comprising adjusting the pH of said fetal bovine serum prior to said irradiating.

147. The method according to claim 1, wherein said irradiating is conducted at a temperature below the freezing point of said fetal bovine serum and further wherein prior to said irradiating said fetal bovine serum contains active viruses, said method further comprising adjusting the pH of said fetal bovine serum prior to said irradiating.

148. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active viruses, said method further comprising adjusting the pH of said fetal bovine serum prior to said irradiating.

149. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active viruses, said method further comprising adjusting the pH of said fetal bovine serum prior to said irradiating.

150. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active viruses, said method further comprising adjusting the pH of said fetal bovine serum prior to said irradiating.

151. The method according to claim 1, wherein said irradiating is conducted at a temperature below ambient temperature and further wherein prior to said irradiating said fetal bovine serum contains active bacteria, said method further comprising adjusting the pH of said fetal bovine serum prior to said irradiating.

152. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active bacteria, said method further comprising adjusting the pH of said fetal bovine serum prior to said irradiating.

153. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active bacteria, said method further comprising adjusting the pH of said fetal bovine serum prior to said irradiating.

154. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active bacteria, said method further comprising adjusting the pH of said fetal bovine serum prior to said irradiating.

155. The method according to claim 1, wherein said irradiating is conducted at a temperature below the freezing point of said fetal bovine serum and further wherein prior to said irradiating said fetal bovine serum contains active bacteria, said method further comprising adjusting the pH of said fetal bovine serum prior to said irradiating.

156. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active bacteria, said method further comprising adjusting the pH of said fetal bovine serum prior to said irradiating.

157. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active bacteria, said method further comprising adjusting the pH of said fetal bovine serum prior to said irradiating.

158. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active bacteria, said method further comprising adjusting the pH of said fetal bovine serum prior to said irradiating.

159. The method according to claim 1, wherein said irradiating is conducted at a temperature below ambient temperature and further wherein prior to said irradiating said fetal bovine serum contains active mycoplasmas, said method further comprising adjusting the pH of said fetal bovine serum prior to said irradiating.

160. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active mycoplasmas, said method further comprising adjusting the pH of said fetal bovine serum prior to said irradiating.

161. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active mycoplasmas, said method further comprising adjusting the pH of said fetal bovine serum prior to said irradiating.

162. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active mycoplasmas, said method further comprising adjusting the pH of said fetal bovine serum prior to said irradiating.

163. The method according to claim 1, wherein said irradiating is conducted at a temperature below the freezing point of said fetal bovine serum and further wherein prior to said irradiating said fetal bovine serum contains active mycoplasmas, said method further comprising adjusting the pH of said fetal bovine serum prior to said irradiating.

164. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active mycoplasmas, said method further comprising adjusting the pH of said fetal bovine serum prior to said irradiating.

165. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active mycoplasmas, said method further comprising adjusting the pH of said fetal bovine serum prior to said irradiating.

166. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active mycoplasmas, said method further comprising adjusting the pH of said fetal bovine serum prior to said irradiating.

167. The method according to claim 1, wherein said irradiating is conducted at a temperature below ambient temperature and further wherein prior to said irradiating said fetal bovine serum contains active parvoviruses, said method further comprising adjusting the pH of said fetal bovine serum prior to said irradiating.

168. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active parvoviruses, said method further comprising adjusting the pH of said fetal bovine serum prior to said irradiating.

169. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active parvoviruses, said method further comprising adjusting the pH of said fetal bovine serum prior to said irradiating.

170. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below ambient temperature and further wherein prior to said irradiating said fetal bovine serum contains active parvoviruses, said method further comprising adjusting the pH of said fetal bovine serum prior to said irradiating.

171. The method according to claim 1, wherein said irradiating is conducted at a temperature below the freezing point of said fetal bovine serum and further wherein prior to said irradiating said fetal bovine serum contains active parvoviruses, said method further comprising adjusting the pH of said fetal bovine serum prior to said irradiating.

172. The method according to claim 1, wherein said effective dose rate comprises a rate between 0.25 kGy/hr to 2.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active parvoviruses, said method further comprising adjusting the pH of said fetal bovine serum prior to said irradiating.

173. The method according to claim 1, wherein said effective dose rate comprises a rate between 0.5 kGy/hr to 1.5 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active parvoviruses, said method further comprising adjusting the pH of said fetal bovine serum prior to said irradiating.

174. The method according to claim 1, wherein said effective dose rate comprises a rate between 0.5 kGy/hr to 1.0 kGy/hr for at least a portion of said period of time and a rate of at least 6.0 kGy/hr for at least another portion of said period of time and wherein said irradiating is conducted at a temperature below the freezing point of said fetal bovine serum and further wherein prior to said irradiating said fetal bovine serum contains active parvoviruses, said method further comprising adjusting the pH of said fetal bovine serum prior to said irradiating.

175. The method according to claim 1, wherein said effective dose rate further comprises a rate of at least 16.0 kGy/hr for at least another portion of said period of time.

176. The method according to claim 2, wherein said effective dose rate further comprises a rate of at least 16.0 kGy/hr for at least another portion of said period of time.

177. The method according to claim 3, wherein said effective dose rate further comprises a rate of at least 16.0 kGy/hr for at least another portion of said period of time.

178. The method according to claim 4, wherein said effective dose rate further comprises a rate of at least 16.0 kGy/hr for at least another portion of said period of time.

179. The method according to claim 1, wherein said effective dose rate further comprises a rate of at least 16.0 kGy/hr for at least another portion of said period of time.

180. The method according to claim 6, wherein said effective dose rate further comprises a rate of at least 16.0 kGy/hr for at least another portion of said period of time.

181. The method according to claim 7, wherein said effective dose rate further comprises a rate of at least 16.0 kGy/hr for at least another portion of said period of time.

182. The method according to claim 13, wherein said effective dose rate further comprises a rate of at least 16.0 kGy/hr for at least another portion of said period of time.

183. The method according to claim 18, wherein said effective dose rate further comprises a rate of at least 16.0 kGy/hr for at least another portion of said period of time.

184. The method according to claim 5, wherein said irradiating is conducted at a temperature between 0° C. and −78° C.

185. The method according to claim 5, wherein said irradiating is conducted at a temperature between 0° C. and −40° C.

186. The method according to claim 19, wherein said irradiating is conducted at a temperature between 0° C. and −78° C.

187. The method according to claim 19, wherein said irradiating is conducted at a temperature between 0° C. and −40° C.

188. The method according to claim 20, wherein said irradiating is conducted at a temperature between 0° C. and −78° C.

189. The method according to claim 20, wherein said irradiating is conducted at a temperature between 0° C. and −40° C.

190. The method to according claim 21, wherein said irradiating is conducted at a temperature between 0° C. and −78° C.

191. The method according to claim 21, wherein said irradiating is conducted at a temperature between 0° C. and −40° C.

192. The method according to claim 184, wherein said effective dose rate further comprises a rate of at least 16.0 kGy/hr for at least another portion of said period of time.

193. The method according to claim 185, wherein said effective dose rate further comprises a rate of at least 16.0 kGy/hr for at least another portion of said period of time.

194. The method according to claim 186, wherein said effective dose rate further comprises a rate of at least 16.0 kGy/hr for at least another portion of said period of time.

195. The method according to claim 187, wherein said effective dose rate further comprises a rate of at least 16.0 kGy/hr for at least another portion of said period of time.

196. The method according to claim 188, wherein said effective dose rate further comprises a rate of at least 16.0 kGy/hr for at least another portion of said period of time.

197. The method according to claim 189, wherein said effective dose rate further comprises a rate of at least 16.0 kGy/hr for at least another portion of said period of time.

198. The method according to claim 190, wherein said effective dose rate further comprises a rate of at least 16.0 kGy/hr for at least another portion of said period of time.

199. The method according to claim 191, wherein said effective dose rate further comprises a rate of at least 16.0 kGy/hr for at least another portion of said period of time.

200. The method according to claim 1, wherein the total dose of gamma radiation is at least 25 kGy.

201. The method according to claim 2, wherein the total dose of gamma radiation is at least 25 kGy.

202. The method according to claim 3, wherein the total dose of gamma radiation is at least 25 kGy.

203. The method according to claim 4, wherein the total dose of gamma radiation is at least 25 kGy.

204. The method according to 5, wherein the total dose of gamma radiation is at least 25 kGy.

205. The method according to claim 6, wherein the total dose of gamma radiation is at least 25 kGy.

206. The method according to claim 7, wherein the total dose of gamma radiation is at least 25 kGy.

207. The method according to claim 13, wherein the total dose of gamma radiation is at least 25 kGy.

208. The method according to claim 18, wherein the total dose of gamma radiation is at least 25 kGy.

209. The method according to claim 192, wherein the total dose of gamma radiation is at least 25 kGy.

210. The method according to claim 193, wherein the total dose of gamma radiation is at least 25 kGy.

211. The method according to claim 194, wherein the total dose of gamma radiation is at least 25 kGy.

212. The method according to claim 195, wherein the total dose of gamma radiation is at least 25 kGy.

213. The method according to claim 196, wherein the total dose of gamma radiation is at least 25 kGy.

214. The method according to claim 197, wherein the total dose of gamma radiation is at least 25 kGy.

215. The method according to claim 198, wherein the total dose of gamma radiation is at least 25 kGy.

216. The method according to claim 175, wherein the total dose of gamma radiation is at least 25 kGy.

217. The method according to claim 176, wherein the total dose of gamma radiation is at least 25 kGy.

218. The method according to claim 177, wherein the total dose of gamma radiation is at least 25 kGy.

219. The method according to claim 178, wherein the total dose of gamma radiation is at least 25 kGy.

220. The method according to claim 179, wherein the total dose of gamma radiation is at least 25 kGy.

221. The method according to claim 180, wherein the total dose of gamma radiation is at least 25 kGy.

222. The method according to claim 181, wherein the total dose of gamma radiation is at least 25 kGy.

223. The method according to claim 182, wherein the total dose of gamma radiation is at least 25 kGy.

224. The method according to claim 183, wherein the total dose of gamma radiation is at least 25 kGy.

* * * * *